(12) United States Patent
Mastri et al.

(10) Patent No.: US 12,262,913 B2
(45) Date of Patent: Apr. 1, 2025

(54) DEVICES FOR AND METHODS OF PERFORMING MINIMALLY-INVASIVE SURGICAL PROCEDURES THROUGH A SINGLE INCISION

(71) Applicant: Conmed Corporation, Largo, FL (US)

(72) Inventors: Dominick Mastri, Bridgeport, CT (US); Kurt Azarbarzin, Fairfield, CT (US)

(73) Assignee: Conmed Corporation, Largo, FL (US)

( * ) Notice: Subject to any disclaimer, the term of this patent is extended or adjusted under 35 U.S.C. 154(b) by 563 days.

(21) Appl. No.: 17/235,157

(22) Filed: Apr. 20, 2021

(65) Prior Publication Data

US 2021/0236164 A1 Aug. 5, 2021

Related U.S. Application Data

(60) Continuation of application No. 14/329,497, filed on Jul. 11, 2014, now Pat. No. 10,987,130, which is a
(Continued)

(51) Int. Cl.
*A61B 17/34* (2006.01)
*A61B 17/00* (2006.01)
(Continued)

(52) U.S. Cl.
CPC ...... *A61B 17/3423* (2013.01); *A61B 17/3421* (2013.01); *A61B 17/3462* (2013.01); *A61M 39/0247* (2013.01); *A61B 2017/00986* (2013.01); *A61B 2017/00991* (2013.01); *A61B 17/3431* (2013.01); *A61B 17/3439* (2013.01); *A61B 2017/3443* (2013.01); *A61B 2017/3447* (2013.01); *A61B 2017/347* (2013.01);
(Continued)

(58) Field of Classification Search
CPC ........ A61B 17/3423; A61B 2017/3425; A61B 2017/3433; A61B 17/3439; A61B 17/3462
See application file for complete search history.

(56) References Cited

U.S. PATENT DOCUMENTS 3,721,229 A 3/1973 Panzer
4,362,156 A 12/1982 Feller, Jr. et al.
(Continued)

FOREIGN PATENT DOCUMENTS

DE 2611107 A1 9/1977
EP 0480653 A1 4/1992
(Continued)

OTHER PUBLICATIONS

International Search Report for PCT/US2008/60163.
International Search Report for PCT/US2007/02603.

*Primary Examiner* — Ellen C Hammond
*Assistant Examiner* — Holly Joanna Lane
(74) *Attorney, Agent, or Firm* — Troutman Pepper Locke LLP; Scott D. Wofsy

(57) ABSTRACT

The present invention relates to surgical access devices (or surgical access ports) and related methods. More particularly, the present invention relates to such devices that are advantageously adapted for use in single-incision laparoscopic surgical ("SILS") procedures The present invention also relates to kits and methods involving such surgical access devices.

8 Claims, 33 Drawing Sheets

Related U.S. Application Data division of application No. 12/577,179, filed on Oct. 10, 2009, now Pat. No. 8,795,235, which is a continuation-in-part of application No. 11/786,832, filed on Apr. 13, 2007, now Pat. No. 7,806,870, which is a continuation-in-part of application No. 11/544,856, filed on Oct. 6, 2006, now Pat. No. 7,798,998.

(60) Provisional application No. 61/104,501, filed on Oct. 10, 2008.

(51) Int. Cl.
*A61B 90/00* (2016.01)
*A61M 39/02* (2006.01)
*A61M 39/04* (2006.01)

(52) U.S. Cl.
CPC ... *A61B 2017/3486* (2013.01); *A61B 17/3498* (2013.01); *A61B 90/361* (2016.02); *A61M 2039/0279* (2013.01); *A61M 2039/0291* (2013.01); *A61M 39/045* (2013.01)

(56) References Cited

U.S. PATENT DOCUMENTS

| | | | |
|---|---|---|---|
| 4,607,619 A | 8/1986 | Seike et al. | |
| 4,649,904 A | 3/1987 | Krauter et al. | |
| 4,655,752 A | 4/1987 | Honkanen et al. | |
| 4,676,782 A | 6/1987 | Yamamoto et al. | |
| 4,929,235 A | 5/1990 | Merry et al. | |
| 4,944,732 A * | 7/1990 | Russo | A61M 39/0247 604/105 |
| 4,995,868 A | 2/1991 | Brazier | |
| 5,114,407 A | 5/1992 | Burbank | |
| 5,122,122 A | 6/1992 | Allgood | |
| 5,147,316 A * | 9/1992 | Castillenti | A61B 17/3421 604/174 |
| 5,183,464 A | 2/1993 | Dubrul et al. | |
| 5,186,712 A | 2/1993 | Kelso et al. | |
| 5,232,451 A | 8/1993 | Freitas et al. | |
| 5,242,412 A | 9/1993 | Blake, III | |
| 5,248,302 A | 9/1993 | Patrick et al. | |
| 5,250,025 A | 10/1993 | Sosnowski et al. | |
| 5,257,973 A | 11/1993 | Villasuso | |
| 5,269,772 A | 12/1993 | Wilk | |
| 5,290,245 A | 3/1994 | Dennis | |
| 5,290,249 A | 3/1994 | Foster et al. | |
| 5,300,035 A | 4/1994 | Clement | |
| 5,300,036 A | 4/1994 | Mueller et al. | |
| 5,330,437 A | 7/1994 | Durman | |
| 5,356,421 A | 10/1994 | Castro | |
| 5,366,445 A * | 11/1994 | Haber | A61B 17/3496 604/164.01 |
| 5,366,478 A | 11/1994 | Brinkerhoff et al. | |
| 5,383,861 A | 1/1995 | Hempel et al. | |
| 5,407,427 A | 4/1995 | Zhu et al. | |
| 5,423,770 A | 6/1995 | Yoon | |
| 5,431,676 A | 7/1995 | Dubrul et al. | |
| 5,437,683 A | 8/1995 | Neumann et al. | |
| 5,441,041 A | 8/1995 | Sauer et al. | |
| 5,445,615 A | 8/1995 | Yoon | |
| 5,454,790 A | 10/1995 | Dubrul | |
| 5,456,284 A | 10/1995 | Ryan et al. | |
| 5,460,170 A | 10/1995 | Hammerslag | |
| 5,472,429 A | 12/1995 | Yoon | |
| 5,490,843 A | 2/1996 | Hildwein et al. | |
| 5,524,644 A | 6/1996 | Crook | |
| 5,545,179 A | 8/1996 | Williamson, IV | |
| 5,620,456 A * | 4/1997 | Sauer | A61B 17/3417 604/164.01 |
| 5,634,937 A | 6/1997 | Mollenauer et al. | |
| 5,657,097 A | 8/1997 | Schultz et al. | |
| 5,685,820 A | 11/1997 | Riek et al. | |
| 5,697,913 A | 12/1997 | Sierocuk et al. | |
| 5,702,370 A | 12/1997 | Sylvanowicz et al. | |
| 5,707,362 A * | 1/1998 | Yoon | A61B 17/3417 604/164.03 |
| 5,713,869 A | 2/1998 | Morejon | |
| 5,725,504 A | 3/1998 | Collins | |
| 5,727,770 A | 3/1998 | Dennis | |
| 5,782,813 A | 7/1998 | Yoon | |
| 5,797,835 A | 8/1998 | Green | |
| 5,817,062 A | 10/1998 | Flom et al. | |
| 5,827,319 A | 10/1998 | Carlson et al. | |
| 5,830,191 A | 11/1998 | Hildwein et al. | |
| 5,836,913 A | 11/1998 | Orth et al. | |
| 5,895,377 A | 4/1999 | Smith et al. | |
| 5,906,595 A | 5/1999 | Powell et al. | |
| 5,935,107 A | 8/1999 | Taylor et al. | |
| 5,980,549 A | 11/1999 | Chin | |
| 5,997,515 A | 12/1999 | de la Torre et al. | |
| 6,077,288 A | 6/2000 | Shimomura et al. | |
| 6,123,689 A | 9/2000 | To et al. | |
| 6,142,981 A | 11/2000 | Heck et al. | |
| 6,196,967 B1 | 3/2001 | Lim et al. | |
| 6,206,823 B1 | 3/2001 | Kolata et al. | |
| 6,228,059 B1 | 5/2001 | Astarita | |
| 6,258,065 B1 | 7/2001 | Dennis et al. | |
| 6,312,394 B1 | 11/2001 | Fleming, III | |
| 6,340,351 B1 | 1/2002 | Goldenberg | |
| 6,364,892 B1 | 4/2002 | Jervis | |
| 6,432,085 B1 | 8/2002 | Stellon et al. | |
| 6,454,783 B1 | 9/2002 | Piskun | |
| 6,524,238 B2 | 2/2003 | Velikaris et al. | |
| 6,540,735 B1 | 4/2003 | Ashby et al. | |
| 6,656,198 B2 | 12/2003 | Tsonton et al. | |
| 6,669,674 B1 | 12/2003 | Macoviak et al. | |
| 6,669,709 B1 | 12/2003 | Cohn et al. | |
| 6,706,033 B1 | 3/2004 | Martinez et al. | |
| 6,749,589 B1 | 6/2004 | Douglas et al. | |
| 6,808,492 B2 | 10/2004 | Snyder | |
| 6,811,546 B1 | 11/2004 | Callas et al. | |
| 6,814,715 B2 | 11/2004 | Bonutti et al. | |
| 6,837,891 B2 | 1/2005 | Davison et al. | |
| 6,860,869 B2 | 3/2005 | Dennis | |
| 6,972,026 B1 | 12/2005 | Caldwell et al. | |
| 7,052,454 B2 | 5/2006 | Taylor | |
| 7,056,303 B2 | 6/2006 | Dennis et al. | |
| 7,056,329 B2 * | 6/2006 | Kerr | A61B 17/3496 606/190 |
| 7,201,740 B2 | 4/2007 | Crawford | |
| 7,473,243 B2 | 1/2009 | Dennis et al. | |
| 2001/0012946 A1 | 8/2001 | MacKenzie et al. | |
| 2003/0093104 A1 | 5/2003 | Bonner et al. | |
| 2004/0243073 A1 | 12/2004 | Lockwood et al. | |
| 2004/0260246 A1 | 12/2004 | Desmond | |
| 2005/0004592 A1 | 1/2005 | Criscuolo | |
| 2005/0013832 A1 | 1/2005 | Rose | |
| 2005/0051163 A1 | 3/2005 | Deem et al. | |
| 2005/0119685 A1 * | 6/2005 | Smith | A61B 17/3439 606/198 |
| 2005/0203565 A1 | 9/2005 | Rethy et al. | |
| 2005/0228445 A1 | 10/2005 | Mollenauer et al. | |
| 2006/0020241 A1 | 1/2006 | Piskun et al. | |
| 2006/0224174 A1 | 10/2006 | Smith et al. | |
| 2007/0088258 A1 | 4/2007 | Wenchell et al. | |
| 2007/0088277 A1 * | 4/2007 | McGinley | A61M 13/003 604/167.01 |
| 2008/0255519 A1 | 10/2008 | Piskun et al. | |
| 2009/0093683 A1 | 4/2009 | Richard et al. | |
| 2009/0182279 A1 | 7/2009 | Wenchell et al. | |
| 2009/0312710 A1 | 12/2009 | Smith | |
| 2010/0145142 A1 * | 6/2010 | Begemann | A61B 1/018 128/898 |

FOREIGN PATENT DOCUMENTS

| | | |
|---|---|---|
| EP | 0487175 A1 | 5/1992 |
| EP | 1774918 A1 | 4/2007 |
| FR | 2810555 A1 | 12/2001 |
| GB | 2275420 A | 8/1994 |
| WO | 200234108 A2 | 5/2002 |

(56) References Cited

FOREIGN PATENT DOCUMENTS

| | | | |
|---|---|---|---|
| WO | 2004028613 | A2 | 4/2004 |
| WO | 2005013632 | A1 | 2/2005 |
| WO | 2005013832 | A1 | 2/2005 |
| WO | 2008042005 | A1 | 4/2008 |

\* cited by examiner

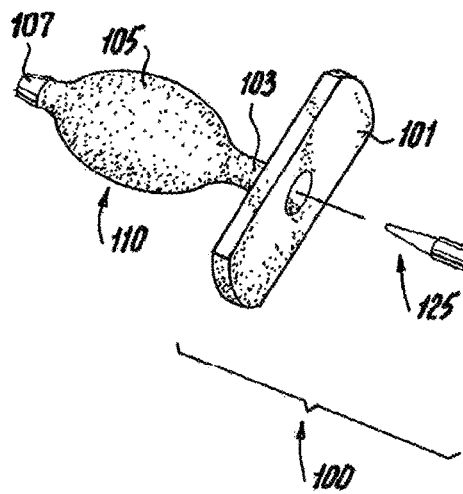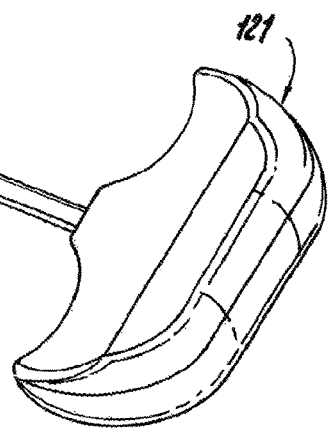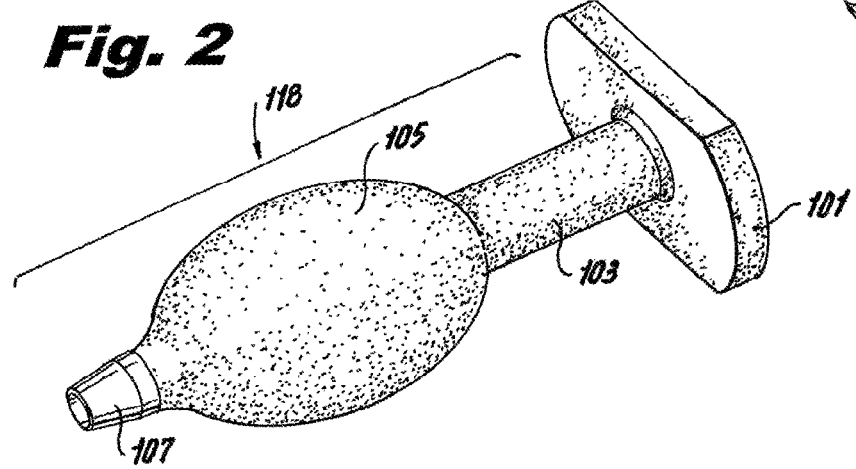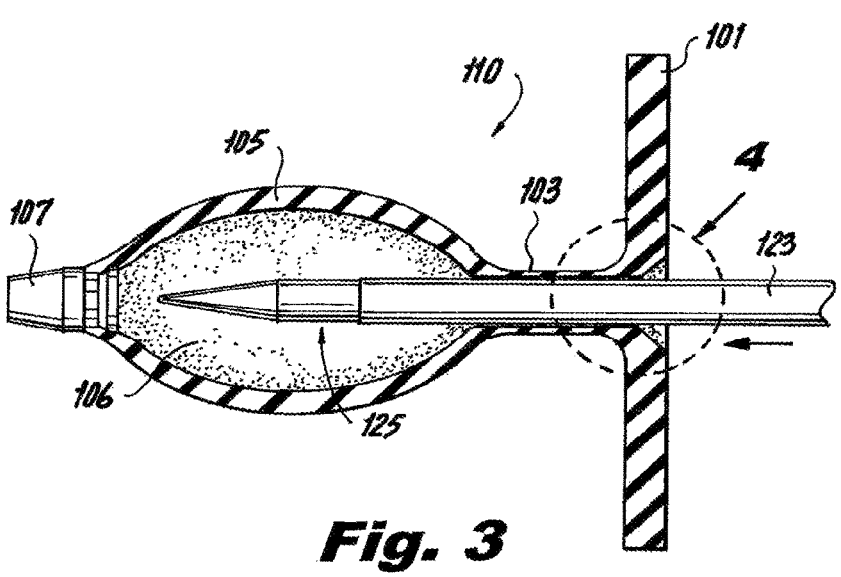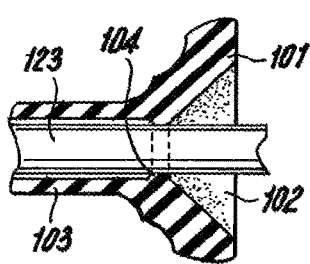

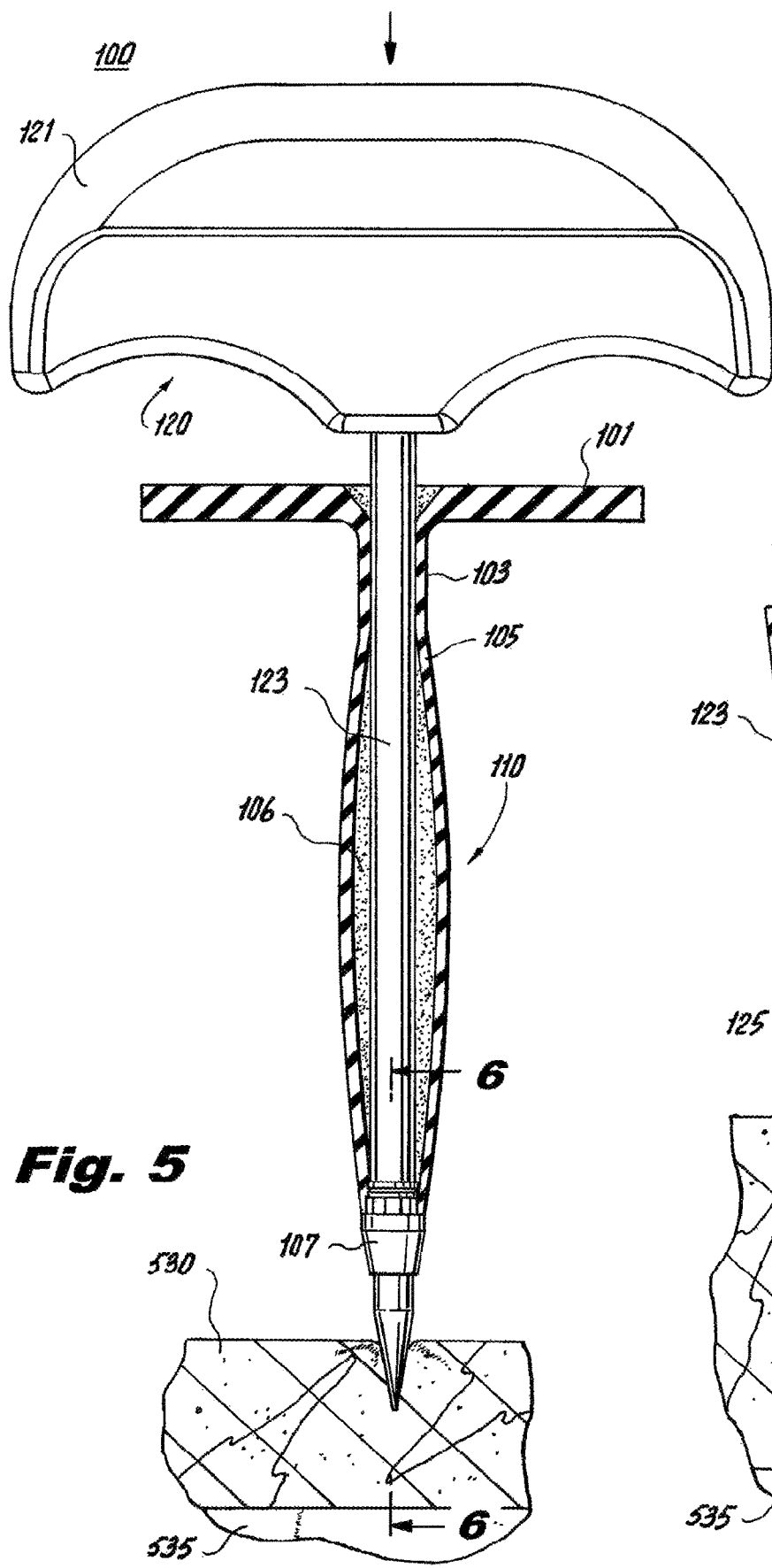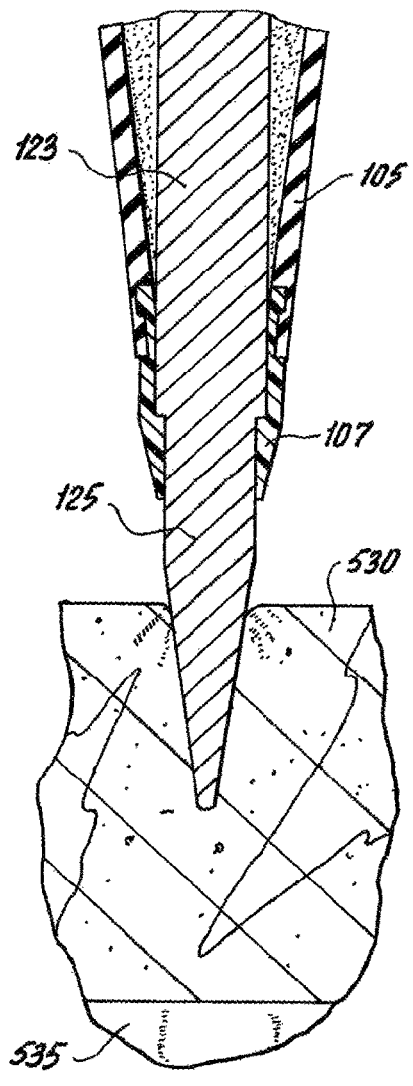

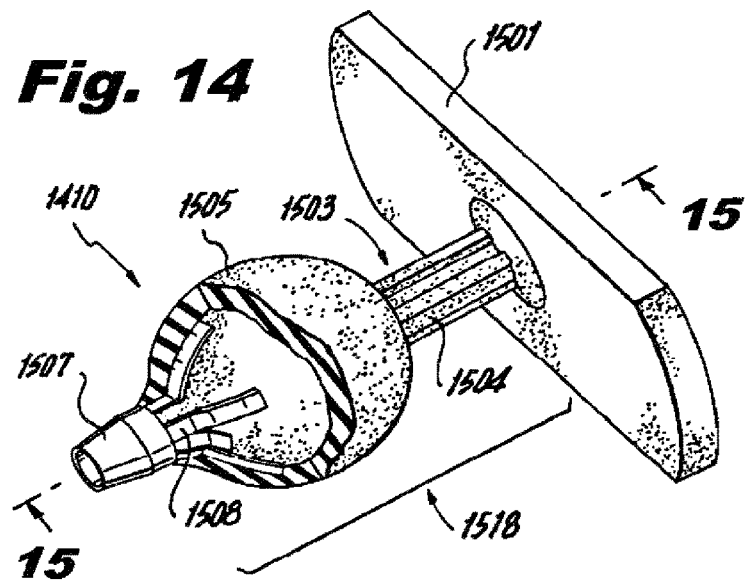
Fig. 14
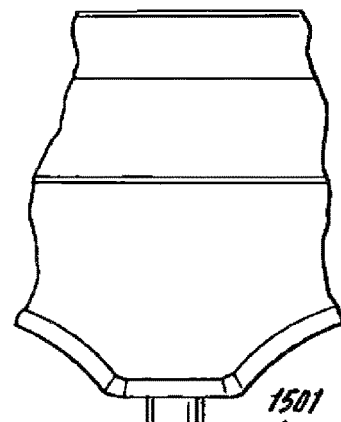
Fig. 16
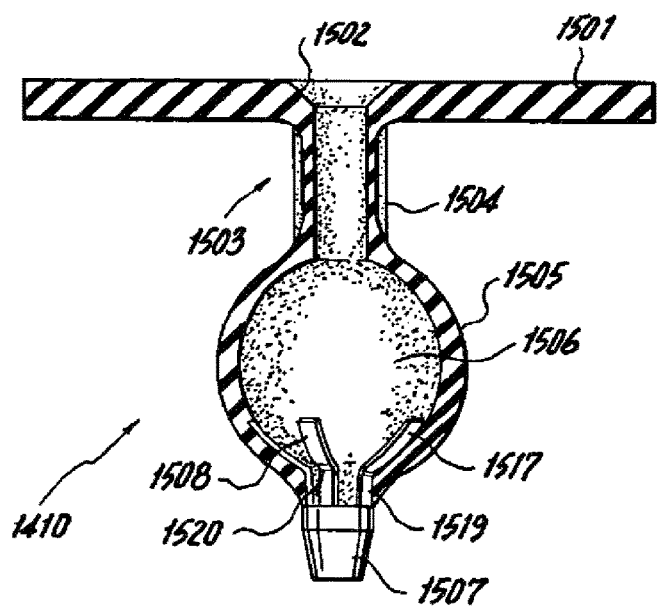
Fig. 15
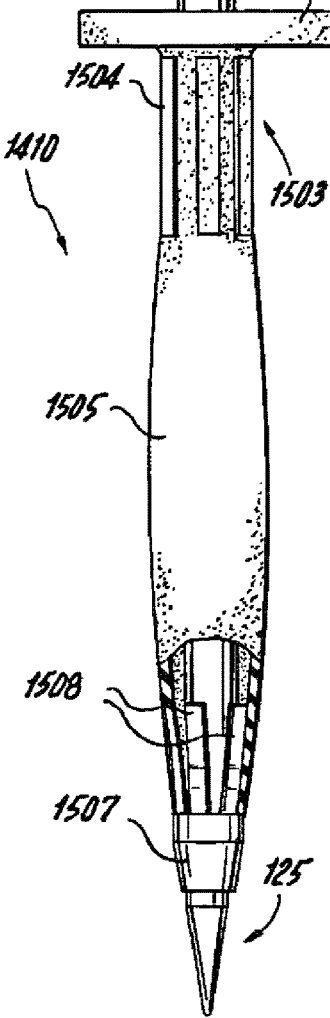

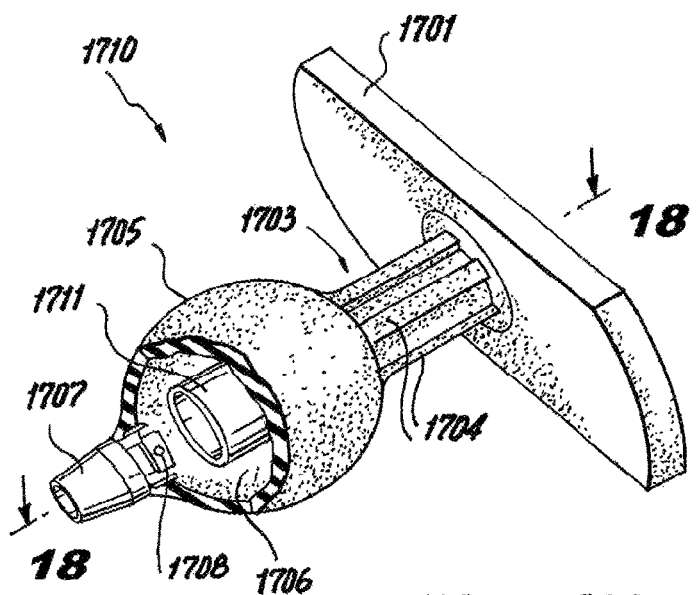
Fig. 17
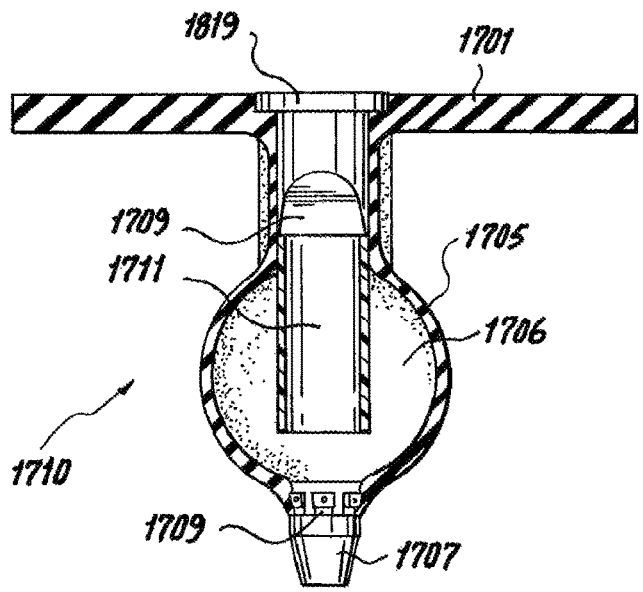
Fig. 18
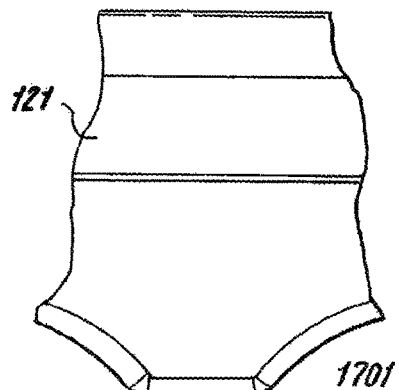
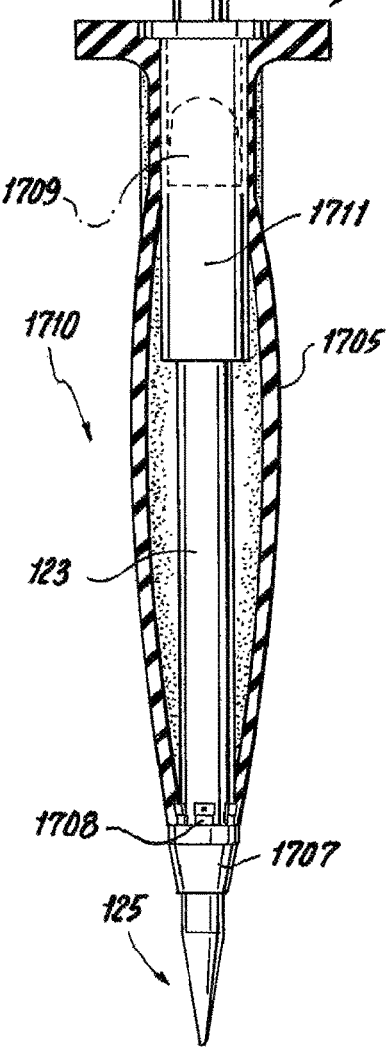
Fig. 19

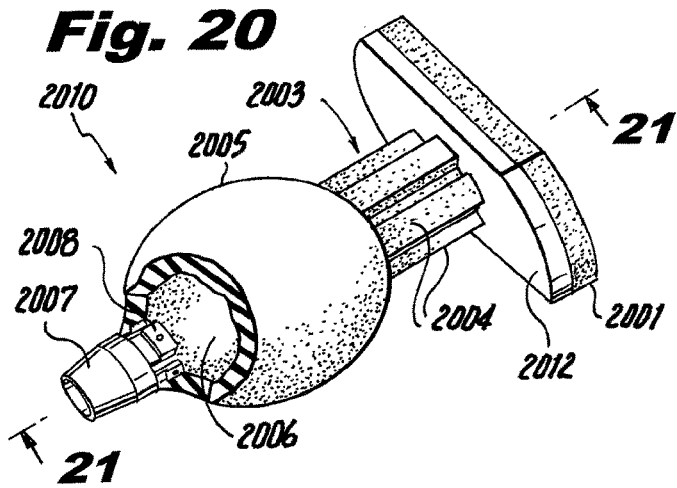
Fig. 20
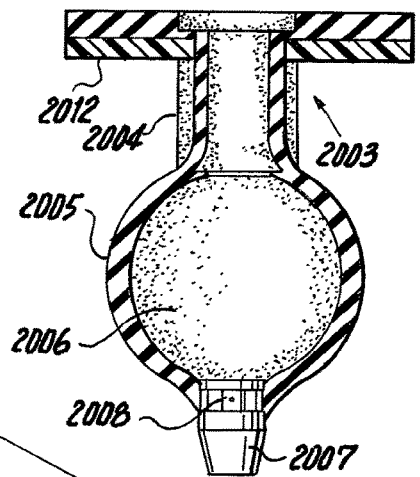
Fig. 21
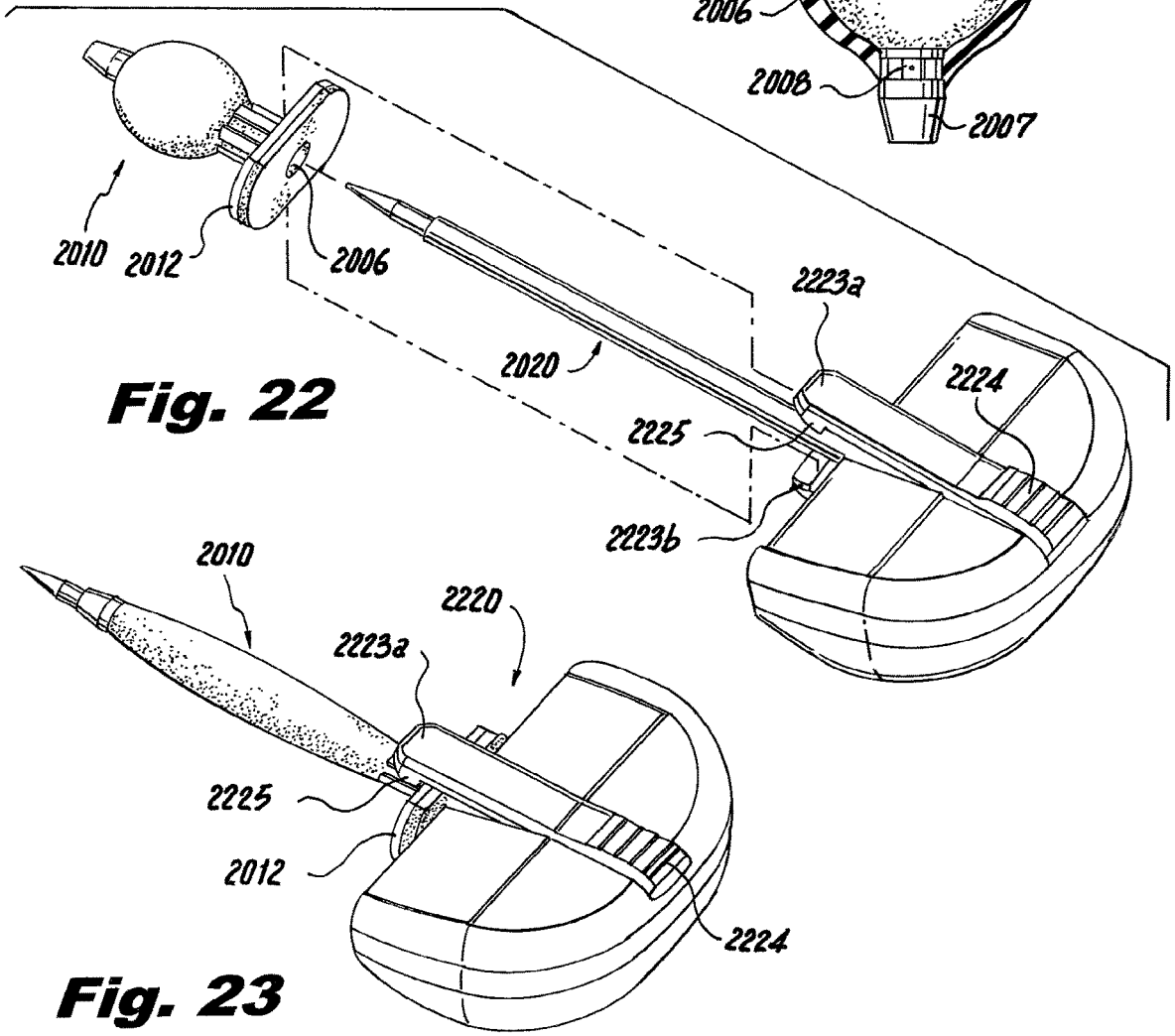
Fig. 22
Fig. 23

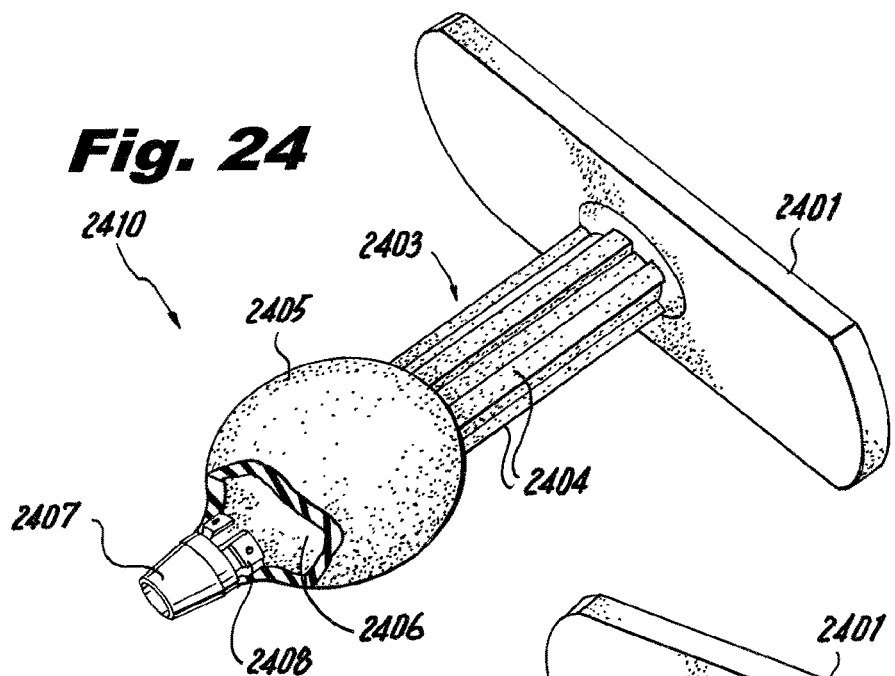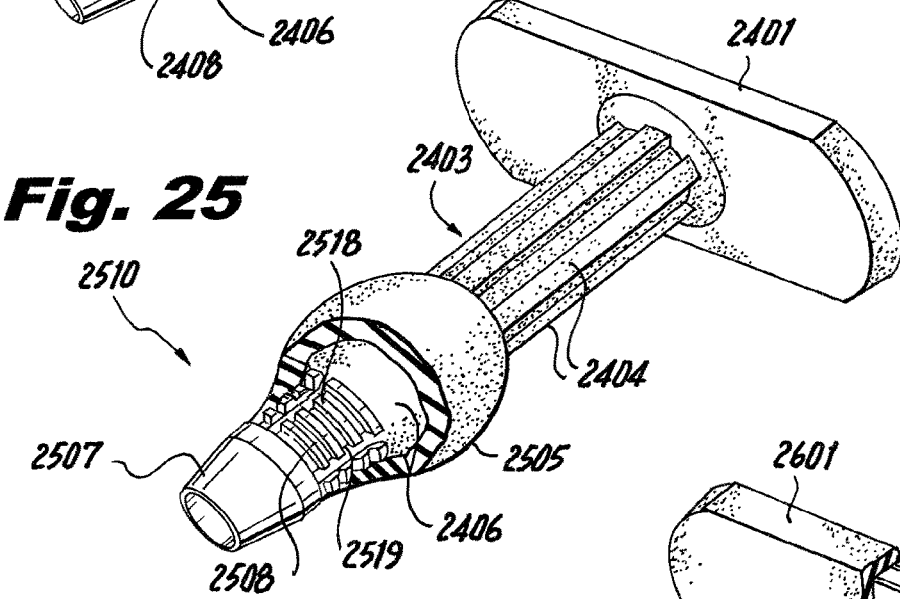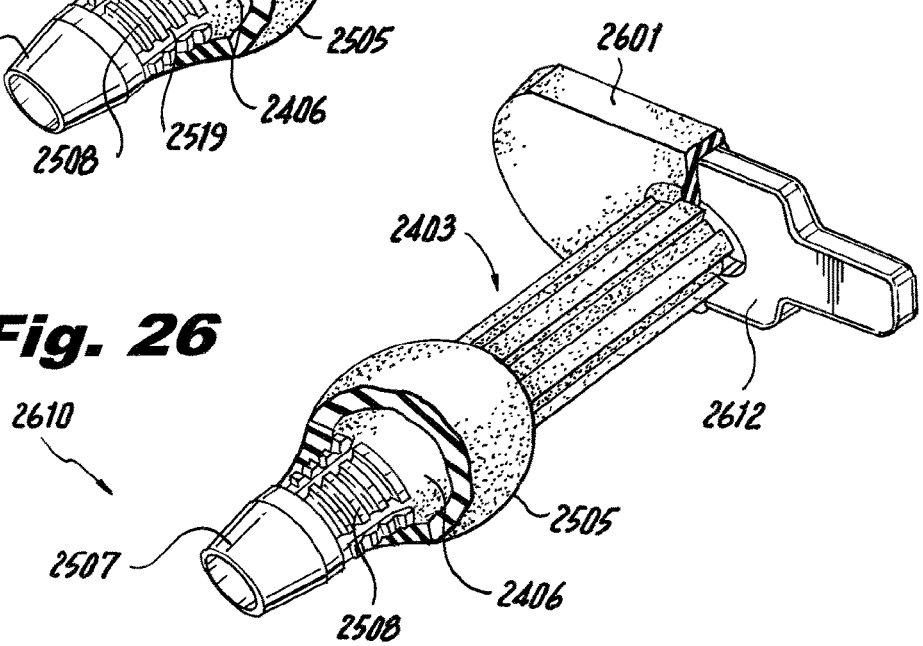

Fig. 29
Fig. 32
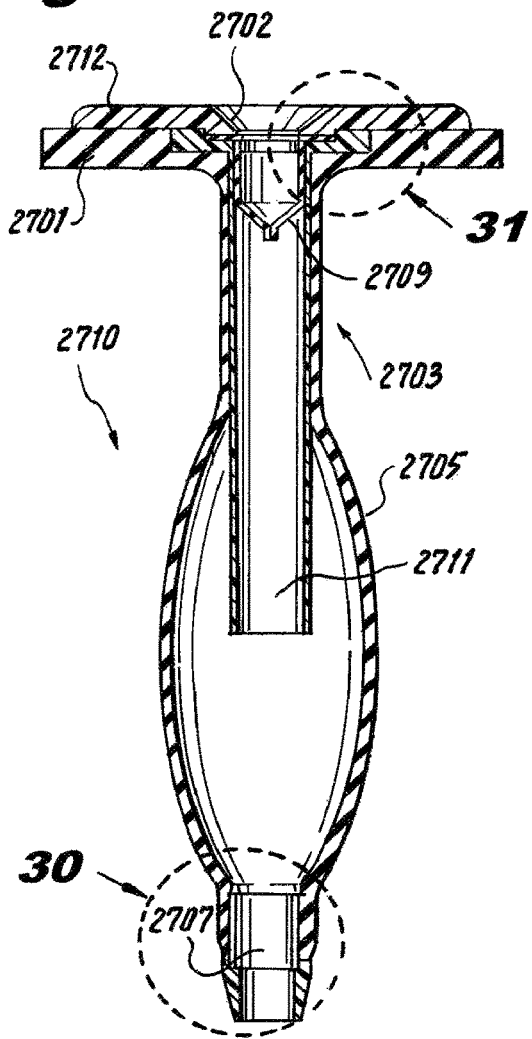
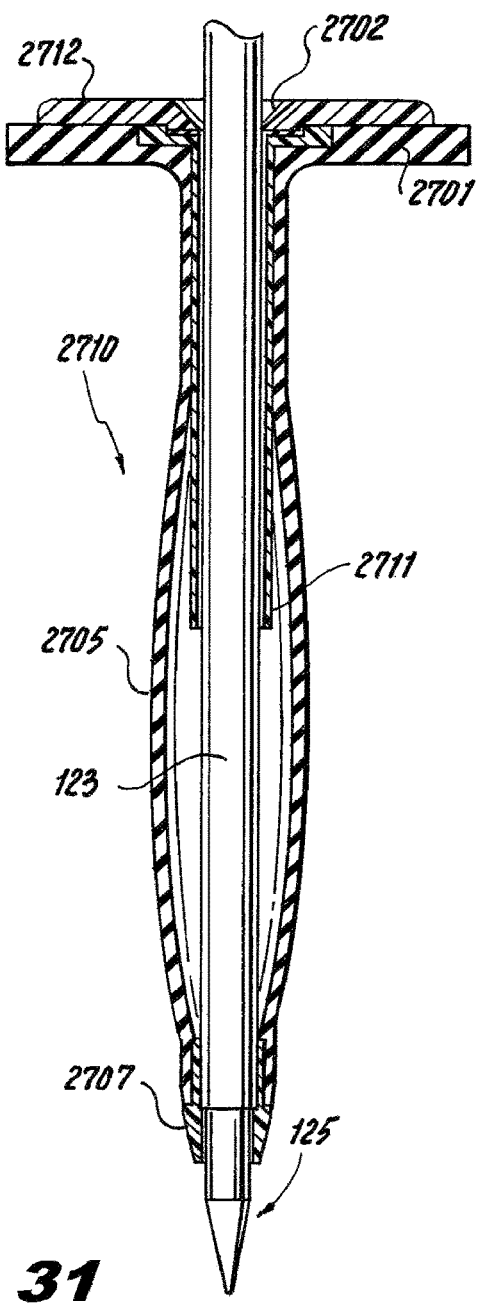
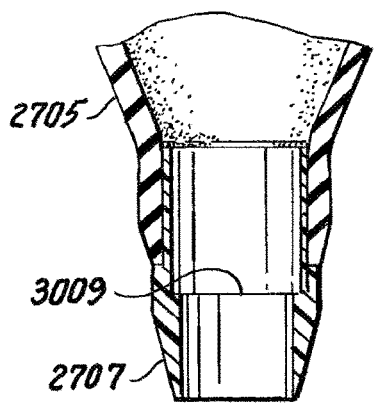
Fig. 30
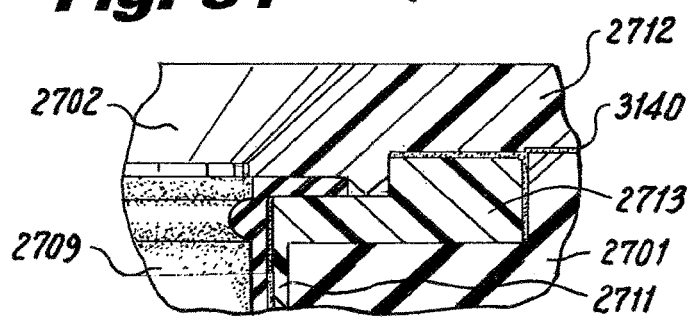
Fig. 31

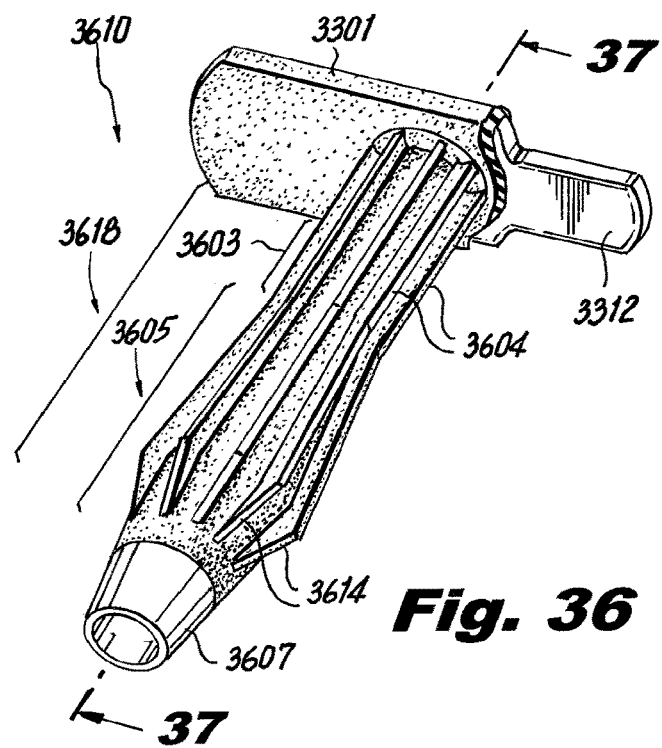
Fig. 36
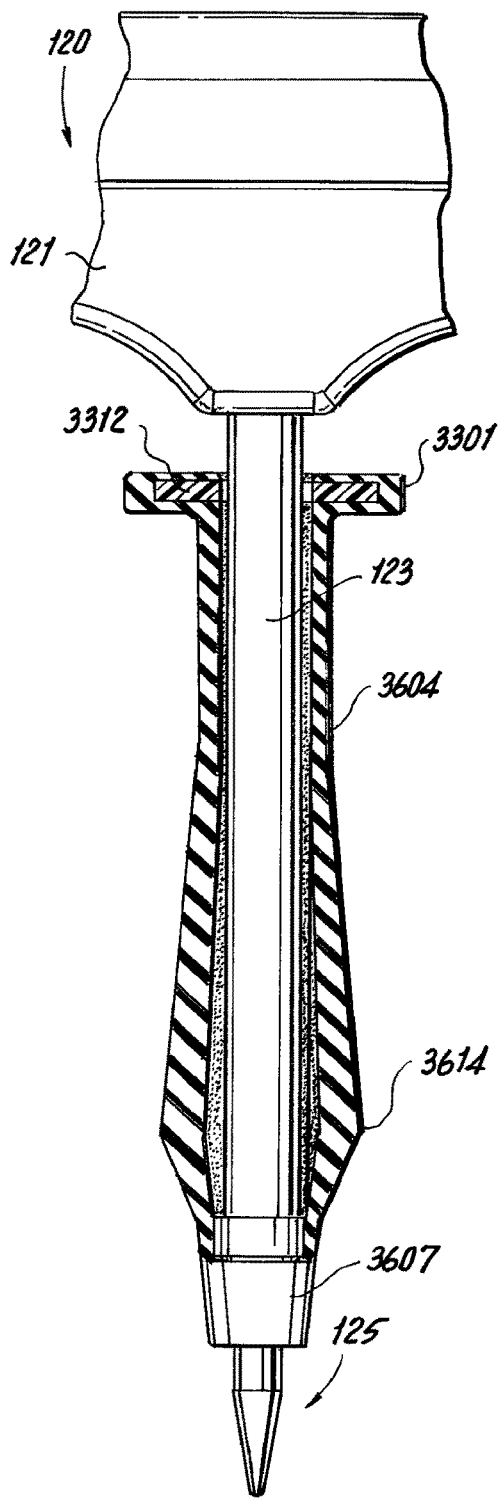
Fig. 37
Fig. 38

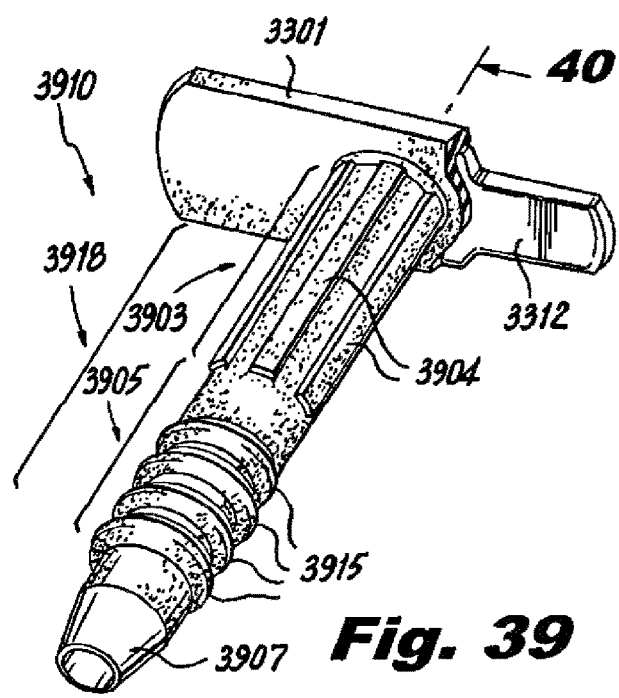
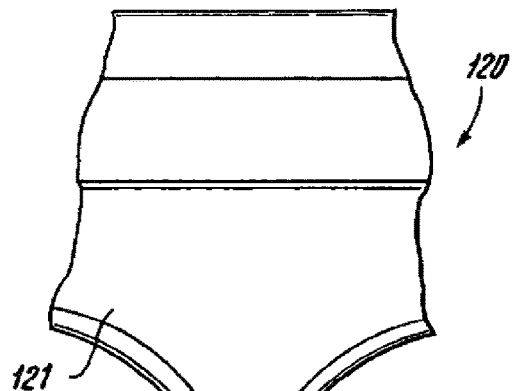
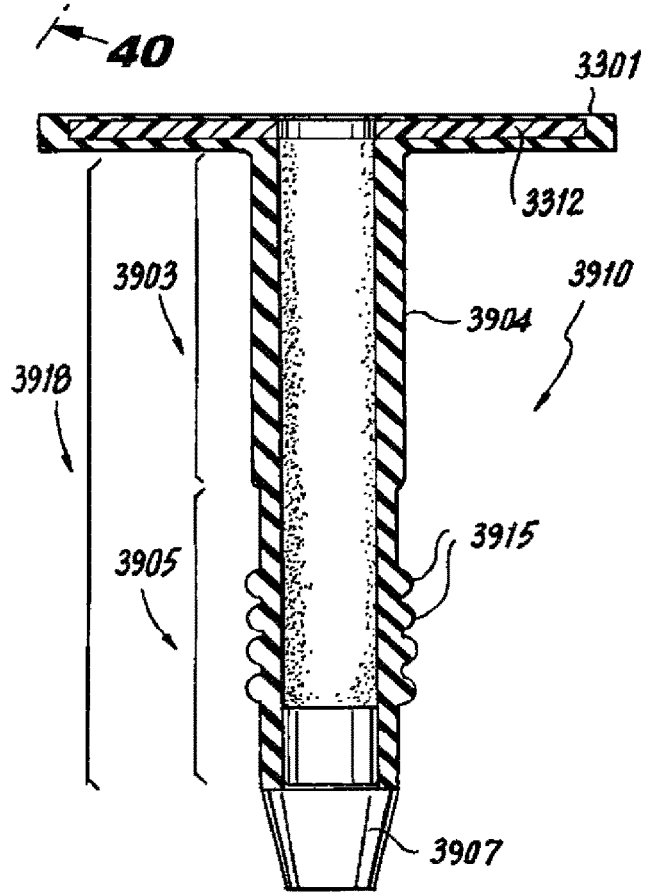
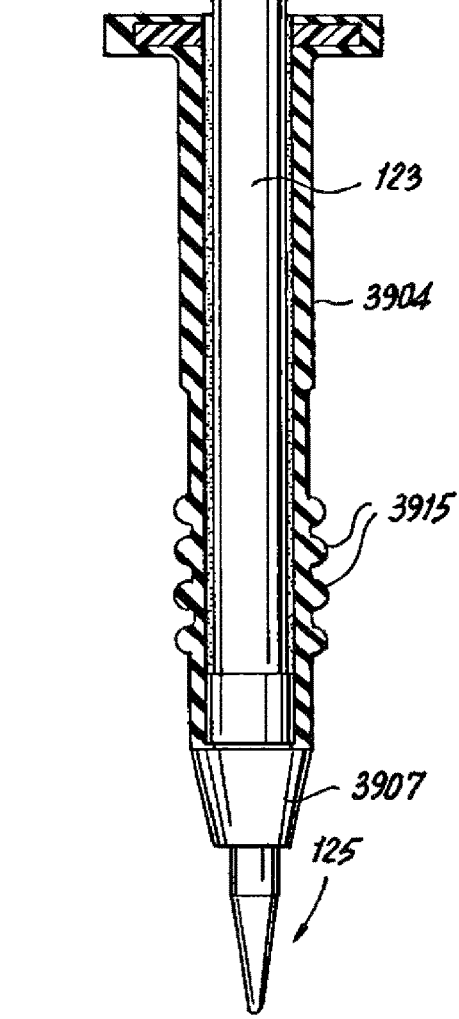
Fig. 39
Fig. 40
Fig. 41

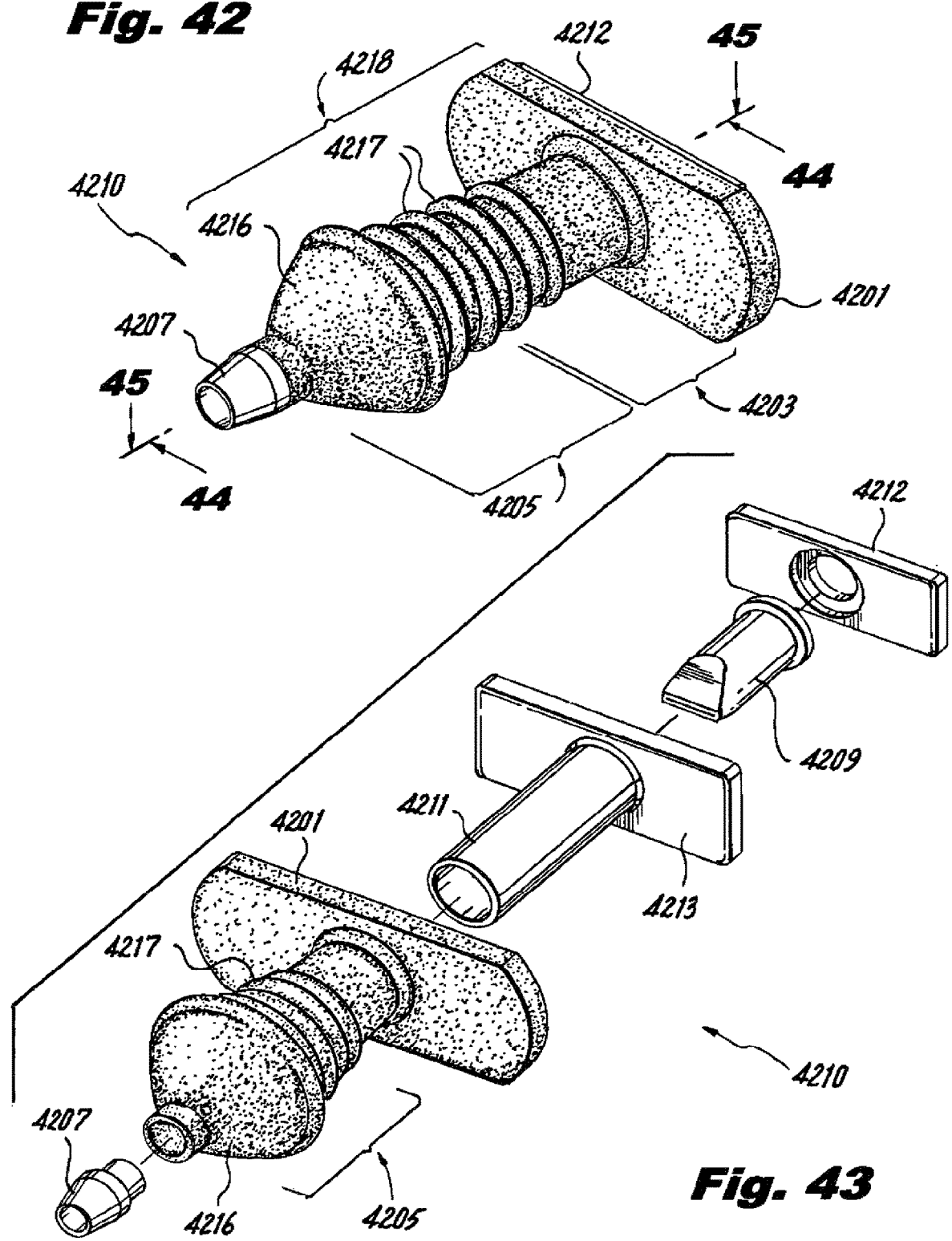

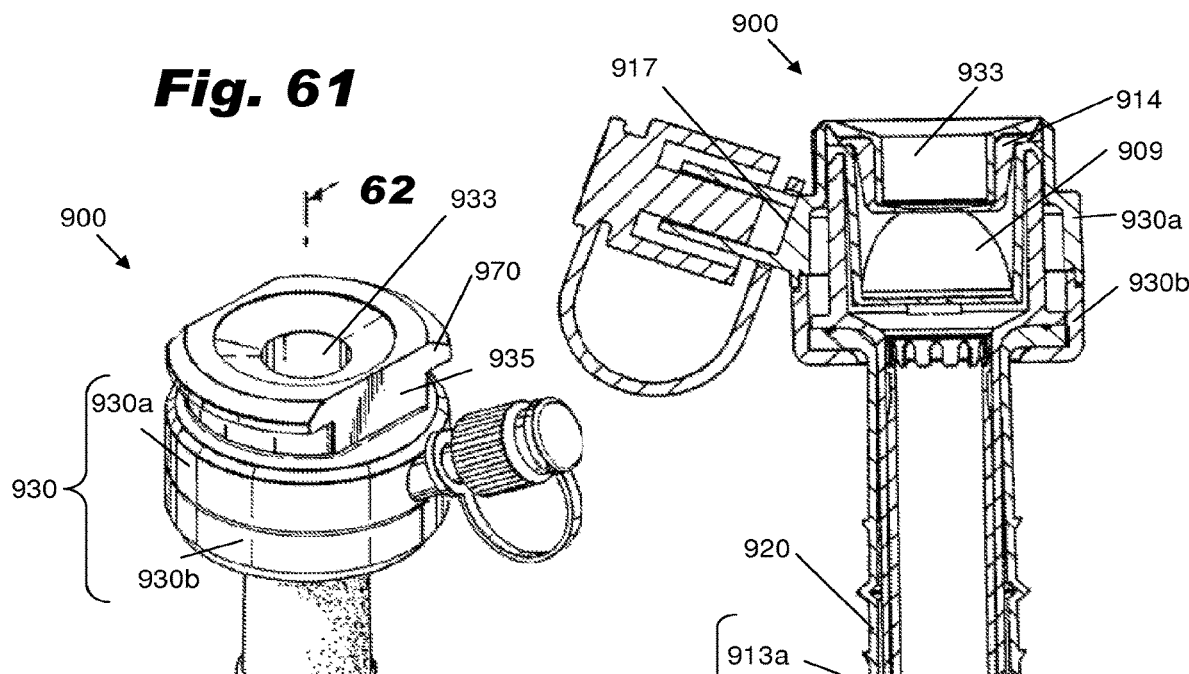
Fig. 61
Fig. 62
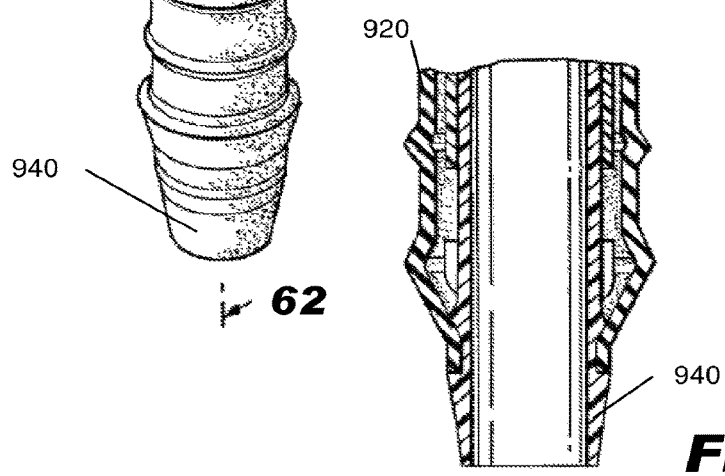
Fig. 63

DEVICES FOR AND METHODS OF PERFORMING MINIMALLY-INVASIVE SURGICAL PROCEDURES THROUGH A SINGLE INCISION

CROSS-REFERENCE TO RELATED APPLICATIONS

This Application is a Continuation of U.S. patent application Ser. No. 14/329,497, filed on Jul. 11, 2014, now U.S. Pat. No. 10,987,130, which application is a Divisional of U.S. patent application Ser. No. 12/577,179 filed on Oct. 10, 2009, now U.S. Pat. No. 8,795,235, which is a continuation-in-part of U.S. patent application Ser. No. 11/786,832, filed Apr. 13, 2007, now U.S. Pat. No. 7,806,870, which is continuation-in-part of U.S. patent application Ser. No. 11/544,856, filed Oct. 6, 2006, now U.S. Pat. No. 7,798,998. This Application also claims the benefit of priority to U.S. Provisional Patent Application No. 61/104,501, filed Oct. 10, 2008. Each of the foregoing applications is hereby incorporated by reference in its entirety.

BACKGROUND

1. Field of the Invention

The present invention relates to surgical access devices (or surgical access ports) and related methods. More particularly, the present invention relates to such devices that are advantageously adapted for use in single-incision laparoscopic surgical ("SILS") procedures The present invention also relates to kits and methods involving such surgical access devices.

2. Description of the Related Art

Increasingly, techniques are being developed for performing minimally invasive surgical procedures with a single incision, in order to reduce trauma and reduce the amount of scarring of a patient. It is often difficult to insert multiple traditional surgical instruments simultaneously through a single incision, due to mutual interference, and lack of available space. It has therefore become necessary to develop devices, systems and procedures to facilitate such approaches. The present invention provides a many outstanding challenges in the art.

SUMMARY

The purpose and advantages of the present invention will be set forth in and apparent from the description that follows. Additional advantages of the invention will be realized and attained by the devices and methods particularly pointed out in the written description and claims hereof, as well as from the appended drawings.

In accordance with one aspect of the invention, a method of performing a laparoscopic surgical procedure is providing, comprising the steps of, creating an incision in a patient to access a surgical site, inserting a first surgical access port into the incision, inserting a second surgical access port into the incision, and inserting a third surgical access port between the second and third surgical access ports, at least one access port having a length longer than at least one other surgical access port.

One or more of the surgical access ports can include an elongated body with opposed proximal and distal end portions, the body having a central lumen extending therethrough and having a resilient bulb portion formed between the proximal and distal end portions thereof, wherein the resilient bulb portion is adapted and configured to transition between a first condition in which the bulb portion has a first diameter and a first length and a second condition in which the bulb portion has a second diameter that is less than the first diameter and a second length that is greater than the first length, and optionally a telescoping guide tube assembly disposed within the central lumen of the body, wherein the guide tube assembly is adapted and configured to transition between a first length corresponding to the first condition of the bulb portion and a second length corresponding to the second condition of the bulb portion.

The aforementioned surgical procedures can be any desired, including a hysterectomy or cholecystectomy, for example.

In accordance with another aspect of the invention, a kit for performing a minimally invasive surgical procedure is provided, having a plurality of surgical access ports. Each access port can include an elongated body with opposed proximal and distal end portions, the body having a central lumen extending therethrough and having a resilient bulb portion formed between the proximal and distal end portions thereof, wherein the resilient bulb portion is adapted and configured to transition between a first condition in which the bulb portion has a first diameter and a first length and a second condition in which the bulb portion has a second diameter that is less than the first diameter and a second length that is greater than the first length, and optionally, a telescoping guide tube assembly disposed within the central lumen of the body, wherein the guide tube assembly is adapted and configured to transition between a first length corresponding to the first condition of the bulb portion and a second length corresponding to the second condition of the bulb portion, wherein at least one of the surgical access ports has an overall length longer than at least one of the other surgical access ports provided in the kit.

With such kits, three access ports can be included, one of the access ports being longer than the remaining two access ports. Likewise, four access ports can be included, two of the access ports being longer than the remaining two access ports.

If desired, at least one of the plurality of access ports can be adapted and configured for nesting with at least one other of the plurality of access ports. For example, the housings at the proximal ends thereof can be configured to facilitate mutual close placement thereof. Accordingly, such housings can be provided with a minimally-sized housing in diameter and/or height in whole, or in a portion thereof, for example.

In accordance with the invention, if insufflation capability is desired through the access port or ports, only one port having insufflation capability is required to provide such capability. Accordingly, kits can be provided having only one port with such capability. Minimizing a number of insufflation ports on the set of devices minimizes the size of the devices without ports, thus enhancing close-positioning of adjacent ports.

In accordance with the foregoing aspects, the following features can be incorporated therewith, as desired. The bulb portion can have, for example, a generally spherical, generally ovoid, or other shape configuration in the first condition. The bulb portion of the access port body can be formed at least in part from an elastomeric material, such as silicone rubber. The bulb portion can have an outer surface with a substantially convex arcuate contour. The proximal end portion of the access port body can have a substantially constant outer diameter. Further, the bulb portion in the first condition can include an expanded diameter, or can be substantially straight. Additionally or alternatively, the bulb portion can include one or more circumferential longitudinally spaced ribs or longitudinal circumferentially-spaced ribs.

An insert sleeve can be disposed within the distal end portion of the access port body for engaging a distal end portion of the trocar and can be arranged at the distal end of the access port body, forming a tip thereof. Such insert sleeve can be formed from a material having a greater rigidity than the access port body, and can be, for example, Nylon. The insert sleeve can include a plurality of proximally extending expandable guide fingers for lining an inner surface of the bulb portion to accommodate or facilitate insertion of the trocar. Additionally, if desired, an elongated guide tube can be provided, which extends through the proximal portion of the access port body and at least partially into the bulb portion of the access port body.

Further, if desired, a substantially rigid generally planar flange portion can be associated with the proximal end portion of the access port body, and can define an access port communicating with the lumen of the access port body. Such access port can have a conically tapering lead-in surface. If provided, the insertion device can include a handle with releasable locking means for releasably engaging aforementioned flange portion.

If desired or required, the proximal portion of the access port body can be provided with longitudinal, circumferentially spaced ribs formed on an outer surface of the body, for inhibiting elongation of the proximal end portion of the access port body during the transition from the first condition of the bulb portion to the second condition of the bulb portion. Alternatively or additionally, the proximal portion of the access port body can be provided with circumferential, longitudinally spaced ribs formed on an outer surface of the body, for inhibiting circumferential expansion of the proximal end portion of the access port body during the transition from the first condition of the bulb portion to the second condition of the bulb portion. Additionally or alternatively, the body can be provided with circumferential, longitudinally spaced ribs formed on an outer surface of the body, for inhibiting removal of the bulb portion from an abdominal wall of a patient.

In accordance with the invention, a seal member can be disposed within the lumen, in the proximal end portion of the access port body. Such seal member can be, for example, a duckbill-type valve, ball valve, or a fluid seal as set forth, for example in U.S. patent application Ser. No. 11/517,929 filed Sep. 8, 2006. Such seal member can include both an annular sealing portion for sealing against an instrument shaft inserted therethrough and a duckbill-type sealing portion for sealing the port in the absence of an instrument inserted therethrough. Such seal members can consist of include molded elastomeric part, or, alternatively, two separate parts. Additionally or alternatively, an integrally formed seal can be provided within the lumen, in the proximal end portion of the access port body. Such seal can be, for example, a protrusion provided on the wall of the lumen, to seal a space between the wall of the lumen and a surgical instrument. Alternatively or additionally, sealing can be accomplished by way of a collapsible region defined in the proximal end portion of the body such that the collapsible region can be collapsed by an outside force, to seal the lumen. Such outside force can be, for example, force exerted by the abdominal wall of a patient.

The body can be provided with a first engagement means in the distal end portion thereof, such that a distal end portion of a trocar can engage the first engagement means. Such engagement means can be tabs, which are configured and arranged to be grasped by the trocar, or alternatively, a substantially rigid stepped element, for engaging a mating portion of the trocar. If desired, the body can be provided with second engagement means in the proximal end portion thereof, with a proximal end of the trocar, obturator or other insertion device being adapted for engaging the second engagement means.

In the foregoing embodiments, the trocar or insertion device preferably has a length greater than the first length of the bulb portion of the body, and therefore causes extension of the bulb portion to the second length. If a second engagement means is arranged in the proximal end portion of the body, for engagement with a proximal end portion of the trocar or insertion device, the insertion device can maintain the access port body in the second condition while engaged therewith.

In accordance with another preferred embodiment of the subject invention, there is provided a surgical access device that includes, among other things, a telescoping guide tube assembly disposed within the central lumen of the access port body for accommodating the elongated insertion device. The guide tube assembly is adapted and configured to transition between a first length corresponding to the first condition of the bulb portion and a second length corresponding to the second condition of the bulb portion. In addition, the insertion device is configured to extend through the guide tube assembly and releasably engage the guide tube assembly to facilitate the transition of the access device from the first condition of the bulb portion to the second condition of the bulb portion.

Preferably, the telescoping guide tube assembly includes a proximal tube section and a distal tube section. The proximal tube section is fixed relative to the access port body and the distal tube section is adapted to translate relative to the proximal tube section. The distal tube section of the guide tube assembly includes a nosepiece that extends from the distal end portion of the access port body and has a tapered outer surface. Preferably, the tapered outer surface of the nosepiece merges into the bulb portion of the access port body, to provide a smooth transition between the two structures. The guide tube assembly has an interior engagement ring therein for mating with an exterior engagement ring provided on the insertion device.

The access port body also includes a plurality of axially spaced apart annular retaining ribs. The plurality of axially spaced apart annular retaining ribs includes two different rib structures. These include a first rib structure having a horizontal ledge and an angularly inclined riser and a second rib structure having a generally V-shaped cross-section.

In addition, the access port includes a proximal housing portion that includes an inlet opening communicating with the guide tube assembly. The housing portion has an interior chamber that houses a seal member designed to interact with the insertion device or a surgical device inserted through the access port. The seal member preferably includes a duckbill seal portion and an annular wiper seal portion.

The insertion device used to facilitate the transition of the bulb portion between the first and second conditions includes a proximal handle assembly and an elongated trocar shaft that extends distally from the handle assembly. The handle assembly preferably includes means for engaging the proximal housing portion of the access port. In this regard, the proximal housing portion of the access port includes a proximal engagement flange and the handle assembly of the insertion device includes a pair of opposed pivoting latching arms for releasably engaging the flange of the access port.

Preferably, the pivoting locking arms of the handle assembly are normally biased into a latching position by spring arms or the like disposed within the handle assembly. The insertion device preferably has a tissue-penetrating tip at the distal end of the trocar shaft. The tissue-penetrating tip preferably includes at least two cutting surfaces or facets, and more preferably, the facets define optical lens areas for visualization during the tissue penetration procedure.

In addition, the handle assembly includes means for receiving a laparoscope that would communicate with the optical lens areas of the trocar tip. In this regard, the handle assembly includes means for securing the position of a laparoscope relative to the insertion device. Preferably, the means for securing the position of the laparoscope relative to the insertion device includes a rotatable cam lock that interacts with a silicone washer designed to compressively engage an outer periphery of the laparoscope. These and other unique features of the access device and the insertion device will become more readily apparent from the following detailed description of the preferred embodiments of the invention taken in conjunction with the associated figures.

In accordance with still another aspect of the invention, a method of forming an access port in a patient is provided. The method includes the steps of providing an access port in accordance with the invention, as set forth herein; providing an insertion device configured to engage the distal end portion of the access port body; extending the insertion device into the central lumen of the access port body so as to engage the distal end portion of the access port body; elongating the access port with the insertion device, the end of the insertion device being engaged with the distal end portion of the access port body; inserting the access port and insertion device through an abdominal wall of a patient to a predetermined position, while maintaining the access port in an elongated configuration; and removing the insertion device from the access port, allowing the access port to revert to the first configuration, with the bulb portion of the access port engaging an interior surface of the abdominal wall.

The method can further include the step of performing surgery by inserting a surgical instrument through the lumen of the access port, and through an optional rigid member associated with a portion of the body. The method can further include sealing the central lumen, either upon itself, or between the access port and a surgical instrument. Such sealing can occur by radially inwardly directed force acting on the access port, exerted by the abdominal wall of the patient.

Additionally or alternatively, the step of elongating the access port with the insertion device can further include engaging the insertion device with a first engagement means at the distal end of the access port and elongating the port along the insertion device. Additionally or alternatively, the method can further include the step of engaging a second engaging means associated with the proximal end of the access port with a corresponding engagement means on the insertion device to selectively maintain the access port body in an elongated configuration.

In accordance with the invention, the step of inserting the port can include inserting the access port through the abdominal wall with the insertion device in engagement with the first and second engagement means of the access port. The methods set forth herein can further include removing the access port from the abdominal wall. Such removal can include reengaging the insertion device with the first and second engagement means to elongate the access port body, and withdrawing the elongated access port from the abdominal wall.

It is to be understood that both the foregoing general description and the following detailed description are exemplary and are intended to provide further explanation of the invention claimed.

BRIEF DESCRIPTION OF THE DRAWINGS

The accompanying drawings, which are incorporated in and constitute part of this specification, are included to illustrate and provide a further understanding of the devices and methods of the invention. Together with the description, the drawings serve to explain the principles of the invention, wherein:

FIG. 1 is an isometric view of a first representative embodiment of a surgical access device in accordance with the present invention, including an insertion device and an access port;

FIG. 2 is an isometric view of the access port of FIG. 1;

FIG. 3 is a partial cross-sectional view of the surgical access device of FIG. 1, showing the insertion device advancing through the access port;

FIG. 4 is a detail view of region 4 in FIG. 3;

FIG. 5 is a partial cross-sectional view of the surgical access device of FIG. 1, showing the insertion effecting extension of the through the access port, the figure also illustrating an initial insertion being made through an abdominal wall by the insertion device;

FIG. 6 is a detail cross-sectional view of the initial insertion of the surgical access device, the figure also illustrating the engagement between the insertion device and access port at the distal end of the surgical access device;

FIG. 14 is a cutaway view of a further embodiment of an access port in accordance with the invention, having inwardly projecting guide fingers for facilitating insertion of surgical instruments through the access port;

FIG. 15 is a partial cross-sectional view of the access port of FIG. 14;

FIG. 16 is a cutaway view of the access port of FIG. 14, shown in an elongated configuration, with an insertion device inserted therein;

FIG. 17 is a cutaway view of a further embodiment of an access port in accordance with the invention, having a valve and a central guide tube for facilitating insertion of surgical instruments through the access port;

FIG. 18 is a partial cross-sectional view taken along line 18-18 of the access port of FIG. 17;

FIG. 19 is a partial cross-sectional view taken along line 18-18 of the access port of FIG. 17, shown in an elongated configuration, having an insertion device inserted therein;

FIG. 20 is a cutaway view of still another embodiment of an access port in accordance with the invention, including a reinforcing backstop for engagement with an insertion device in accordance with the invention;

FIG. 21 is a partial cross-sectional view of the access port of FIG. 20, taken along line 21-21;

FIG. 22 is an isometric view of a surgical access device in accordance with the invention, including the access port of FIG. 20, and an insertion device having a latching mechanism for engaging the access port;

FIG. 23 is an isometric view illustrating the surgical access device of FIG. 22, showing the access port in an elongated configuration in engagement with an insertion device, prepared for insertion through the abdominal wall of a patient;

FIG. 24 is an isometric view of a further embodiment of an access port in accordance with the invention, having a relatively longer neck portion than foregoing embodiments;

FIG. 25 is an isometric view of an additional embodiment of an access port in accordance with the invention, having a tip with flexible anchor elements provided thereon, for securing the tip to the access port body, and optionally for guiding surgical instruments through the lumen of the access port;

FIG. 26 is an isometric view of still another embodiment of an access port in accordance with the invention, having a flange reinforcing element provided thereon;

FIG. 29 is a cross-sectional view taken along line 29-29 of the access port of FIG. 27, shown in a non-elongated configuration;

FIG. 30 is a detail view of region 30 in FIG. 29;

FIG. 31 is a detail view of region 31 in FIG. 29;

FIG. 32 is a cross-sectional view of the access port of FIG. 27, shown in an elongated configuration with an insertion device inserted in the access port;

FIG. 36 is an isometric view of yet another access port in accordance with the invention, having a generally flared configuration in the distal end portion thereof with longitudinal ribs extending the length of the body thereof;

FIG. 37 is a partial cross-sectional view of the access port of FIG. 36;

FIG. 38 is a partial cross-sectional view of the access port of FIG. 36, shown in an elongated configuration with an insertion device inserted in the access port;

FIG. 39 is an isometric view of still another access port in accordance with the invention, having longitudinal ribs in a neck portion and circumferential ribs in the distal end portion thereof;

FIG. 40 is a partial cross-sectional view of the access port of FIG. 39;

FIG. 41 is a partial cross-sectional view of the access port of FIG. 39, shown in an elongated configuration with an insertion device inserted in the access port;

FIG. 42 an isometric view of a further embodiment of access port in accordance with the invention, which access port has an enlarged, generally barb-shaped region and a plurality of barb-shaped ribs to inhibit pullout of the access port from the abdominal wall of a patient;

FIG. 43 is an exploded view of the access port of FIG. 42, illustrating the various components thereof;

FIG. 61 is an isometric view of a further embodiment of a surgical access port having a low-profile for use in conjunction with single-incision surgeries;

FIG. 62 is a cross-sectional view of the surgical access port of FIG. 61, taken along line 62-62 thereof;

FIG. 63 is a close-up view of a distal end portion of the surgical access port of FIG. 61;

DETAILED DESCRIPTION

Figure 7:
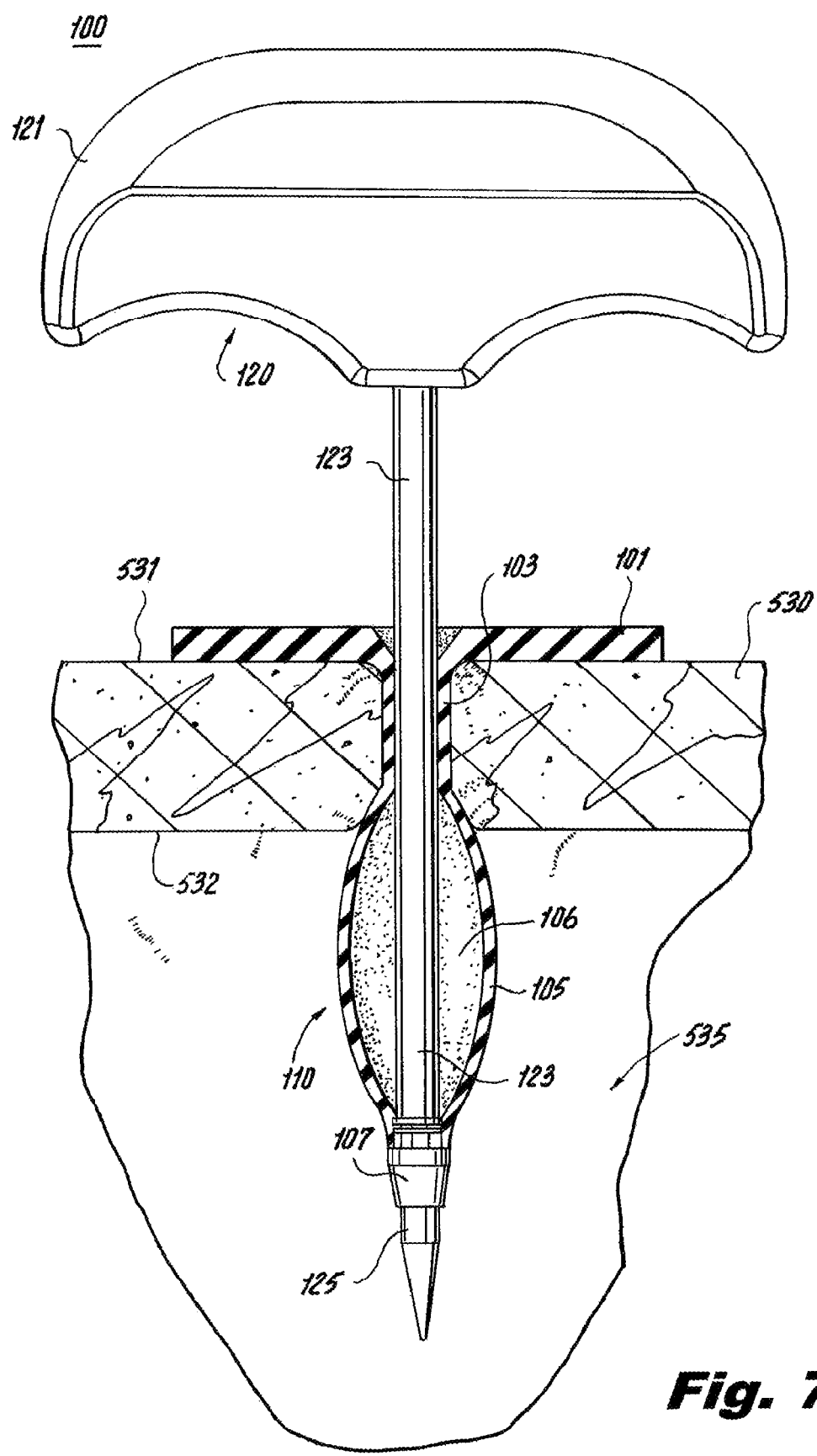
FIG. 7 is a partial cross sectional view illustrating the surgical access device of FIG. 1, inserted through the abdominal wall, with the insertion device partially withdrawn from the access port.

Reference will now be made in detail to the selected embodiments of the invention, examples of which are illustrated in the accompanying drawings. The devices and methods presented herein relate to providing a surgical access port to allow insertion and removal of surgical instruments during a procedure. The present invention is particularly suited for use in minimally-invasive surgical procedures of the abdomen, and is suitable for procedures where the abdominal cavity is pressurized with insufflation gas.

For purpose of explanation and illustration, and not limitation, an isometric view of an exemplary embodiment of a surgical access device in accordance with the invention is shown in FIG. 1 and is designated generally by reference character 100. Other embodiments of surgical access devices in accordance with the invention, or aspects thereof, are provided in FIGS. 2-34, as will be described.

FIGS. 1-9 illustrate the surgical access device 100, and components thereof alone, and in conjunction with an abdominal wall (i.e., 530 of FIGS. 5-9) of a patient, additionally illustrating the steps of insertion and use the surgical access device 100. The surgical access device 100 includes, generally, an access port 110 and an inserter 120. The access port is at least partially flexible in its construction, and depending on the particular embodiment can be primarily composed of one or more flexible materials. The access port includes a body 118, with a proximal flange 101 and distal tip 107 arranged thereon, at opposed ends thereof. The body 118 includes bulb portion 105 and a neck portion 103, each of which defines a respective portion of a lumen 106 passing therethrough. Upon insertion, as will be understood, the bulb portion 105 assists in anchoring the access port 110 into the abdominal wall 530 (e.g., in FIG. 8) of the patient, while the neck portion 103 maintains a passageway through the abdominal wall 530.

The insertion device 120 includes a handle 121 for gripping by a user, a shaft 123, and a distal tip 125. The tip 125 can include an engagement feature, such as the stepped portion illustrated, which engages a mating stepped interior of the distal tip 107 of the access port 110. The insertion device can include a cutting tip at its distal end, or can have a blunt tip at the end thereof. The insertion device 120, therefore, can be a trocar, a blunt-tip obturator, or a visualization device (e.g., an obturator with a visualization tip and a channel to receive an endoscope), for example. The flange 101, serves multiple purposes. Firstly, the flange 101 serves as a location for a user to grip when preparing the access port 110 for insertion. Secondly, the flange 101 acts as a stop to abut the outer surface (skin) of the patient's abdominal wall, preventing the entire access port 110 from passing through the incision made to insert the access port. Further, the flange 101 can be provided with a lead in surface 102, which helps guide the insertion device 120, or other instruments therein and therethrough.

The tip 107 is provided at the distal end of the body 118 of the access port 110. The tip 107 is insert molded, adhered, or otherwise secured to the body 118, details of which are set forth below in connection with other embodiments. Since the tip 107 must securely engage the insertion device 120, the tip 107 is preferably made of a relatively rigid material. However, although illustrated as extending distally from the body 118, the tip can be provided within the body 118, near the distal end thereof, if desired. As such, the tip 107 can be concealed from view, while still having the necessary rigidity to withstand forces exerted by the insertion device 120, for example. Variations of the bulb portion 105, neck portion 103, tip 107 and flange 101 are described below in connection with other embodiments. Naturally, these specific features can be interchanged and combined as needed or desired.

FIG. 4 is a detail view of the respective region of FIG. 3. As can be seen, the lead in surface 102 can facilitate insertion of a surgical instrument. Additionally, an integral O-ring seal 104 is provided, which seals between an instrument shaft (illustrated as insertion device shaft 123), and the access port 110. Thus, egress of insufflation gas is inhibited. Naturally, such feature can be applied to any embodiment set forth herein. Additionally, the precise configuration of the seal 104 can vary, if desired, but the seal 104 can, as illustrated, be a simple projection of the seal 104 from the neck portion 103 of the access port 110. Moreover, a plurality of seals, such as seal 104 can be provided in series to further enhance sealing capability.

As shown in FIGS. 5 and 6, in use, the insertion device 120 is inserted through the lumen 106 of the access port 110, with the tip 125 of the insertion device 120, passing through and engaging the tip 107, preventing proximal movement of the tip 107, relative to the insertion device 120 (FIG. 6). Next, the flange 101 is pulled proximally by the user, toward the handle 121 of the insertion device 120, longitudinally elongating the access port 110, reducing its cross-sectional profile, to facilitate insertion (e.g., in FIG. 5). The access port 110 is maintained in an elongated configuration during insertion, as the surgical access device passes through the abdominal wall 530 of the patient. Because the access port 110 includes a flexible material, the access port 110 can be additionally radially compressed by the abdominal wall during insertion.

The surgical access device 100 is urged through the abdominal wall 530 of the patient until the flange 100 meets the surface 531, or skin of the abdominal wall 530. FIG. 7 illustrates the surgical access device 100 in such a position, with the insertion device 120 slightly withdrawn from the access port 110. As the insertion device is withdrawn, the bulb portion 105, now held within the abdominal cavity 535, reverts toward its original configuration, expanding in diameter. The bulb portion 105, therefore, engages the inside surface 532 of the abdominal wall 530. If the access port 110 is configured in such a way that the neck 103 elongates during insertion, upon release of tension in the access port applied by the insertion device 120, the neck 103 attempts to contract, thereby pulling the bulb portion 105 toward the flange 101, helping secure the access port 110 to the abdominal wall 530. If provided, however, ribs (e.g., ribs 1004 shown in FIG. 10) can inhibit the elongation of the neck 103, allowing the force exerted in longitudinally elongating the access port 110 to be focused on reducing the cross sectional profile of the bulb portion 105. Advantageously, as the bulb reverts to its original configuration with the bulb expanded in diameter, the surgical access port foreshortens, the benefits of which will be described below.

Figure 8:
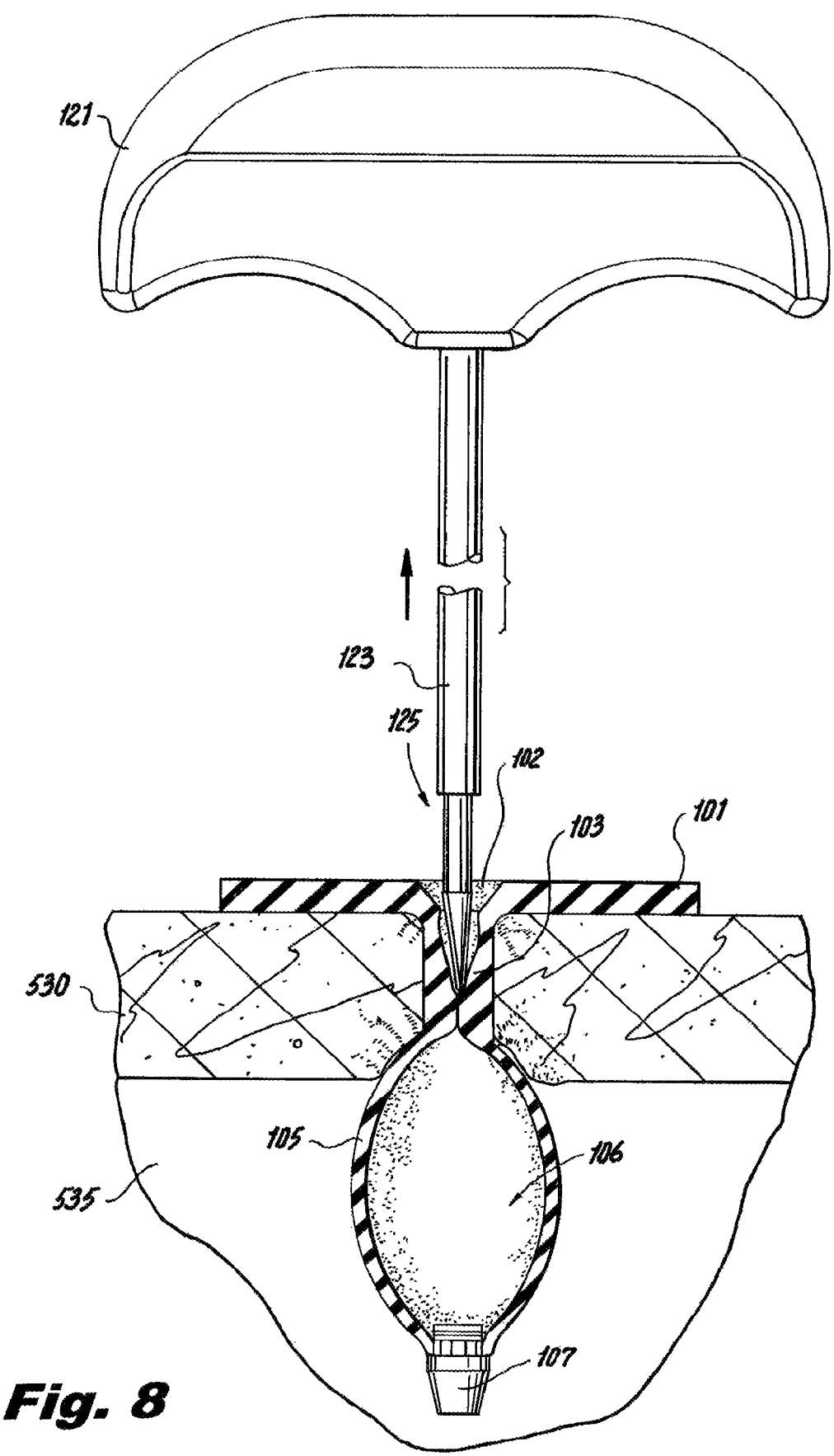
FIG. 8 is a partial cross sectional view illustrating the surgical access device of FIG. 1, inserted through the abdominal wall, with the insertion almost fully withdrawn from the access port.
Figure 9:
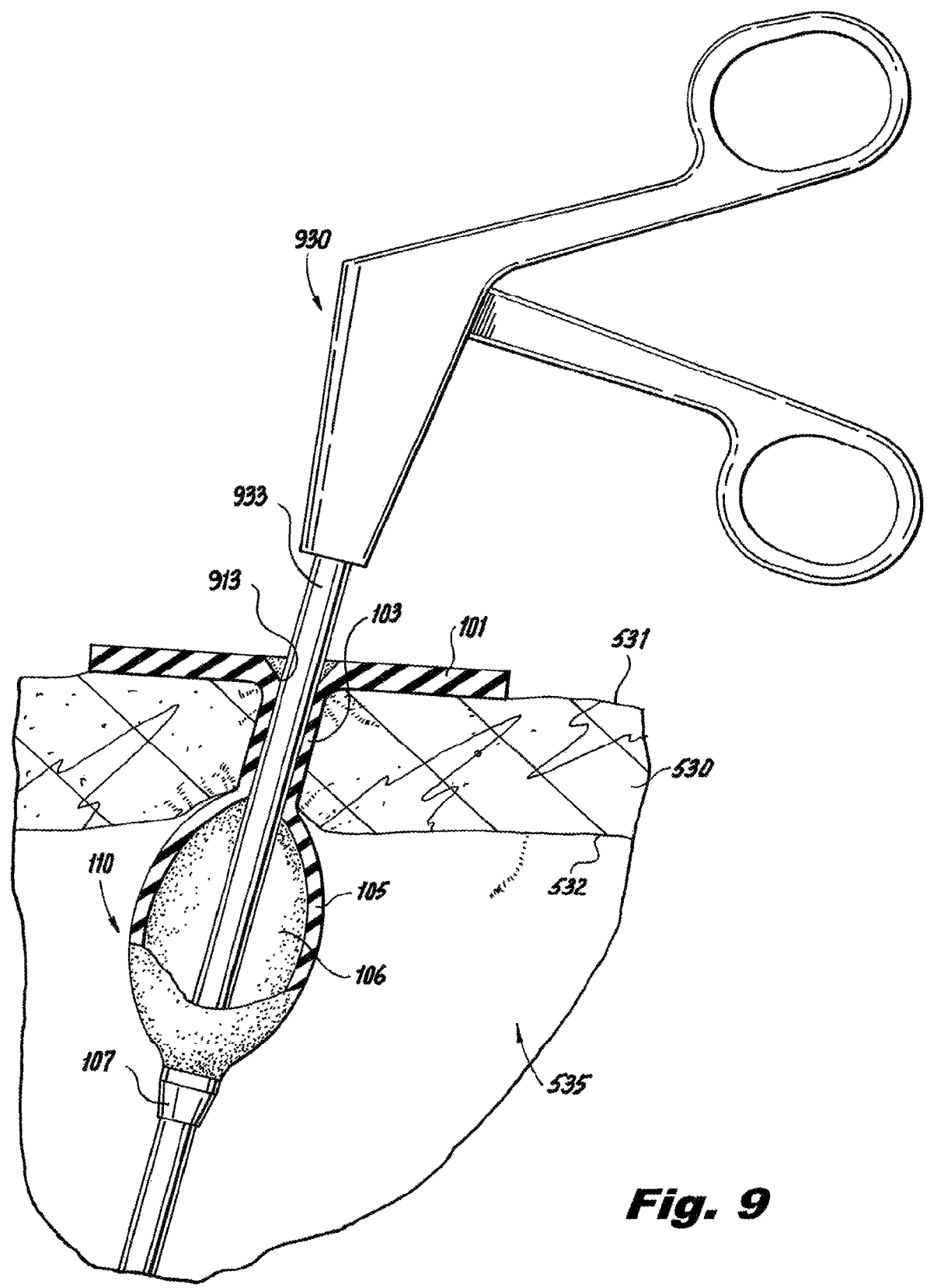
FIG. 9 is a cutaway view the access port of the surgical access device of the preceding figures, illustrating the access port in use, with a surgical instrument inserted therethrough.

FIG. 9 illustrates the access port 100 of FIGS. 1-8, with a surgical instrument 930 inserted therethrough. As illustrated, the flange 101 maintains engagement with the upper and lower surfaces 531, 532 of the abdominal wall 530, even when the access port 110 is manipulated to angle an instrument. Because the surgical access port foreshortens during insertion and is firmly held in place relative to the abdominal wall by the bulb portion 105 and flange 101, the length of the access device interacting with the surgical instrument is minimized and the forces, which must be exerted to angle and manipulate the surgical instrument can therefore be reduced. Further, as can be seen, access ports in accordance with the invention can be sized such that contact is maintained between the interior neck wall 913 and the shaft 933 of the instrument 930, thereby maintaining an airtight seal. Additional seal elements, such as one or more internal ribs, can be arranged circumferentially on the inner wall 913 of the neck 103, if desired. If a plurality of ribs are provided, they can be longitudinally spaced from one another so as to provide even greater sealing.

In this embodiment, upon withdrawal of the instrument 930, the abdominal wall 530, which continually exerts an inward force on the access port 110, causes the lumen 106 in the region of the neck 103 to close, thus sealing the lumen 106, inhibiting escape of insufflation gas from the surgical cavity (e.g., a pneumoperitoneum). Such behavior can be seen, for example, in FIG. 8, illustrating withdrawal of the insertion device 120 from the access port 110. This occurs if the neck portion 103 is configured so as to allow this to happen. For example, the material selection must be such that the neck region is sufficiently compliant, compressible and/or collapsible to be affected by the force of the abdominal wall 530—that is, not excessively rigid. For this reason, it may be desirable to not include longitudinal ribs (e.g., ribs 1004 shown in FIG. 10).

In other instances, however, ribs or other stiffening means may be desirable. As an alternative to ribs, if desired, a material having directional reinforcement can be utilized, such as a fiber-reinforced polymer. As such, the access port 110 can be formed so as to have longitudinal resistance to elongation, for example at the neck 103, while still easily collapsing radially, so as to seal between the access port and a surgical instrument.

It should be noted, that if the neck 103 of the access port 110 is configured so as to be relatively compliant, the neck can adapt to different sizes of surgical instruments inserted therethrough—expanding to the appropriate size to accommodate each tool.

FIGS. 10-13 illustrate an alternate embodiment of a surgical access device in accordance with the invention, designated generally by reference number 1000, which access device 1000 includes an insertion device 1020 and access port 1010. The access port 1010 is similar to the access port 110 of FIGS. 1-9 in many respects. However, in this embodiment, the bulb portion 1005 is more spherical than that of access port 110, which itself is somewhat more elongate in shape. Naturally, the precise shape can be tailored as seen appropriate. The more spherical shape of the bulb portion 1005 of the access port 1010 of FIGS. 10-13 is particularly advantageous in areas where reduced clearance is present, such as, for example, along lateral sides of the abdominal cavity. In the medial portion of the abdominal cavity, particularly if the abdominal cavity is insufflated, more space is available than is available in the lateral regions of the abdominal cavity. The shortened shape of the bulb portion 1005, allows placement of the access port 1010, and allows manipulation of the access port 1010 and tools inserted therethrough, within the cavity.

Additionally, elongation-prevention ribs 1004 are provided on the neck 1003. As evident, particularly from the cross-sectional view of FIG. 12, the increased cross-sectional area of the neck 1003 affords increased resistance to the applied tension needed to elongate the access port 1010 prior to insertion, while not substantially affecting the ability of the neck 1003 to contract or expand radially. As mentioned briefly above, all or a portion of the access port 1010 can be composed of one or more materials having directional properties. For example, the neck 1003 can be provided with reinforcing fibers embedded within the material thereof. Such fibers can be as rigid as desired, to impart the desired properties on the access port.

Alternatively or additionally, the bulb 1005 or flange 1001 can similarly include materials having directional properties. If, for example, the bulb 1005 is reinforced or is otherwise composed of material(s) having directional properties, when tension is applied to the access port 1010 the bulb 1005 will simply deform to a point, elongating as a whole, but without the material itself elongating or "stretching." Thus, it can therefore be understood that elongation or "stretching" of the material itself used for this and other access ports described herein, is not essential to practice of the invention.

Figure 10:
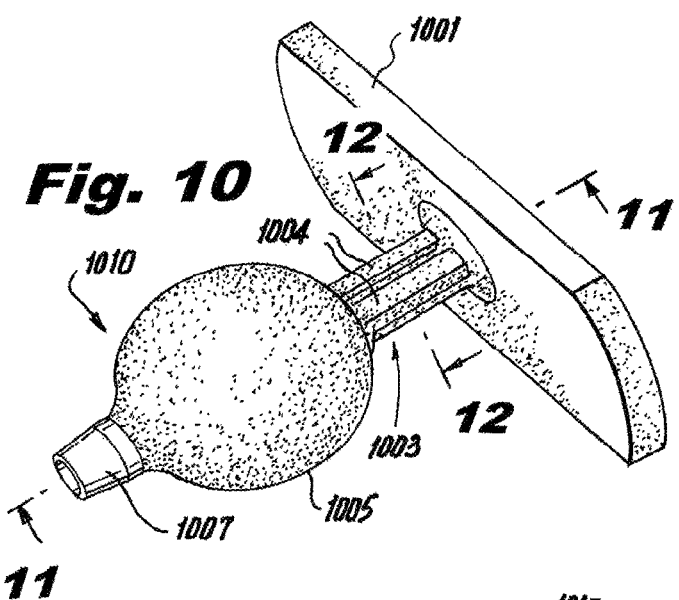
FIG. 10 is an isometric view of another embodiment of an access port of a surgical access device in accordance with the invention, having longitudinal ribs on a neck portion thereof.
Figure 11:
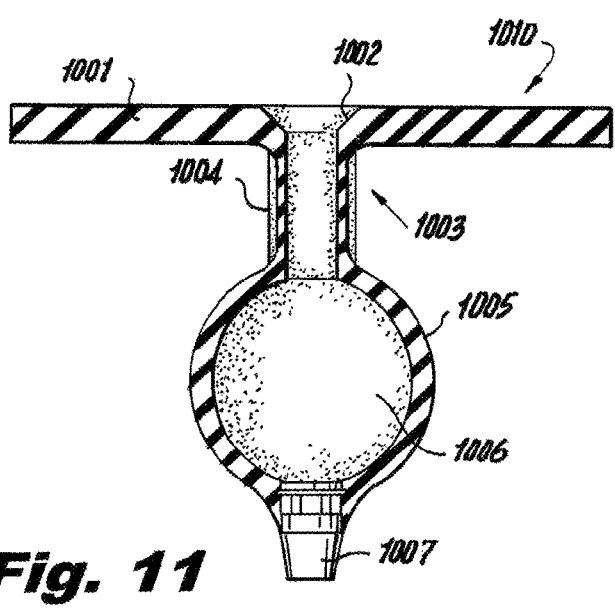
FIG. 11 is a partial cross-sectional view of the access port of FIG. 10, taken along line 11-11 of FIG. 10.
Figure 12:
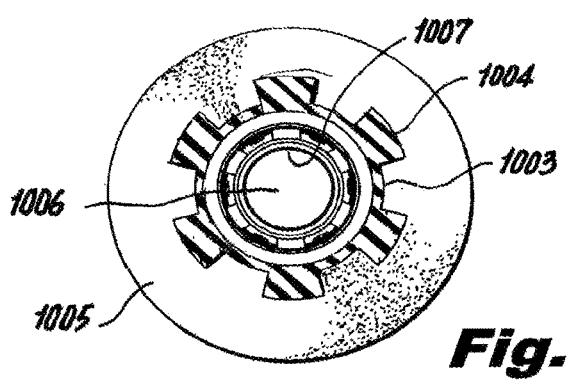
FIG. 12 is a cross-sectional view of the access port of the access port of FIG. 10, taken along line 12-12 of FIG. 10.
Figure 13:
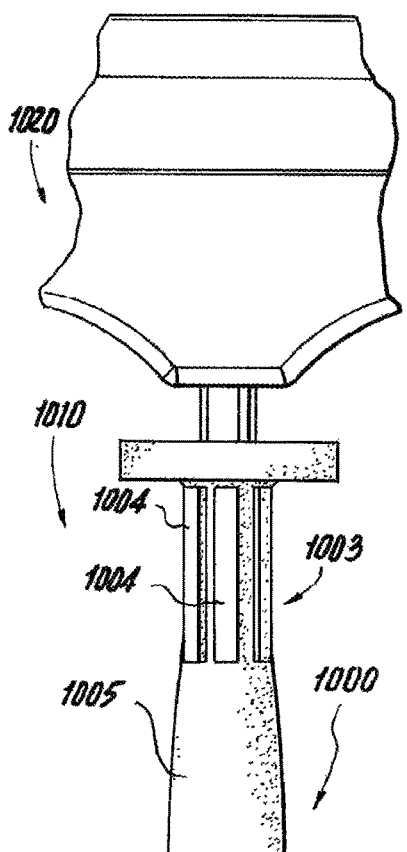
FIG. 13 is a cutaway view of the access port of FIG. 10, shown in an elongated configuration, with an insertion device inserted therein.
Figure 27:
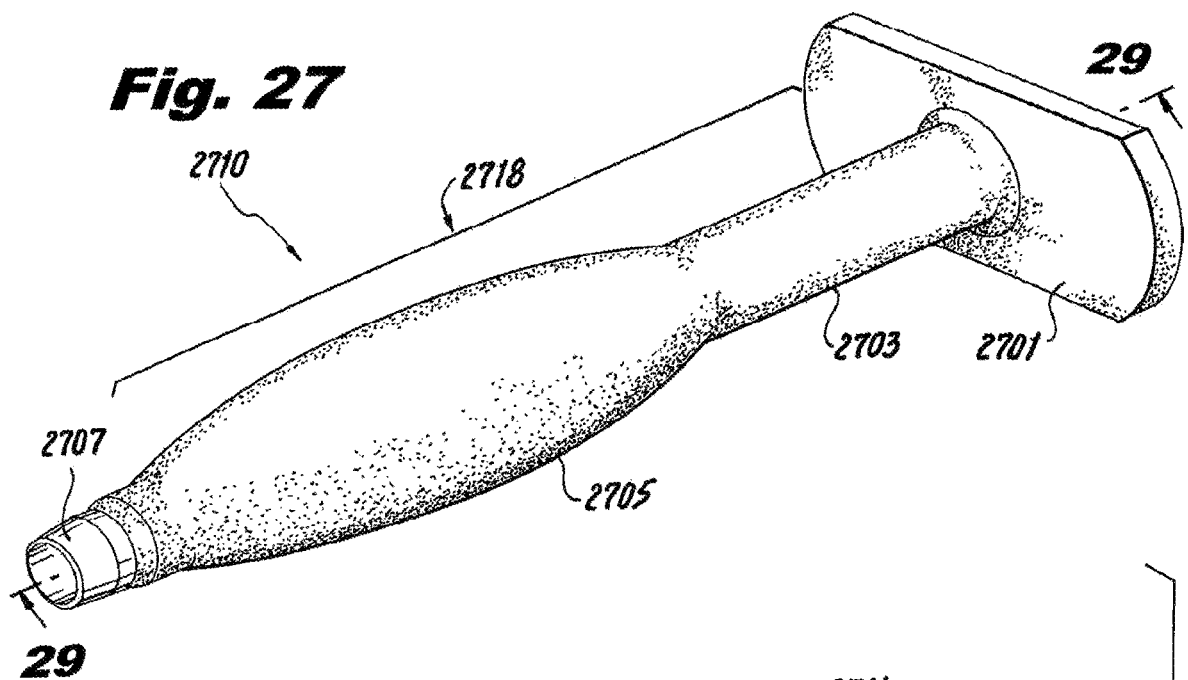
FIG. 27 is an isometric view of another embodiment of an access port in accordance with the invention, having a guide tube, valve and flange reinforcing element.
Figure 28:
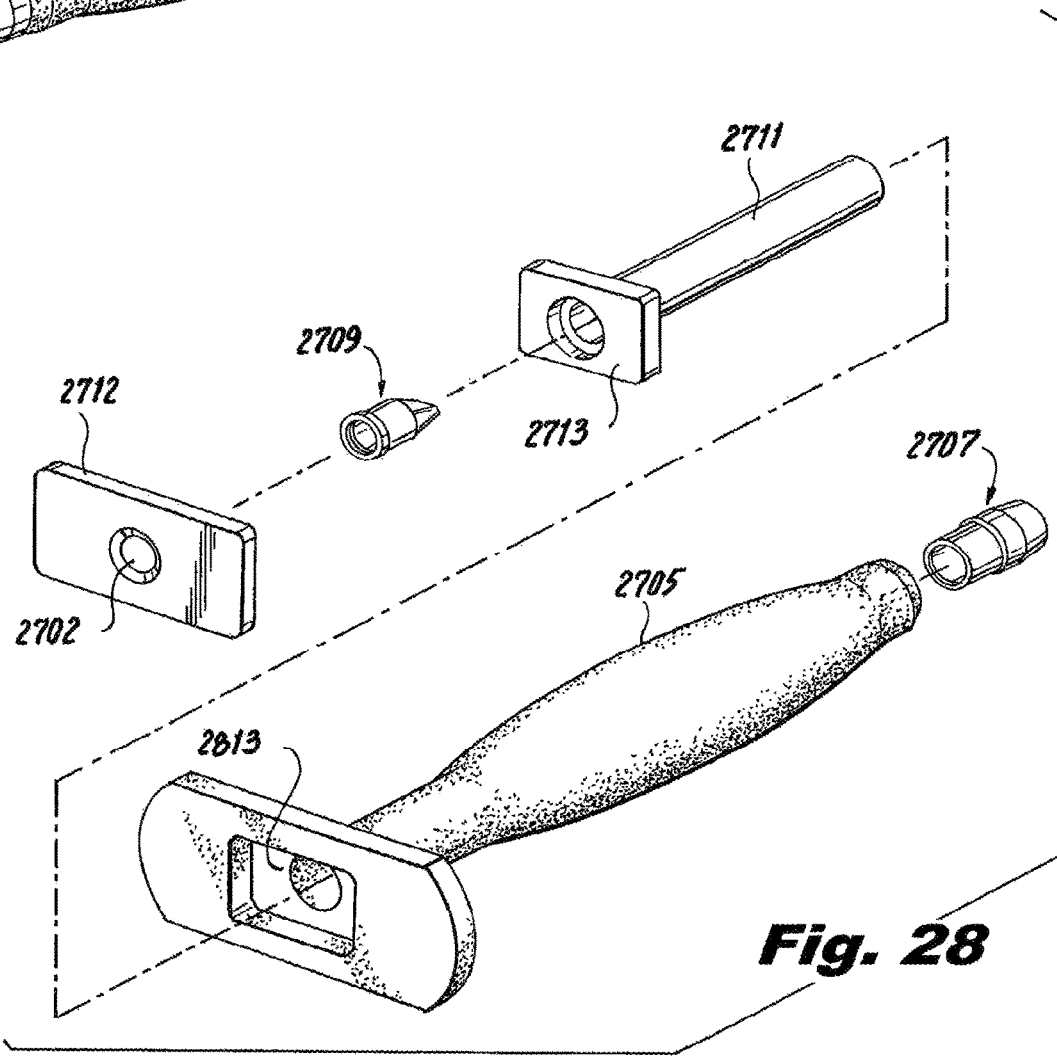
FIG. 28 is an exploded view of the access port of FIG. 27.

FIG. 12 is a cross-sectional view taken across the neck 1003 of the access port 101 of FIG. 10. The ribs 1004 of the neck 1003 are evident thereon, and the tip 1007 can be seen though the lumen 1006 of the access port 1010. FIG. 13 illustrates the access port 1010 of FIG. 10 in an elongated configuration. As can be seen, the relatively spherical shape of the bulb portion 1005 does not yield an access port 1010 that is incapable of assuming a low-profile shape.

FIGS. 14-16 illustrate a further embodiment of an access port 1410 in accordance with the invention. The general shape of the access port 1410 is similar to that of the access port 1010 of FIGS. 10-13. The access port 1410 includes a flange 1501 with a lead-in surface 1502, a body 1518 having a neck portion 1503 with longitudinal ribs 1504, and a bulb portion 1505. A distal tip 1507 is also provided thereon for engaging an insertion device.

However, the access port 1410, and more specifically the tip 1507, includes axially inwardly and radially outwardly directed flexible fingers 1508, which are provided to line the distal end portion of the lumen 1506, defined within the bulb portion 1505. The fingers 1508 serve to guide surgical instruments toward the lumen of the tip 1507, so as to more easily pass through the access port 1410 and into surgical cavity. While the access port body 1518 (i.e., the bulb 1505 and the neck 1503) may be made of a material that is relatively soft to allow flexure, the fingers 1508 and additionally the tip 1507 itself can be made of a relatively rigid material. Such material preferably also has a relatively low coefficient of friction against materials used in surgical instruments (e.g., metals and plastics), so that the instruments are easily guided through the lumen and into the surgical cavity.

The fingers 1508 also serve to reinforce the distal end portion of the bulb portion 1505, if they are embodied such that they are at least partially secured to the bulb 1505. Alternatively, they can simply be in contact with the inner surface 1506 of the bulb 1505, resiliently contacting the surface 1506. In the illustrated embodiment, particularly as seen in FIG. 15, the fingers 1508 each include a longitudinal, inwardly projecting portion 1519, extending from the tip 1507. The longitudinal portion 1519 is connected to a second, angled portion 1517 at a resilient hinge 1520, the geometry of which is configured to maintain the angled portion 1517 of each finger 1508 in abutment with the interior surface 1506 of the bulb portion 1505, if the fingers 1508 are not already secured thereto. The hinge 1520 can be a so-called living hinge, defined in the material of the finger 1508 by a reduced thickness region, for example. Alternatively, the fingers 1508 and hinges 1520 can simply be made of material that is flexible enough to bend during elongation of the access port 1410.

With reference to FIG. 16, it can be seen that when the access port 1410 is elongated to result in a reduced cross-sectional profile prior to insertion, the fingers 1508 flex in conjunction with the bulb 1505. The relative dimensions of the fingers 1508 can be selected as desired. For example, the fingers can widen toward their distal ends (distal with respect to the tip 1507), in order to better guide instruments through the lumen 1506. When in the elongated state, as shown in FIG. 16, such widened fingers can lay adjacently to one another, or can be configured to overlap one another. As such, the fingers cover an increased area, while the access port 1410 is in a first configuration (FIGS. 14, 15), and still allow the elongated, reduced profile configuration of FIG. 16.

With reference to FIGS. 17-19, a further embodiment of an access port 1710 in accordance with the invention is provided. The access port 1710 includes a proximal flange 1701, a neck 1703 having longitudinal ribs 1704, and a bulb portion 1705 terminating in a distal tip 1707. The distal tip 1707 is attached to the bulb 1705 in this embodiment by extensions 1709, which provide a location for the material of the bulb 1705 to engage the tip 1707. Such engagement can be effected, for example, by way of insert molding the tip 1707 with the material of the body (i.e., the bulb 1705 and neck 1703). In the case of the flange 1701, as with other flanges set forth herein in connection with other embodiments, the flange 1701 can be molded integrally with the neck 1703 and bulb 1705 portions.

The access port 1710 of FIGS. 17-19 differs from the forgoing embodiments in that the access port 1710 includes a guide tube 1711 and a valve 1709 provided in the lumen 1706 thereof. The guide tube is provided with a proximal flange 1819, which rests in a recess formed in the flange 1701 of the access port 1710. The flange 1819 of the guide tube 1711 maintains the tube 1711 in place, and can be insert molded, adhered or otherwise attached to the access port body. The tube 1711 serves as a guide during insertion of surgical instruments, helping lead the instruments toward the tip 1707, reducing the chances that such instruments will veer toward the inner wall 1706 of the bulb 1705, which might delay the surgical procedure being performed. The guide tube 1711 is also preferably made out of material having a relatively low coefficient of friction, with respect to the surgical instruments being inserted therethrough, in order to further facilitate insertion of surgical instruments.

The valve 1709, is shown as a duckbill type valve, but can be of any type desired. Alternatively or additionally, a ball valve and/or or a fluid seal can be utilized, as set forth, for example in U.S. patent application Ser. No. 11/517,929 filed Sep. 8, 2006, which is incorporated herein by reference in its entirety. The valve 1709 is arranged within the guide tube 1711 and serves to reduce leakage of insufflation gas from the surgical cavity (e.g., a pneumoperitoneum), when instruments are removed from the access port 1710. While certain of the foregoing embodiments, such as the access port 110 of FIGS. 1-9, seal upon removal of an instrument due to the compressive forces exerted by the abdominal wall, the guide tube 1711, which is relatively rigid, prevents this embodiment from sealing in that manner. Accordingly, the valve 1709 is provided to seal when an instrument is removed from the access port 1710.

FIGS. 20-23 illustrate a surgical access device, including an access port 2010 and an insertion device 2220. The access port 2010 is similar in many respects to the foregoing access ports, with the exception of a reinforcing backstop 2012 provided on the underside of the flange 2001. The backstop 2012 rigidifies the flange 2001, and provides a secure surface for engagement with locking pawls 2223a, 2223b of the insertion device 2220. The pawls 2223a, 2223b are preferably resiliently biased toward a closed position, where protrusions 2225 at the distal end thereof engage the backstop 2012, inhibiting removal of the insertion device 2220 from the access port 2010. A user can disengage the pawls 2223a, 2223b by depressing the release end 2224 of the pawls 2223a, 2223b, which pivot the protrusions 2225 away from the access port 2010 and the backstop 2012.

While the above-described latching mechanism can be incorporated into any of the embodiments set forth herein, the access port 2010 illustrated includes a flange 2001, which holds the backstop 2012, a neck 2003 having longitudinal ribs 2004, a bulb portion 2005, and a tip 2007, secured to the bulb portion 2005 with extensions 2008.

In use, the user places the insertion device 2220 through the lumen 2006 of the access port 2010, elongating the access port 2010 until the pawls 2223a, 2223b engage the backstop 2012 (See FIG. 23). The access device is then inserted through the abdominal wall of the patient. The user then depresses the release ends 2224 of the pawls 2223a, 2223b, and withdraws the insertion device 2220 from the access port 2010, allowing the access port 2010 to revert toward its original configuration (as in FIG. 20, for example). The access port may deviate slightly from its original configuration when inserted because of the forces acting on the access port 2010. However, it is to be understood that the configuration of the access port 2010 prior to elongation is very similar to that of the access port 2010 when inserted through the abdominal wall.

FIGS. 24-26 illustrate further embodiments of access ports 2410, 2510 and 2610 in accordance with the invention, each of which includes an extended neck portion 2403. The extended neck portion 2403 can be particularly advantageous when the access ports 2410, 2510 and 2610 are used in a patient having a relatively thick layer of abdominal fat, or an otherwise thick abdominal wall. The access port 2410 of FIG. 24 is substantially similar to many of the foregoing embodiments, with the exception of the elongated neck portion 2403. A proximal flange 2401 is connected to the elongated neck 2403, which in-turn includes longitudinal ribs 2404. The bulb 2405 extends from the neck portion 2403 and terminates in the distal tip 2407, which is connected thereto via extensions 2408.

The access port 2510 of FIG. 25 differs from that of FIG. 24, in the connection between the tip 2507 and the bulb portion 2505. While the construction of the flange 2401, neck portion 2403, and ribs 2404 is identical to that of the access port 2410 of FIG. 24, the tip 2507 includes anchor elements 2508, which extend into and are at least partially embedded into the material of the bulb 2505. The anchor elements 2508 include a longitudinal, inwardly oriented spine 2519 and one or more transverse protrusions 2518, which are embedded into the wall of the bulb 2505. The spine 2519, if desired, can be embedded within the bulb 2505, or can be arranged such that it is exposed to the lumen 2406 of the access port to aid passage of surgical instruments through the access port 2510.

The access port 2610 of FIG. 26 includes a configuration having an identical bulb 2505, tip 2507 and anchor elements 2508 to those of the embodiment of FIG. 25. Similarly, the neck 2403 is identical to each of the embodiments of FIGS. 24 and 25. The access port 2610 of FIG. 26 includes a rigid flange reinforcement 2612 arranged at the proximal end of the access port 2610. The flange reinforcement 2612 is provided, and in this case, recessed into the flange 2601 to impart increased rigidity to the flange 2601. While the flange 2601 can be integrally formed, e.g., molded, with the neck 2403 and bulb 2505 without such reinforcement 2612, such material may be undesirably soft to alone provide adequate rigidity for the flange 2601, because the flange 2601 must be pulled by a user when preparing the access port 2610 for insertion.

FIGS. 27-31 illustrate an access port 2710 in accordance with the invention composed of a plurality of components. As with the access port 1710 of FIGS. 17-19, the access port 2710 includes a guide tube 2711, a valve 2709, and a body 2718, which in-turn includes a flange 2701, neck 2703, bulb 2705, and terminates in a tip 2707. The valve 2709 resides within the guide tube 2711, which in-turn is inserted into the body 2718 of the access port 2710. A proximal flange 2713 of the guide tube 2711 is received by a recess 2813 defined in the flange 2701 of the access port body 2718.

The access port 2710 additionally includes a flange reinforcement 2712, having a lead in surface 2702 to help guide insertion of surgical instruments. As with the access port 2610 of FIG. 26, the flange reinforcement 2712 imparts additional rigidity to the flange 2701. The flange reinforcement 2712 can be applied to the proximal surface of the flange 2701, or partially or fully recessed therein, as in the access port 2610 of FIG. 26. The individual components can be mutually secured by way of any suitable means, including, but not limited to heat welding, ultrasonic welding, solvent welding, adhesive, cohesive or, if desired, mechanical interlocking features. FIG. 31, which is a detail view of the respective portion of FIG. 29, illustrates an intermediate bonding material 3140, which can be an adhesive, for example. In a preferred embodiment, the bonding material 3140 is a material that melts upon application of heat energy, thereby mutually bonding the components of the access port 2710. As best seen in FIG. 30, which is a detail view of the respective region of FIG. 29, the tip 2707 includes an interior step 3009, which engages a mating component on the tip 125 of the insertion device (e.g., see FIG. 32). As can be seen, FIG. 29 illustrates the access port 2710 in a first configuration, prior to insertion through the abdominal wall, and FIG. 32 illustrates the access port 2710 in a second configuration, prepared for insertion through the abdominal wall of the patient.

Figure 33:
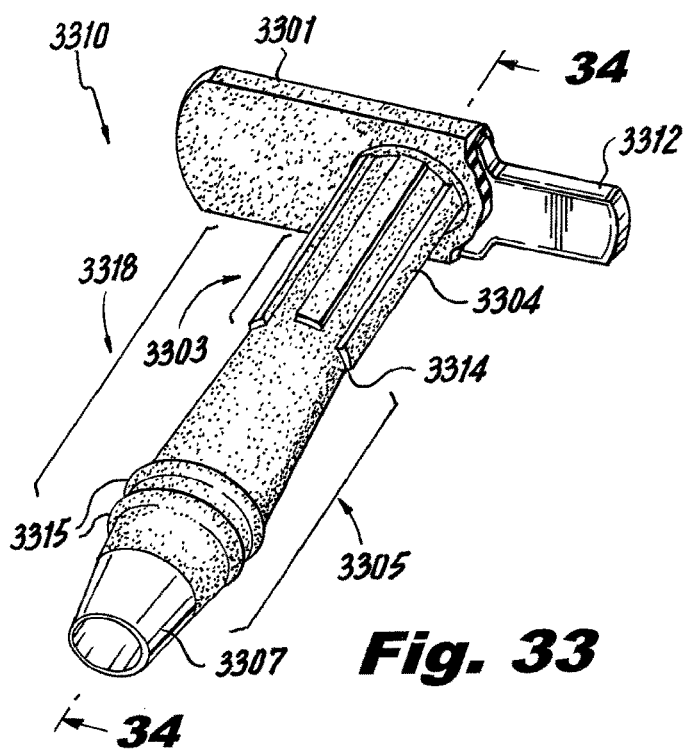
FIG. 33 is an isometric view of a further embodiment of an access port in accordance with the invention, having a generally flared configuration in the distal end portion thereof and circumferential ribs arranged thereon.

FIG. 33 is an isometric view of a further embodiment of an access port 3310 in accordance with the invention, having a generally flared configuration in the distal end portion of the body 3318. The flared region constitutes a bulb 3305, in that the expanded diameter of this region generally resembles such a configuration, and acts to anchor the access port 3310 in the abdominal wall of the patient. The access port 3310 includes a proximal flange 3301, with a flange reinforcing element 3312 arranged thereon, and a distal tip 3307 connected by the body 3318. Longitudinal ribs 3304 are formed on the neck portion 3303, and include a distal taper 3314 so that the ribs gradually approach the contour of the bulb portion 3305, as the diameter of the body 3318 increases toward the distal end of the access port 3310.

Circumferential ribs 3315 further increase the diameter of the bulb portion 3305, providing additional anchoring capability. While the foregoing embodiments can be made from elastomeric materials or non-elastomeric materials, this embodiment preferably includes a material having a predetermined degree of elasticity, particularly because the relative diameter of the bulb portion 3305 to the remainder of the body 3318 of the access port 3310 is not as great as in many of the foregoing embodiments. Accordingly, when elongated, the material of the access port 3310 will stretch, and while the bulb 3305 decreases in profile, the ribs 3315, which are part of the bulb 3305, will also stretch longitudinally, effecting a reduction in their cross-sectional profile.

Figure 34:
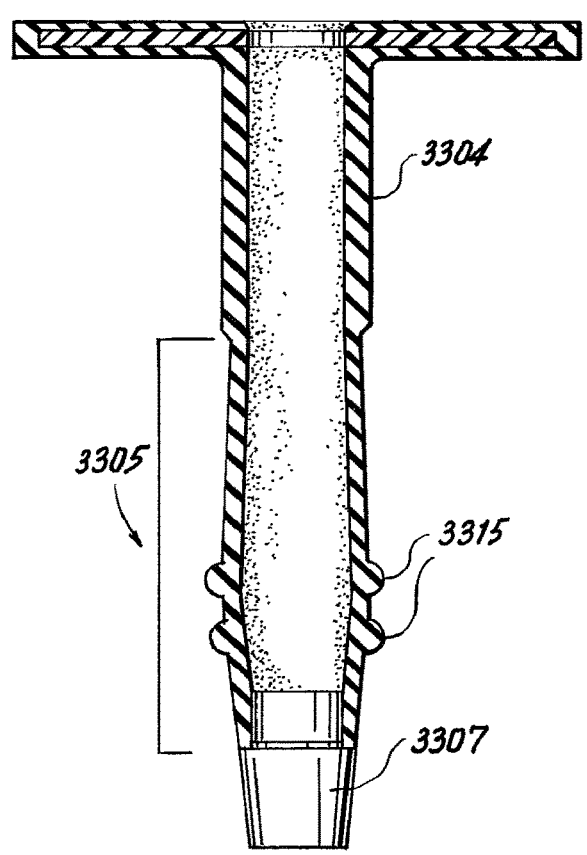
FIG. 34 is a partial cross-sectional view of the access port of FIG. 33.
Figure 35:
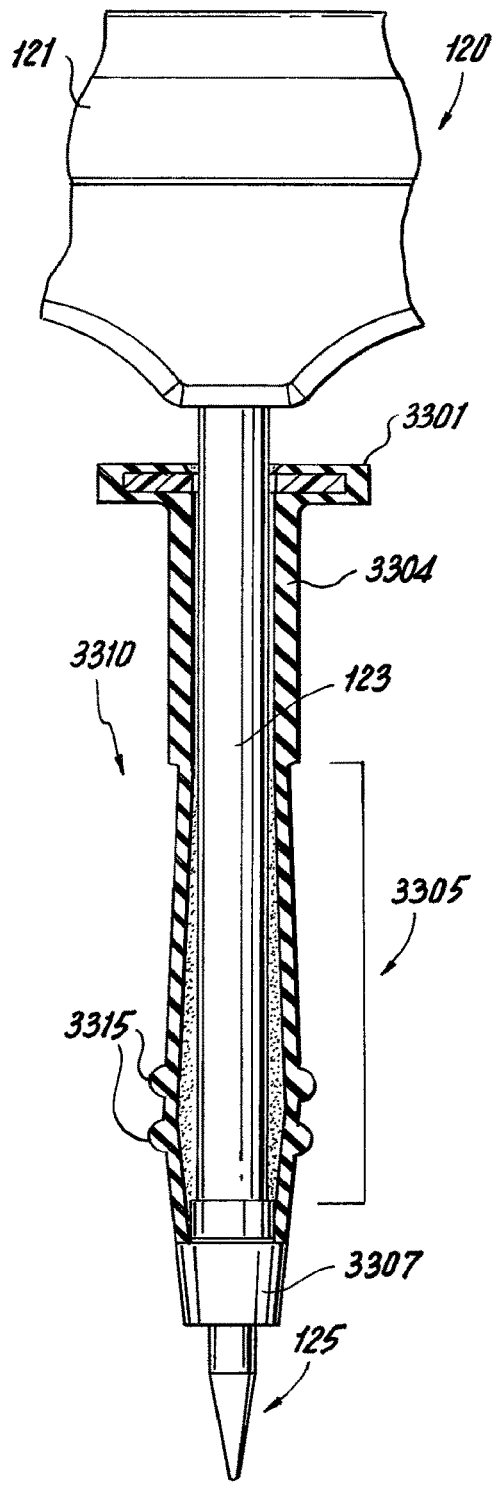
FIG. 35 is a partial cross-sectional view of the access port of FIG. 33, shown in an elongated configuration with an insertion device inserted in the access port.
Figure 44:
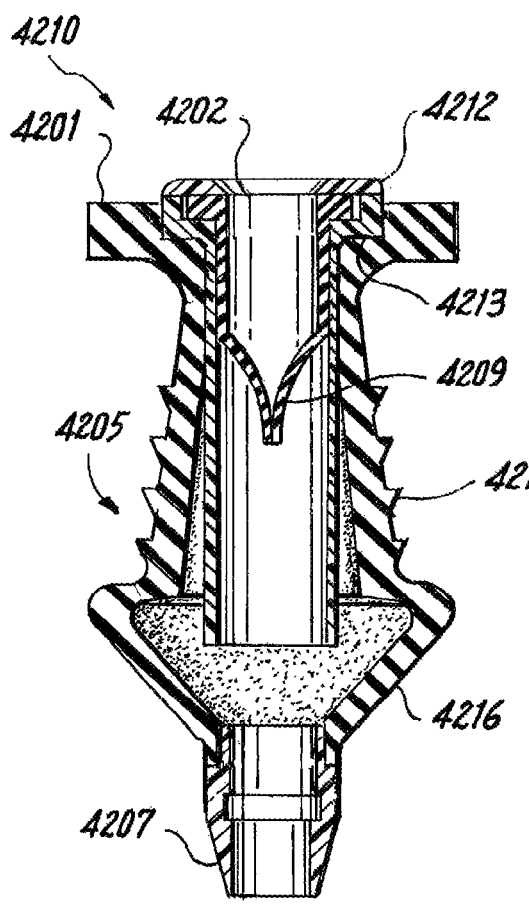
FIG. 44 is a side view of the access port of FIG. 42, illustrating in hidden line the arrangement of internal components thereof.
Figure 45:
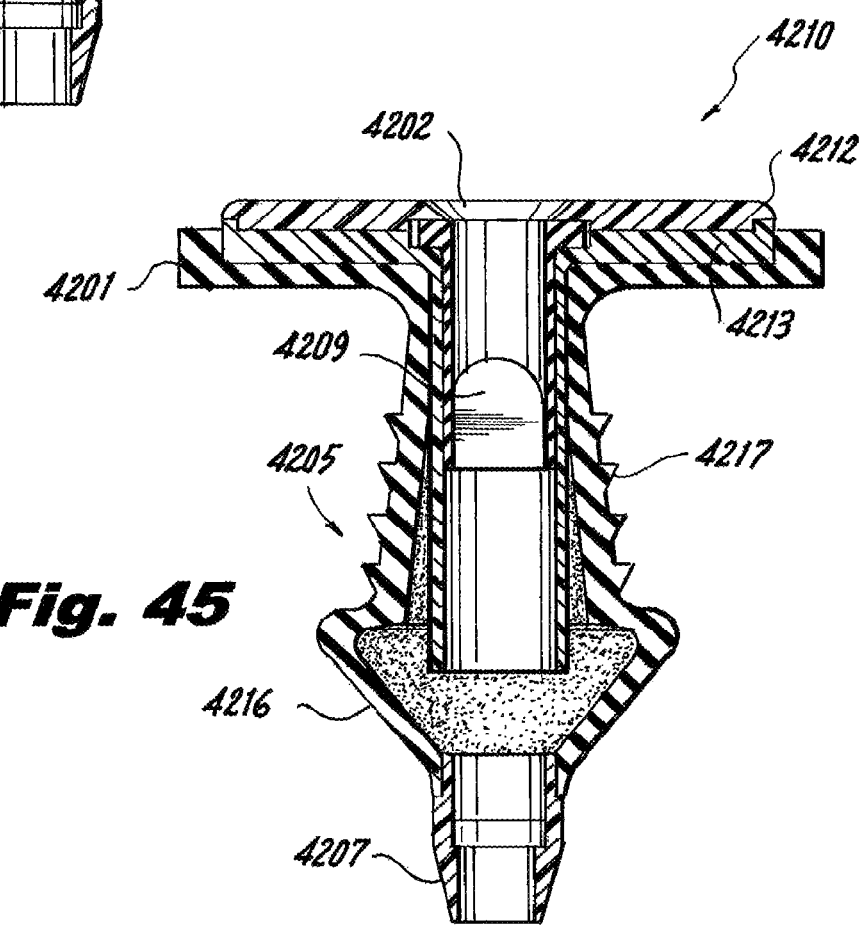
FIG. 45 is a front view of the access port of FIG. 42, also illustrating in hidden line the arrangement of internal components thereof.
Figure 46:
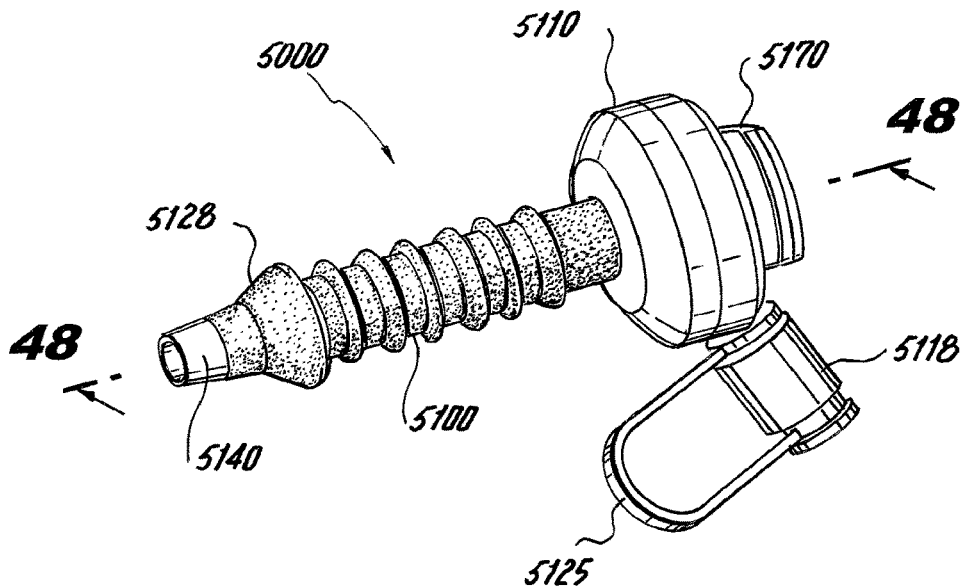
FIG. 46 is a perspective view of another embodiment of the elastomeric surgical access device of the subject invention, shown in a relaxed or unstretched condition in which the anchoring bulb has a first diameter and a first length.
Figure 47:
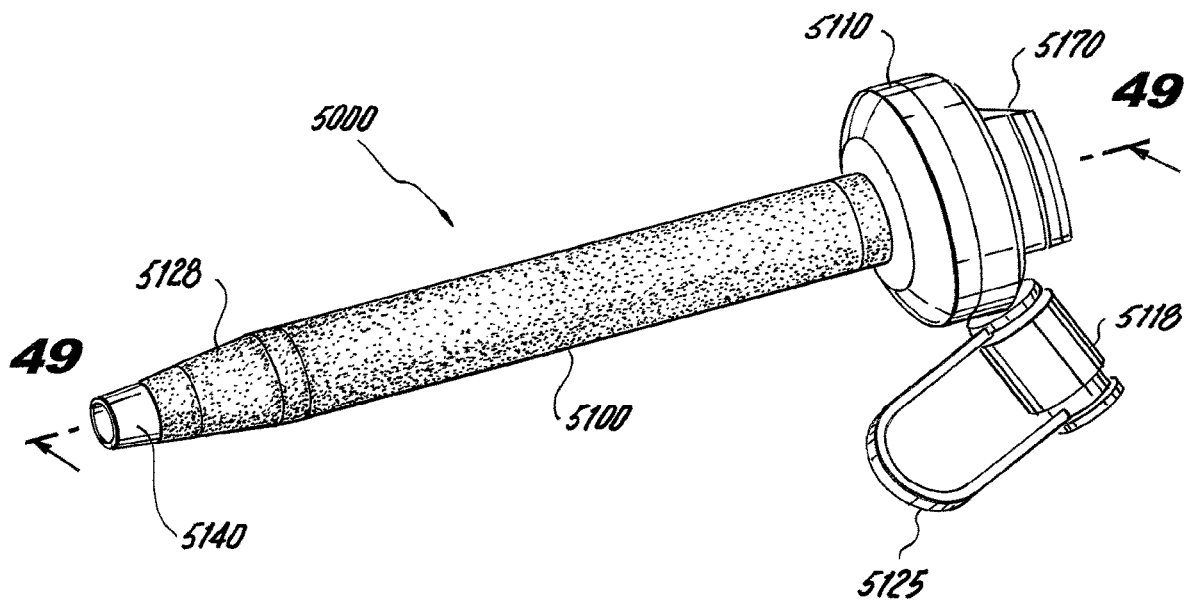
FIG. 47 is a perspective view of the elastomeric surgical access device of FIG. 46, shown in an elongated or stretched condition in which the anchoring bulb has a second diameter less than the first diameter and a second length greater than the first length.

FIG. 34 is a partial cross-sectional view of the access port of FIG. 33 and FIG. 35 is a partial cross-sectional view of the access port 3310 of FIG. 33, shown in an elongated configuration with an insertion device 120 inserted in the access port.

FIG. 36 is an isometric view of a further embodiment of an access port 3610 in accordance with the invention, also having a generally flared configuration in the distal end portion of the body 3618. The flared region constitutes a bulb 3605, which serves to anchor the access port 3610 in the abdominal wall of the patient. The access port 3610 includes a proximal flange 3301, with a flange reinforcing element 3312 arranged thereon, and a distal tip 3607, joined via the body 3618, as with the foregoing embodiment of FIG. 33. Longitudinal ribs 3604 are formed on the body 3618, which extend along the length thereof. The ribs 3604 include an increased height portion 3614 toward the distal end thereof, superimposed at an increased diameter portion of the body 3618. This embodiment also preferably includes a material having at least some degree of elasticity. Accordingly, when elongated, the material of the access port 3610 will stretch, with the bulb 3605 and ribs 3604 decreasing in profile.

FIG. 37 is a partial cross-sectional view of the access port of FIG. 36 and FIG. 38 is a partial cross-sectional view of the access port of FIG. 36, shown in an elongated configuration with an insertion device 120 inserted in the access port 3610.

FIG. 39 is an isometric view of still another access port 3910 constructed in accordance with the invention, having longitudinal ribs 3904 in a neck portion 3903 and circumferential ribs 3915 in the distal bulb portion 3905 thereof. A tip 3907 is also provided, which is connected to the flange 3301 and reinforcing member 3312 by the body 3918 of the access port 3910. The ribs 3904 in the neck portion 3903 serve the purpose of preventing excessive elongation of the neck portion, when preparing the access port 3910 for insertion. The circumferential ribs 3915 in the bulb portion 3905 serve to resist unintended pullout of the access port 3910 from the abdominal wall of the patient. Therefore, it should be noted that as used herein, the term "bulb" refers to a region of expanded diameter, but which does not necessarily resemble a "bulb" shape. Accordingly, when elongated, the material of the access port 3910 will stretch, and while the bulb 3905 decreases in profile, the ribs 3915, which are part of the bulb portion 3905, will also stretch longitudinally, effecting a reduction in their cross-sectional profile, thereby facilitating insertion of the access port 3910 into the abdominal wall of the patient.

FIG. 40 is a partial cross-sectional view of the access port 3910 of FIG. 39, and FIG. 41 is a partial cross-sectional view of the access port 3910 of FIG. 39, shown in an elongated configuration with an insertion device 120 inserted in the access port.

FIGS. 42-45 illustrate an access port 4210 in accordance with the invention composed of a plurality of components, similar to the access port 2710 of FIGS. 27-31. The access port 4210 includes a guide tube 4211, a valve 4209, and a body 4218, which in-turn includes a flange 4201, neck 4203, bulb 4205, and terminates in a tip 4207. The valve 4209 resides within the guide tube 4211, which in-turn resides in the body 4218 of the access port 4210. A proximal flange 4213 (FIGS. 43-45) of the guide tube 4211 resides in a recess defined in the flange 4201 of the access port 4210.

The access port 4210 further includes a flange reinforcement 4212, having a lead in surface 4202 to help guide insertion of surgical instruments therethrough. As with other access ports set forth herein, the flange reinforcement 4212 helps impart rigidity to the flange 4201. The flange reinforcement 4212 can be applied to the proximal surface of the flange 4201, or partially or fully recessed therein.

In this embodiment, as best seen in the exploded view of FIG. 43, for example, the proximal flange 4213 of the guide tube 4211 is relatively large, and in combination with the enlarged flange reinforcement 4212, secures the valve 4209 to the body 4218 of the access port 4210 by engaging the valve 4209 therebetween.

As also can be seen in FIGS. 42-45, the bulb 4205 includes a single distal enlarged portion 4216, having an angled, generally barbed shape, and a plurality of ribs 4217 arranged along the length of the body 4218, which also have a generally barbed shape. Such shape, due to the angled contours thereof, enables relatively easy insertion, while still resisting pullout of the access port 4210 from the patient's abdominal wall.

As with foregoing embodiments, the individual components of the access port 4210 can be mutually secured by way of any suitable means, including, but not limited to heat welding, ultrasonic welding, solvent welding, adhesive, cohesive or, if desired, mechanical interlocking elements.

In order to remove an access port in accordance with the invention from the body of a patient, one can pull the proximal flange (e.g., flange 101 of FIG. 8) away from the abdominal wall. The counteracting force exerted by the abdominal wall will cause the surgical access port, and particularly the bulb portion (e.g., bulb 105 of FIG. 8) to elongate for removal from the body cavity into which it was inserted. Alternatively, in order to remove the port, the insertion device, or a similar blunt-tipped tool for engaging the distal end portion of the access port, can be inserted into the access port to elongate the access port for removal. The latter method, however, may be preferred in order to minimize trauma to the abdominal wall of the patient.

Referring now to FIGS. 46 through 49, there is illustrated another embodiment of the surgical access device of the subject invention, which is designated generally by reference numeral 5000. Access device 5000 is functionally similar to the previously described access devices in that it is adapted and configured to transition between a relaxed or unstretched condition shown in FIGS. 46 and 48 and an elongated or stretched condition shown in FIGS. 47 and 49, facilitated by a unique insertion device shown in FIG. 50. The construction of access device 5000 differs from the previously described access devices in certain respects, as described in more detail hereinbelow.

Figure 48:
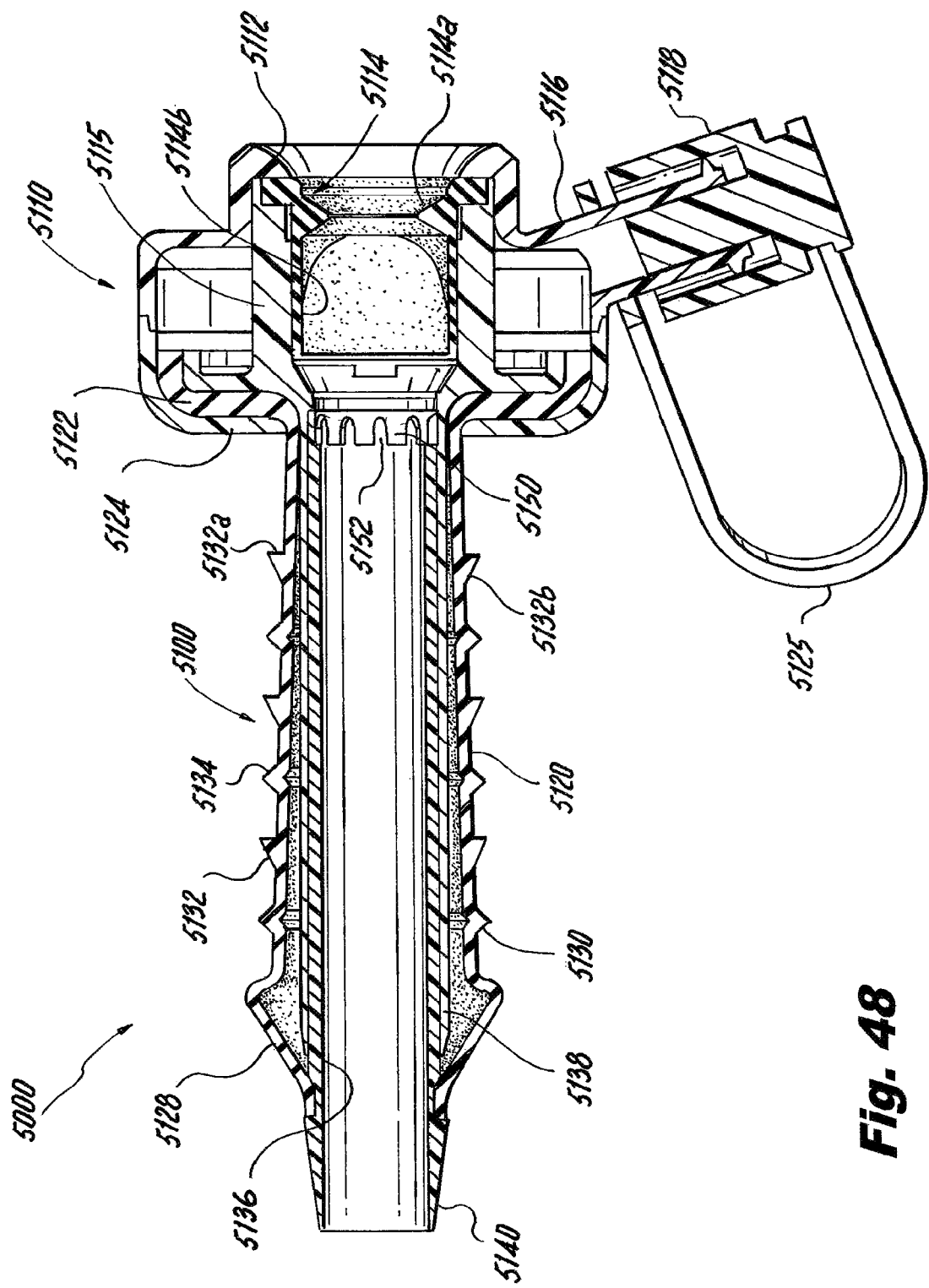
FIG. 48 is a cross-sectional view of the elastomeric surgical access device of the subject invention taken along line 48-48 of FIG. 46.
Figure 49:
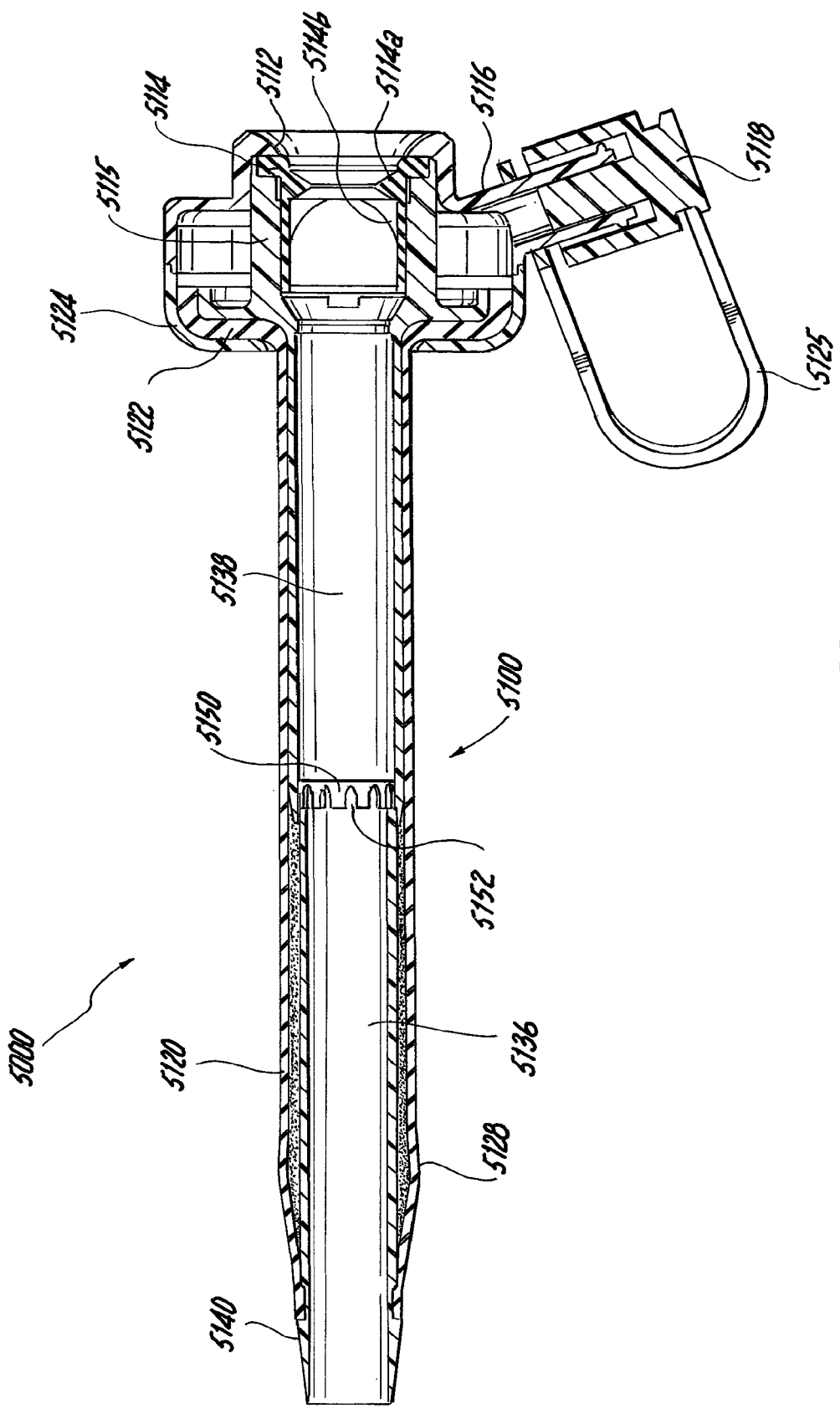
FIG. 49 is a cross-sectional view of the elastomeric surgical access device of the subject invention taken along line 49-49 of FIG. 47.

Access device 5000 includes an elongated body portion 5100 and a proximal seal housing 5110. Seal housing 5110 has a funnel shaped opening 5112 for receiving a trocar or surgical device and in interior cylindrical chamber 5115 for supporting a sealing member 5114 (see FIG. 48). As best seen in FIGS. 48-49, seal member 5114 is a one-piece seal assembly that includes a proximal seal section 5114a in the form of a wiper seal and a distal valve seal section 5114b in the form of a duckbill seal. The duckbill seal may be a single plane valve as shown or a double plane valve having two intersecting duckbills.

The seal housing 5110 of access device 5000 also includes a tubular insufflation port 5116 for mating with a source of pressurized fluid by way of a luer lock fitting or a similar type of connective arrangement known in the medical arts. The insufflation port 5116 of proximal seal housing 5110 includes a removable cap 5118 that is connected to the seal housing 5110 by a living hinge 5125 so that the cap 5118 does not become displaced during a surgical procedure and can be easily reused.

The body portion 5100 of access device 5000 includes an axially extendable elastomeric sheath 5120 defining a pathway for permitting minimally invasive access to the abdominal cavity of a patient by a surgical device. The elastomeric sheath 5120 has a generally radially outwardly tapering cross-sectional configuration, in its unstretched condition, shown in FIG. 48. The proximal end portion of the sheath 5120 has a flange section 5122 of increased thickness (relative to the body portion of the sheath) that is secured to the proximal housing 5110 by an underplate 5124. A radially enlarged anchoring bulb 5128 is formed adjacent the distal end of sheath 5120 for securing the access device 5000 against the interior wall of the abdominal cavity, once it has been deployed.

The elastomeric sheath 5120 of access device 5000 includes a plurality of axially spaced apart annular retaining ribs 5130. More particularly, the sheath 5120 includes two types of alternating ribs 5130, including a first type 5132 that has a horizontal ledge 5132a and an angularly inclined riser 5132b and a second type 5134 that has a generally V-shaped cross-section. The ledged ribs 5132 prevent movement of the sheath 5120 in a proximal direction during use, as does the V-shaped ribs 5134, although to a lesser extent. The V-shaped ribs 5134 differ from the ledged ribs 5132 in that they have the same wall thickness as the sheath 5120 itself, and thus more easily flatten out when the sheath 5120 is stretched during deployment, thereby reducing insertion resistance, as best seen in FIG. 48.

Access device 5000 further includes telescoping guide tubes that include an inner tube 5136 and an outer tube 5138. Together, the telescoping guide tubes 5136, 5138 define a passage for a trocar during deployment of the access device 5000 and a pathway for the introduction of surgical instruments. The proximal end of the outer tube 5138 is preferably integrally formed with the proximal housing portion 5110 of access device 5000. However, it is envisioned that the outer guide tube 5138 could be separate from and secured to the housing portion 5110. The distal end of the inner tube 5136 extends from the distal end of sheath 5120 and defines a tapered nosepiece 5140 for the access device 5000. The nosepiece 5140 provides a smooth transition surface to the radially enlarged anchoring bulb 5128.

Figure 50:
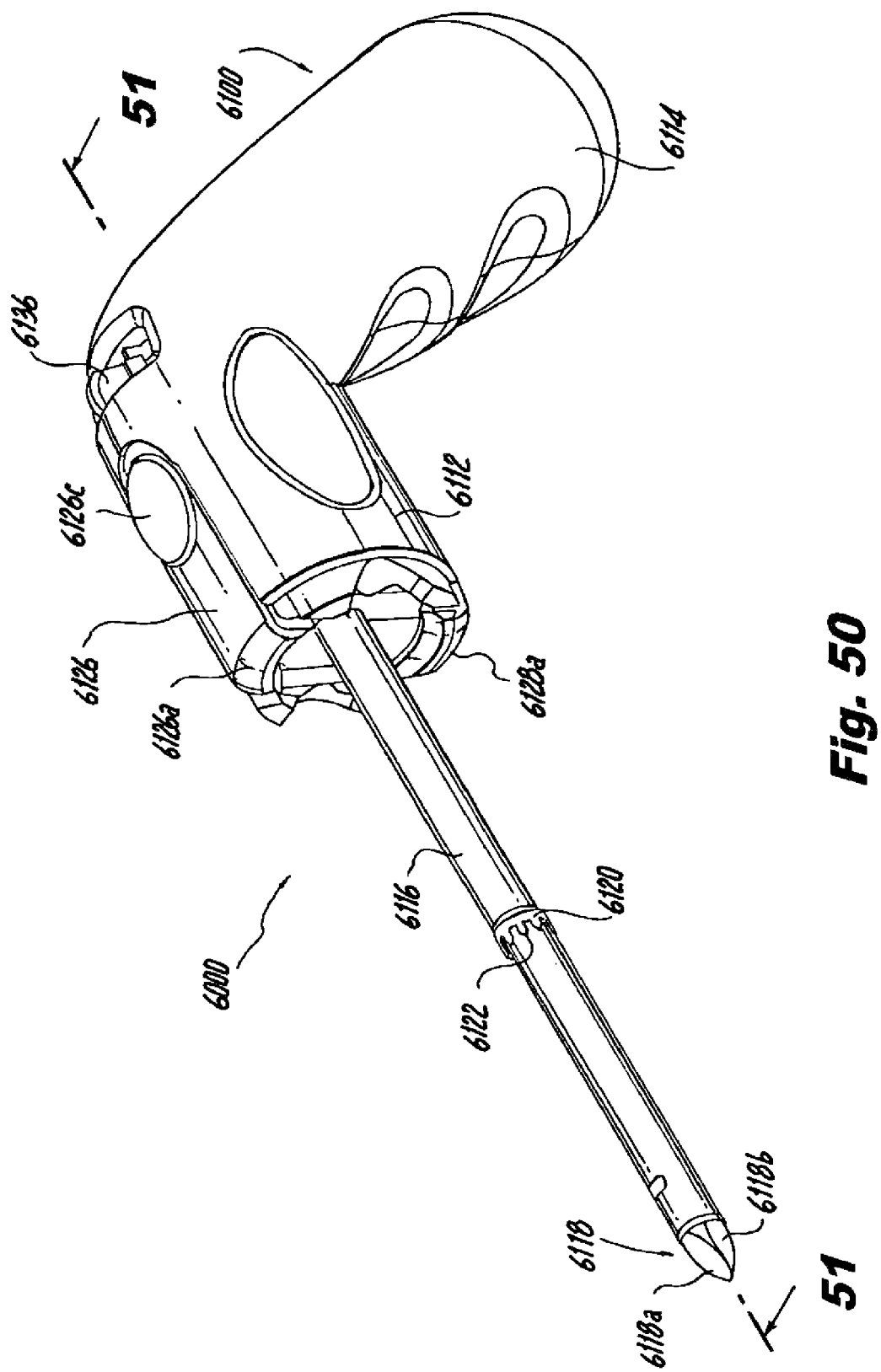
FIG. 50 is a perspective view of an insert device designed to deploy the elastomeric surgical access device of FIG. 46, which includes a handle assembly and a longitudinally extending trocar having a tissue-piercing tip.
Figure 51:
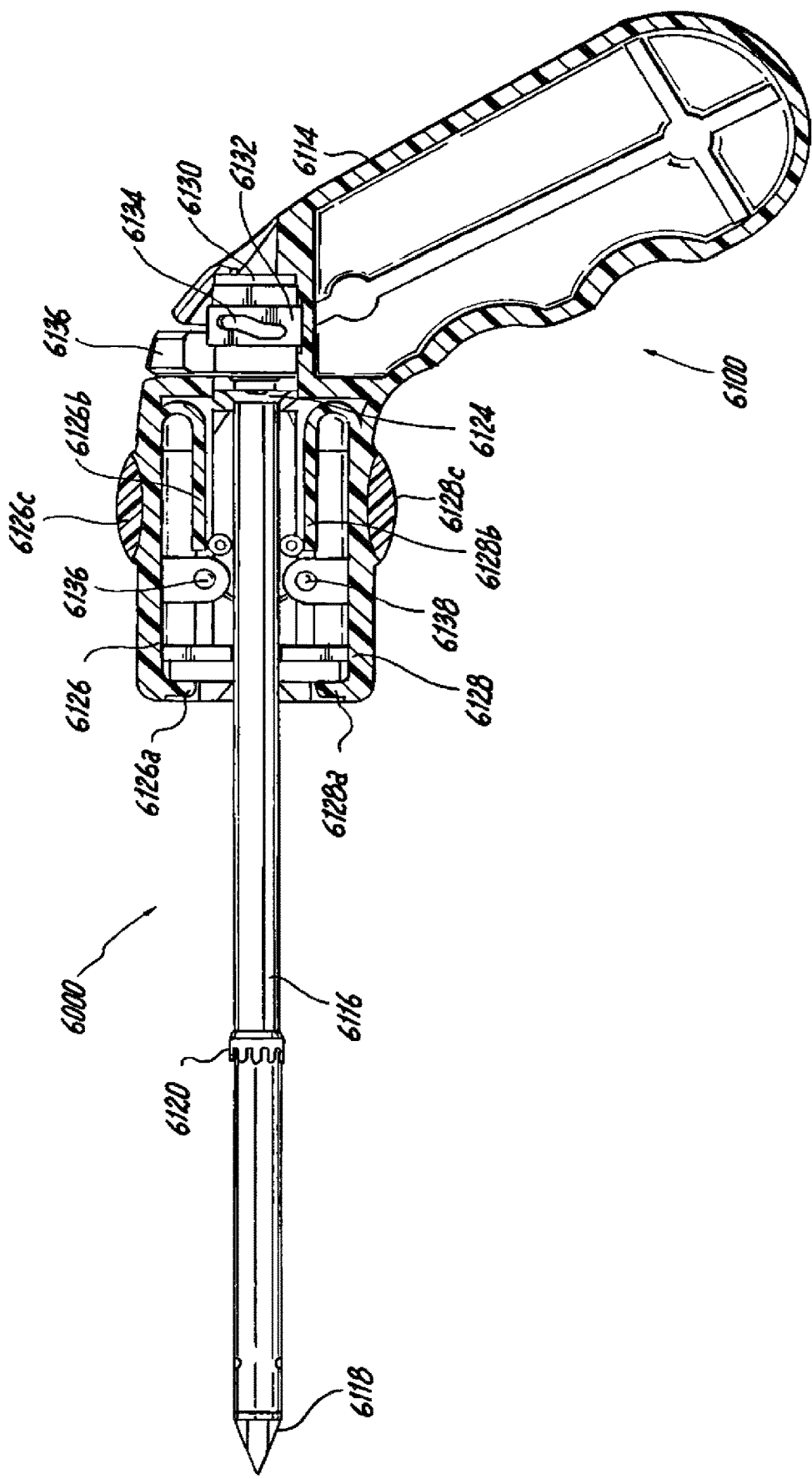
FIG. 51 is cross-sectional view of the insert device of the subject invention taken along line 51-51 of FIG. 50.
Figure 52:
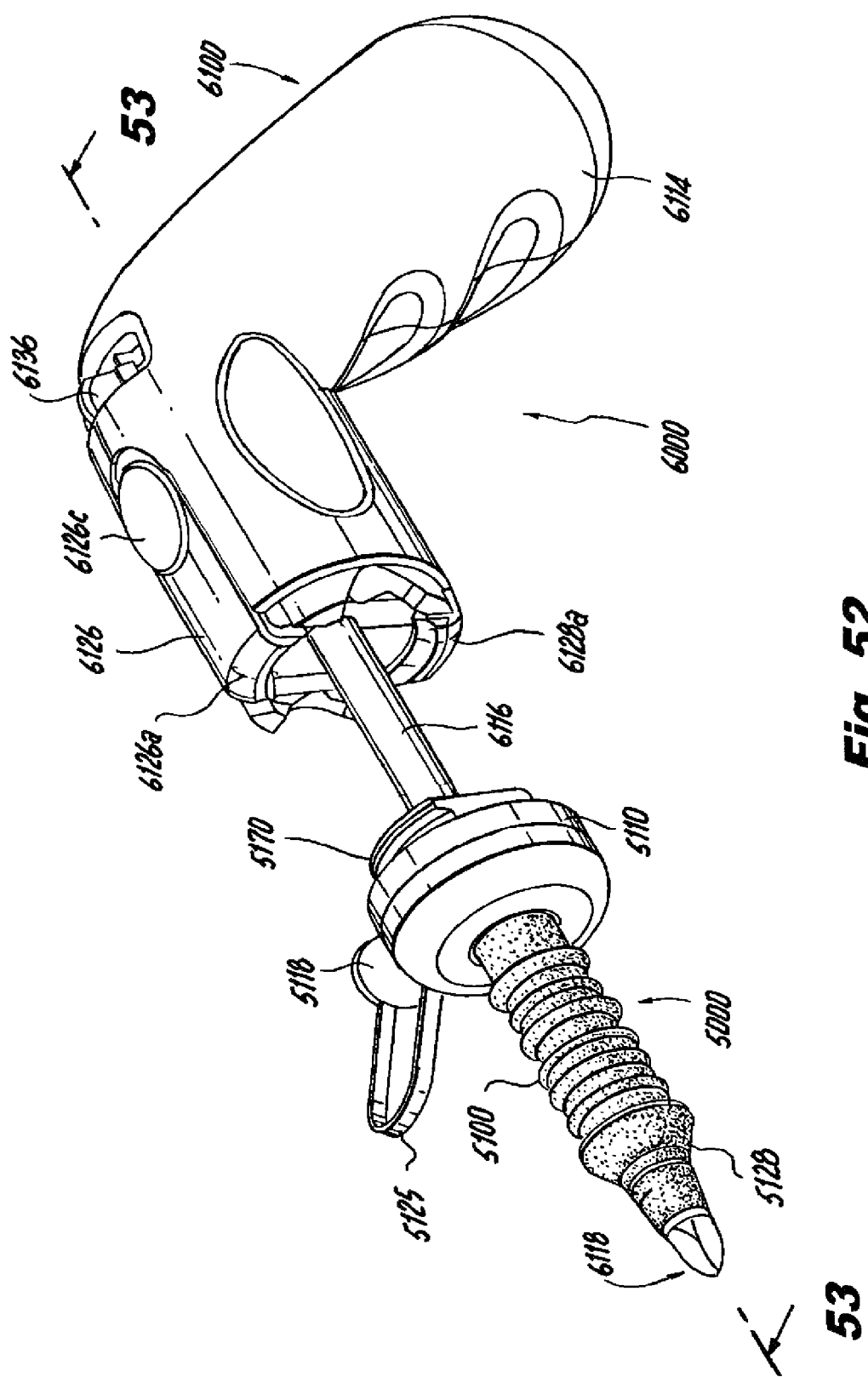
FIG. 52 is a perspective view of the insert device of FIG. 50 together with the surgical access device of FIG. 46 in an unstretched condition.
Figure 54:
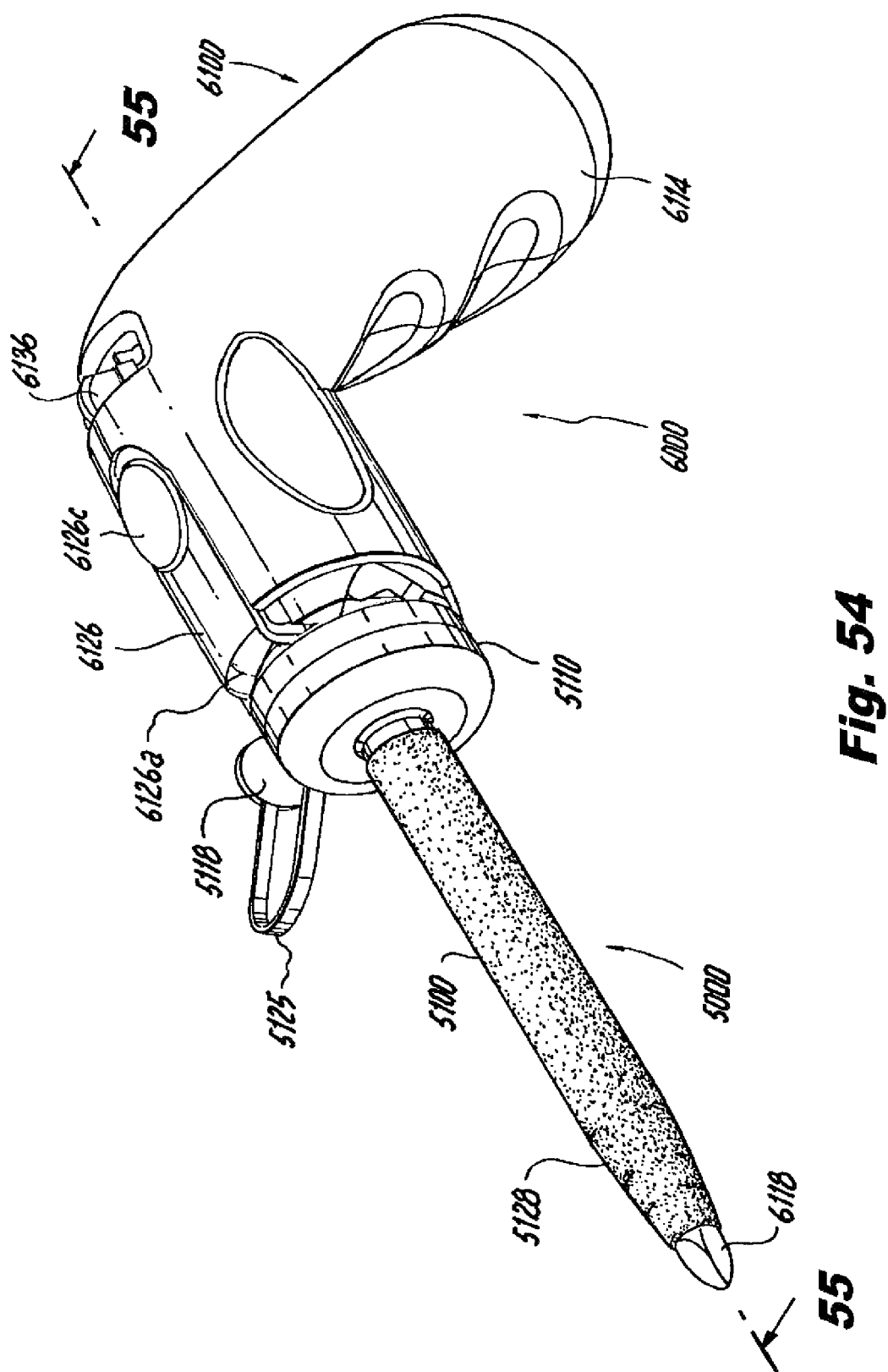
FIG. 54 is a perspective view of the insert device of FIG. 50 together with the surgical access device of FIG. 46 in an elongated stretched condition.

As discussed above and throughout this specification, an insertion device is utilized to effectuate the transition of the access device 5000 between the unstretched and stretched conditions shown in FIGS. 52 and 54, respectively. An embodiment of the insertion device of the subject invention is illustrated in FIGS. 50 and 51, and is designated generally by reference numeral 6000. Together, the insertion device 6000 and the access device 5000 form a cooperative system for gaining ready access to the abdominal cavity of a patient in order to perform a laparoscopic surgical procedure.

Insertion device 6000 includes a proximal handle assembly 6100 that includes a barrel section 6112 and depending ergonomically shaped grip section 6114. An elongated trocar shaft 6116 extends distally from the barrel section 6112 of handle assembly 6100. The distal tip 6118 of trocar shaft 6116 is preferably adapted and configured to pierce through tissue, including the abdominal wall, and thus includes at least two cutting facets 6118a, 6118b.

Figure 55:
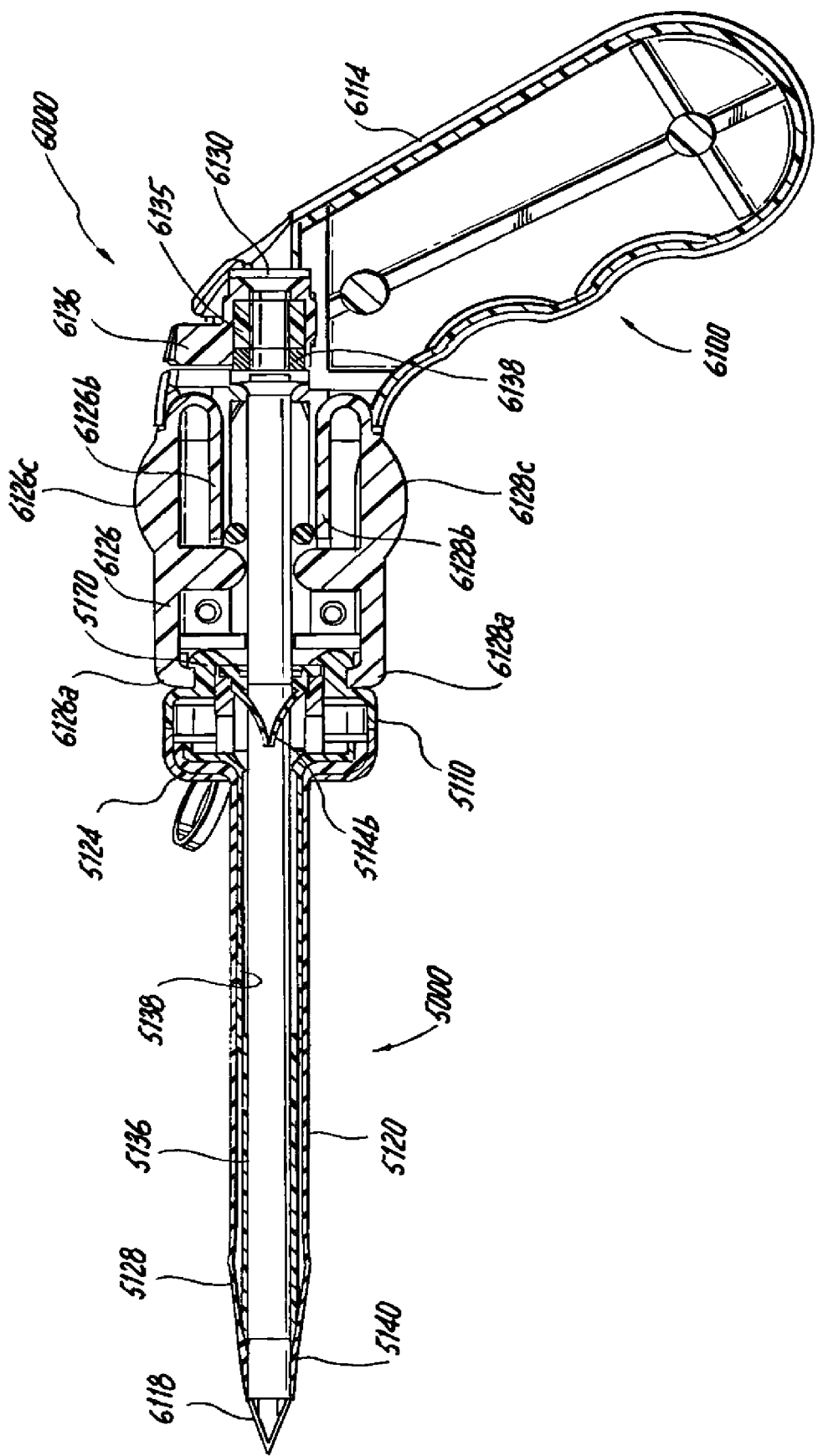
FIG. 55 is cross-sectional view taken along line 55-55 of FIG. 54 showing the insert device of FIG. 50 together with the surgical access device of FIG. 46 in an elongated stretched condition.

It is also envisioned and well within the scope of the subject disclosure, that trocar shaft 6116 can be configured as an optical trocar assembly for purposes of visualizing the penetration into the abdominal cavity. Thus, the distal tissue-piercing tip 6118 of trocar shaft 6116 may include at least two optical facets or viewing windows 6118a, 6118b that communicate with light transmitting structures within the trocar shaft (not shown). Trocar shaft 6116 also includes a medial engagement collar 6120 having circumferentially spaced apart fingers 6122 for interfingering or otherwise meshing with a complementary spaced apart fingers 5152 of a collar 5150 provided at the proximal end of the inner guide tube 5136 of access device 5000, as best seen in FIG. 55.

It is envisioned that the engagement collar 6120 on trocar shaft 6116 could be alternatively located at the distal end of the shaft, adjacent the cutting tip 6118, and the complementary collar 5150 could be located at the distal end of the inner guide tube 5136. The cooperative engagement of collars 5150 and 6120 effectively prevents relative radial movement of the trocar shaft 6115 and body portion 5120, caused by the torque transmitting by handle assembly 6100 during use.

Figure 53:
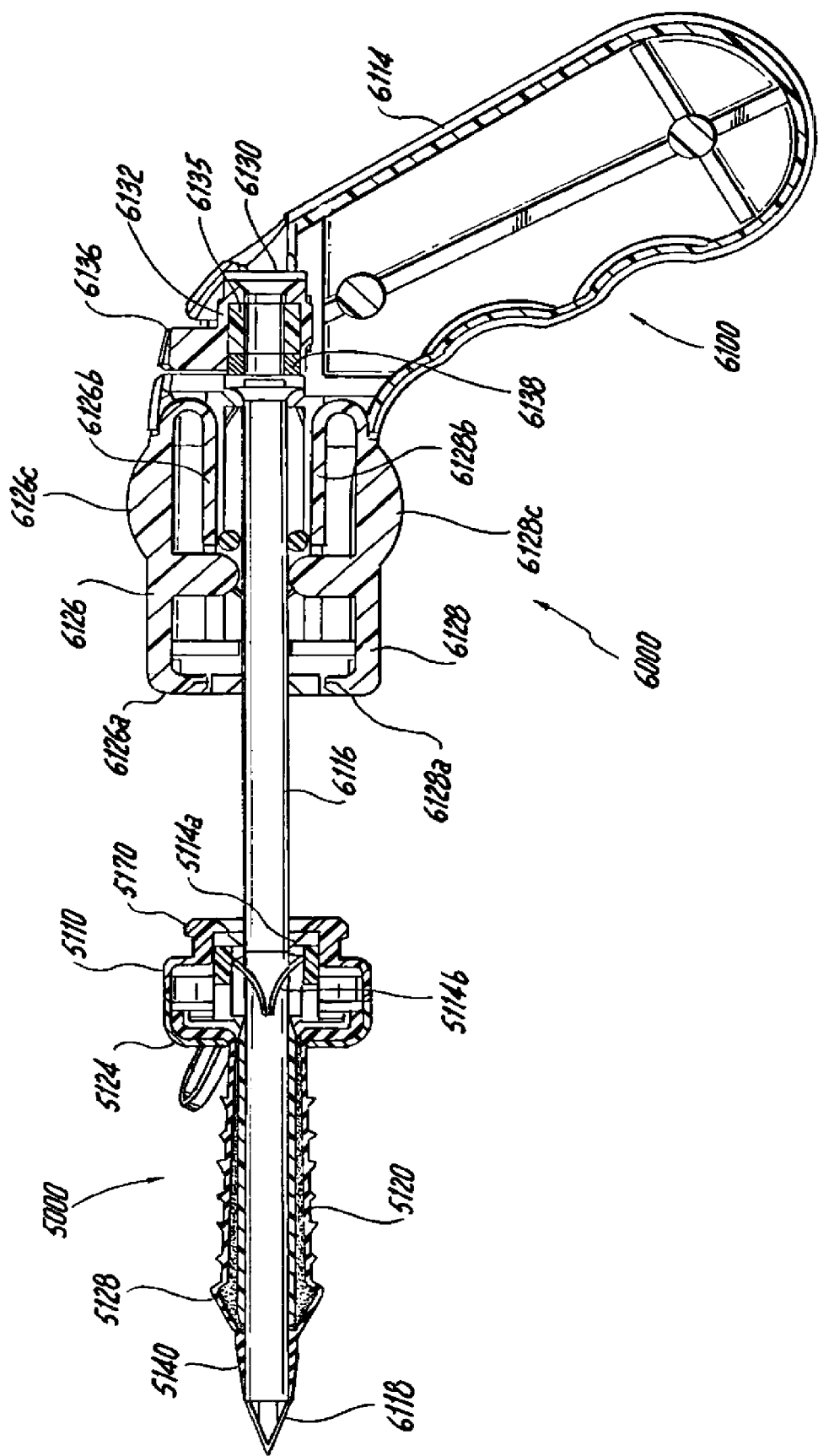
FIG. 53 is cross-sectional view taken along line 53-53 of FIG. 52 showing the insert device of FIG. 50 together with the surgical access device of FIG. 46 in an unstretched condition.

Referring now to FIG. 51, the proximal end of the trocar shaft 6116 has a flared end section 6124 that serves to axially secure the trocar shaft 6116 within the barrel section 6112 of housing assembly 6100. Handle assembly 6100 further includes a pair of latching arms 6126 and 6128 for releasably engaging a flange 5170 formed at the proximal end of access device housing 5110, as best seen in FIGS. 52 and 53. The latching arms 6126, 6128 pivot about respective pivot pins 6136, 6238 and have respective inwardly facing engagement fingers 6126a, 6128a and respective integral biasing legs 6126b, 6128b that urge the latching arms 6126 and 6128 into a latching position. The latching arms 6126, 6128 are released from the latching position by depressing the opposing integrally formed buttons 6126c, 6128c, which cause the latching arms 6126, 6128 to pivot away from one another.

Referring to FIGS. 51 and 53, the handle assembly 6100 of insertion device 6000 is adapted and configured to receive a laparo scope (not shown) used to communicate with the optical piercing tip 6118 of trocar haft 6116. More particularly, the proximal end of barrel section 6112 has a reception port 6130 for receiving a laparoscope.

In addition, the handle assembly 6100 of insertion device 6000 includes a mechanism for securing the position of a laparoscope relative to the handle assembly 6100 of the insertion device 6000. This mechanism includes a rotatable barrel cam 6132 having a cam slot 6134 that interacts with a corresponding cam follower (not shown). The barrel cam 6132 is rotated by way of a toggle switch 6136, which causes a corresponding axial translation of the barrel 6132. When the barrel cam 6132 moves in a distal direction, it axially compresses an aligned silicone washer 6135 against an aligned hard plastic retaining washer 6138. The silicone washer 6135 is restricted from expanding radially outwardly by the walls of the housing assembly 6100. Consequently, upon becoming axially compressed against hard plastic washer 6138, the pliable silicone washer 6135 will compress radially inwardly against the outer surface of the tubular laparoscope extending there through. As a result, the laparoscope is maintained is a fixed position with respect to the barrel section 6112 of handle assembly 6100.

In use, trocar tip 6118 and shaft 6116 are inserted into the proximal opening of access device 5000, as illustrated in FIG. 52. As the trocar shaft 6116 is inserted, the fingers 6122 on collar 6120 (see FIG. 50) engage corresponding fingers 5152 of collar 5150, at the proximal end of inner guide tube 5136 (see FIG. 48). Engagement of fingers 6122 and 5152 orients the inner guide tube 5136 and trocar shaft 6116 in a key and slot style. Housing 5110 is then drawn toward handle assembly 6100 to elongate and stretch elongate body portion 5100, until the latching arms 6126, 6128 engage flange 5170 to releasably lock the access device in the elongated configuration shown in FIGS. 49, 54 and 55).

The length of the trocar shaft 6116 from collar 6120 to penetration tip 6118 is selected so that the penetrating tip extends out of the inner guide tube to protrude from the end of the elongated body portion with the elongated body portion in the stretched position shown in FIGS. 54 and 55. Advantageously, because the fingers 6122 and 5152 at a location proximal to the trocar tip 6118 permits the trocar tip and the nosepiece 5140 to be configured to have a low profile and a very smooth gradual transition from trocar tip 6118 to the elongated body 5100 across nosepiece 5140. Engagement of fingers 6122 and 5152 also acts to extend the inner and outer guide tubes 5136, 5138 within the elongated body portion 5100.

With the elongated body portion 5100 mounted to the trocar 6116 as shown in FIG. 54, the access device 5000 is ready for use. The device 5000 may be inserted through the abdominal wall until the trocar tip 6118 enters the abdomen. If desired, an optical device such as an endoscope may be optionally inserted through a central bore of the trocar shaft 6116 to permit visualization through the optical window portions of the trocar tip 6118, to observe insertion of the trocar through the abdominal wall into the abdomen. With the trocar tip 6118 positioned inside the abdomen, the latching arms 6126, 6128 are released from flange 5170, which permits elongated body portion 5120 to resiliently return toward its initial unstretched configuration.

The elongated body portion 5120 may or may not return all the way to the original unstretched position, depending upon the thickness and gripping force of the surrounding tissue. However, the elongated body portion 5120 will return sufficiently toward the initial unstretched configuration so that the bulb portion 5128 expands radially outward to help secure or otherwise anchor the access device 5000 within the incision for surgery. The ribs 5130 variously disposed along the body portion 5120 also resume their rest position, extending radially outward from the body portion 5120 to assist in securing the access device 5000 relative to the patient's body.

At such a time, guide tubes 5136, 5138 return toward the nested configuration shown in FIG. 48. In this configuration, the access device 5000 presents a desirably low profile relative to the skin, so that instruments can be inserted and removed without obstruction from adjacent access devices. Thus, surgical instruments may be inserted and removed in the ordinary course of laparoscopic surgery to perform a surgical procedure. Guide tubes 5136, 5138 guide the surgical instruments into the body and protect the elastomeric elongated body portion 5120 from damage or puncture due to engagement with instruments having aggressively configured tips (such as clip appliers, staplers, etc.).

After surgery is complete, the trocar tip 6118 may be reinserted into the access device 5000 to elongate and stretch the elongated body 5120 for ease of removal from the patient's body. Alternatively, it is contemplated that the access device 5000 may simply be pulled out of the body, such as by grabbing and pulling on housing 5110. As the housing is pulled away from the body, elongate body 5120 will partially elongate and stretch against the resistance of the tissue until the bulb portion 5128 and ribs 5130 stretch sufficiently to slip out of the tissue and be removed.

Surgical access devices in accordance with the invention can serve many purposes, only one of which is use in minimally-invasive surgical procedures. It should be appreciated by those skilled in the art, that access ports in accordance with the invention can be used wherever access, particularly sealable access, into a body cavity is needed.

The specific dimensions of surgical access devices, including access ports, in accordance with the invention can be selected as needed. Specifically, it is envisioned that a wide variety of sizes will be available to a user to enable the user to select the most appropriately dimensioned device for the patient and procedure at hand. The overall length of access ports in accordance with the invention can vary, as well as the relative lengths of the neck portions, diameters and lengths of bulb portions, dimensions of the flange dimensions of the access port, and the like. It is envisioned that the access ports set forth herein can replace typical rigid cannulas. Accordingly, general dimensions similar to such typical rigid cannulas are possible, although an operative (during surgery) length of the surgical access port, which is less than that of typical cannulas, is preferable.

Materials for access ports in accordance with the invention can include, as set forth above, plastics, composites, elastomers or metals if necessary, for any component or components thereof. For example, the flange and or tip can be reinforced by rigid plastic or metal components. As set forth above, materials having directional properties may be desirable.

Figure 56:
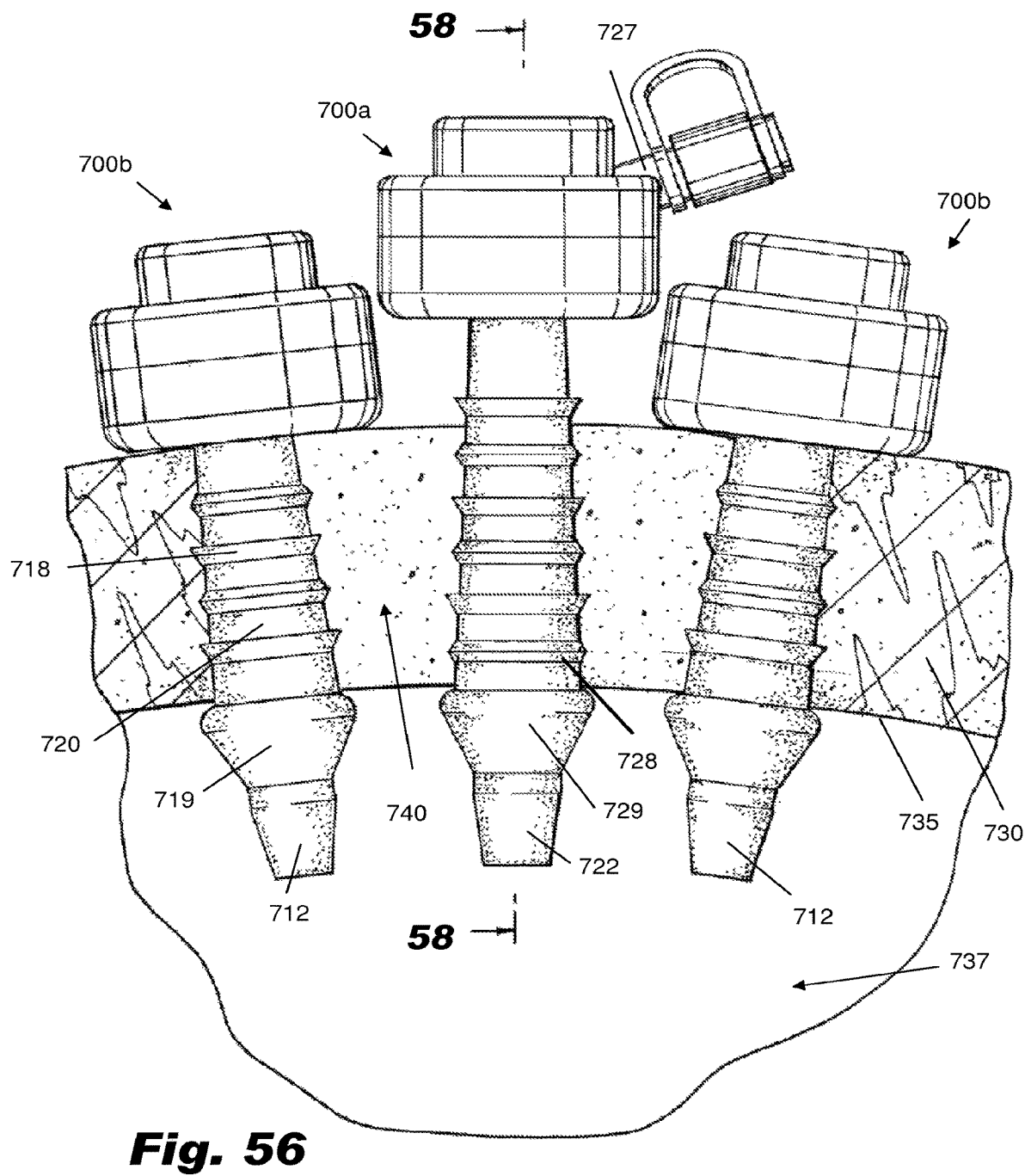
FIG. 56 is a side, cutaway view illustrating three access ports in accordance with the invention inserted through a single incision formed in the abdominal wall of a patient.
Figure 57:
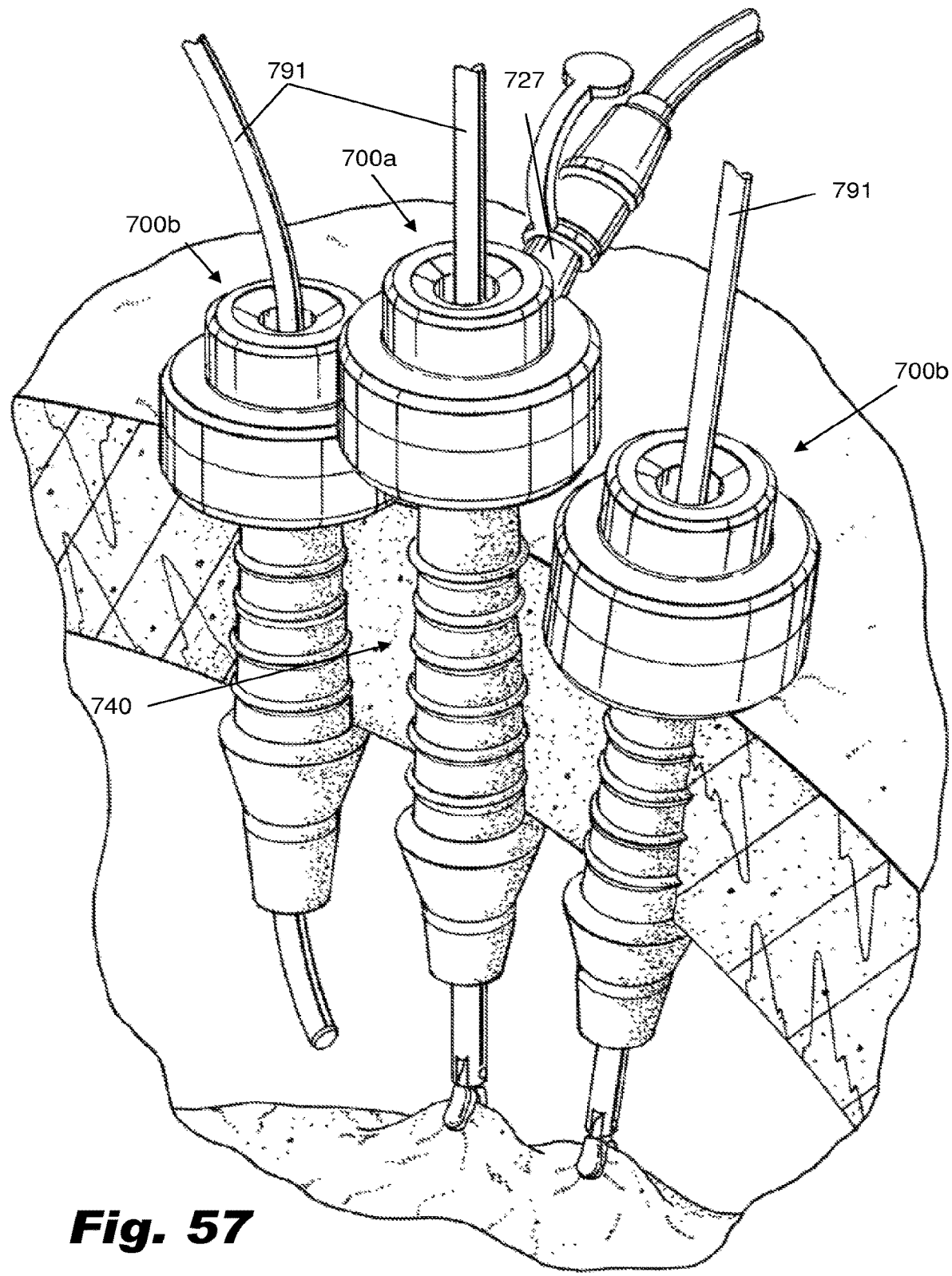
FIG. 57 is an isometric cutaway view of the arrangement of the three access ports of FIG. 56, inserted through a single incision formed in the abdominal wall of a patient.
Figure 58:
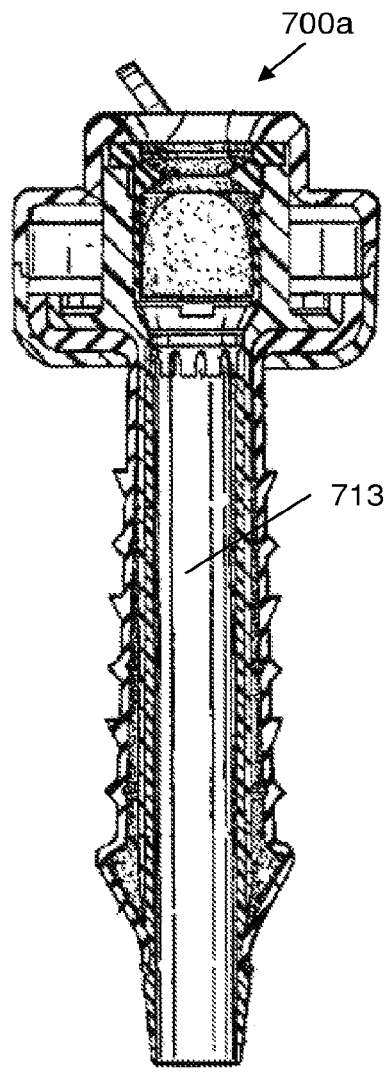
FIG. 58 is a cross-sectional view of one surgical access port of FIG. 56, taken across line 58-58 of FIG. 56.

FIG. 56 is a side, cutaway view illustrating three access ports 700a,b, in accordance with the invention inserted through a single incision 740 formed in the abdominal wall 730 of a patient. FIG. 57 is an isometric cutaway view of the illustrated arrangement, and FIG. 58 is a cross-sectional view of one surgical access port 700a, taken across line 58-58 of FIG. 56. The set of elastomeric surgical access ports 700a,b. As illustrated, for example, the central access port 700a is preferably longer than the two outer access ports 700b, which are used together, in accordance with the invention. Advantageously, the elastomeric surgical access ports 700a,b, minimize protrusion beyond the inner surface 735 of the abdominal wall 730 of the patient. Access devices 700a,b, which can be constructed in accordance with one or more of U.S. patent application Ser. No. 11/786,832 and U.S. patent application Ser. No. 11/544,856, are extended longitudinally during insertion to reduce the insertion profile of the access device 700a,b, but are allowed to contract longitudinally following insertion, due to the inherent elasticity of the body of the access device. When contracted, the distal portions 712, 722 of the access devices 700a,b engage the inner surface 735 of the abdominal wall 730 or other anatomy, and thus do not interfere with anatomy, instruments or other access devices, in the operative space 737 any more than necessary, while still ensuring secure engagement with the abdominal wall 730 or other anatomical structure.

Figure 65:
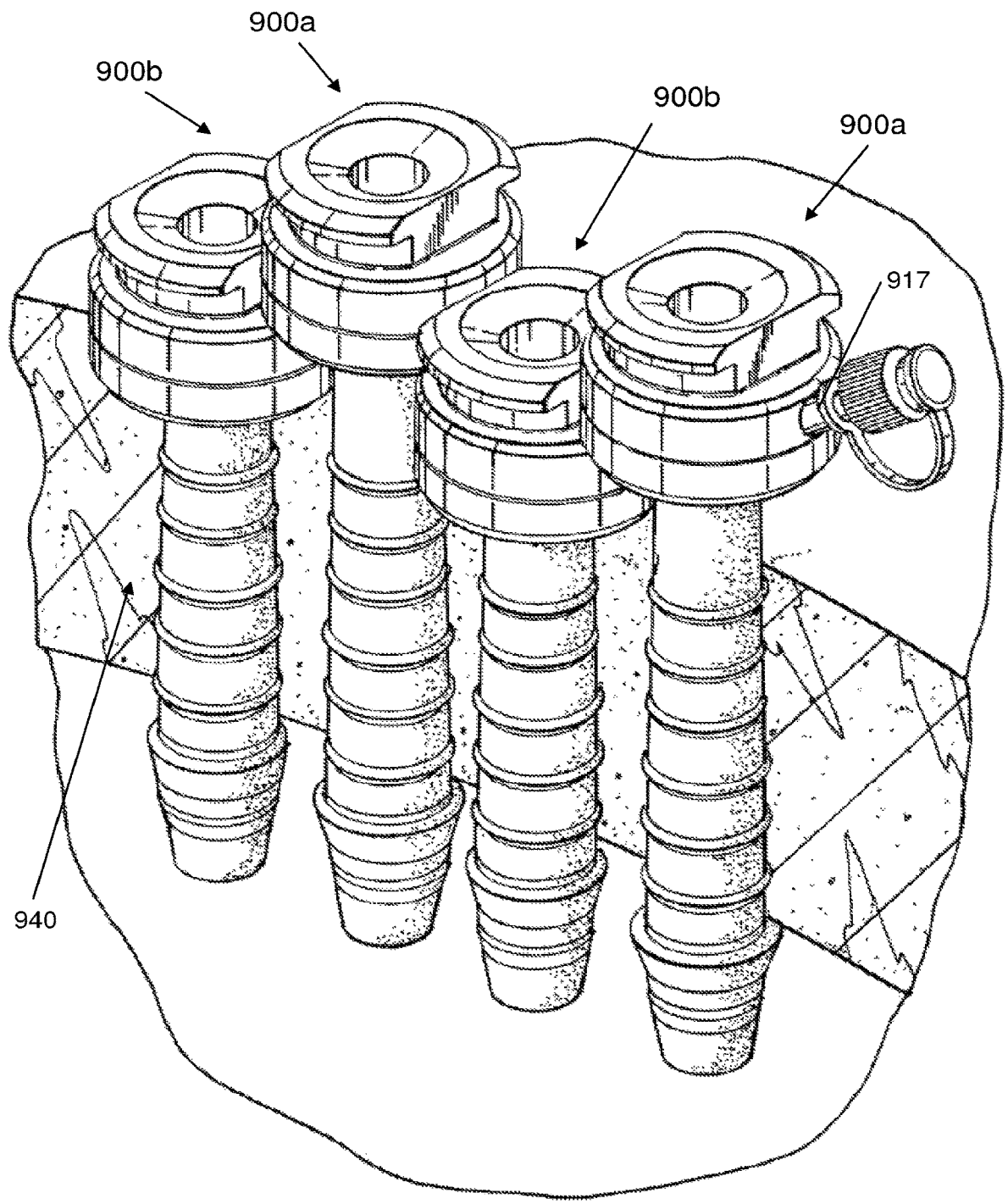
FIG. 65 is an isometric partial cutaway view of four surgical access devices in accordance with the embodiment of FIG. 61 inserted through a single linear incision, wherein mutual nesting permits close positioning of adjacent ports.

Although in the illustrations of FIGS. 56-57, the center access device 700a is longer than the outer access devices 700b, it is to be understood that this embodiment is only for the purpose of providing an illustration, and that any number of access ports can be provided in any orientation, in accordance with the invention. For example, the outer access devices 700b can be longer and nest above the inner access device 700a, or one of the end access devices 700b can extend over the central access device 700a, with the remaining end access device 700b remaining even with the inner access device 700a. Of course, any number of access ports—for example fewer or greater than three, can be provided. For example, a fourth access port can be nested above either the right or left access devices 700b (as illustrated in FIG. 65) and so on. Moreover, the extent of overlap between mutually nested adjacent access devices 700a,b can be adjusted to suit the specific situation. That is, the spacing between adjacent access devices can be adjusted as necessary, depending on the precise requirements of the procedure being performed, while the arrangement can afford relative movement between adjacent access devices.

Devices in accordance with the invention, providing an extendible and nesting capabilities reduces the incision length while allowing the surgeon to manipulate the access devices 700a,b as necessary, while maintaining anchoring with the abdominal wall 730 or other anatomical structure, which is afforded by a distal bulb portion 719, 729 and engagement elements 718, 728 provided along the outer portion of each respective access device 700a,b.

As illustrated, one or more luer connections 727 can be provided on one or more access devices (e.g. device 700a) for providing insufflation or alternatively irrigation fluids. The luer connections 717 can be omitted from some access devices, as with the outer access devices 700b. Alternatively, insufflation can removed from the access devices 700a,b entirely and performed by way of a separate insufflation device, such as another access device or a veress needle, for example.

As best illustrated in FIG. 57, an incision 740 is formed in the abdominal wall 730 of the patient. Then, a plurality of access ports 700a,b are sequentially inserted into the incision 740 in a nested configuration, to minimize the lateral space required by multiple ports 700a,b. Such an arrangement also facilitates manipulation of instruments 791 through the ports 700a,b being used. As mentioned, it is to be understood that although three ports are shown, any plurality of ports can be utilized in this configuration to achieve the advantages of the invention—namely, reduced incision length, which results in reduced trauma to the patient, and less scarring, and easier manipulation of instruments 791

Each of the access ports 700a,b illustrated are formed, in-part, of an elastomeric material, but it is to be understood that different access devices (e.g., ports, trocars) of different materials can be used in combination with those described and illustrated herein, if so desired. Each of the illustrated access ports 700a,b includes an elongated body 720 with opposed proximal and distal end portions, which defines a longitudinal axis. The body 720 has a central lumen extending therethrough, which in-turn includes a resilient bulb portion 719, 729 formed between the proximal and distal end portions of the body 720. The resilient bulb portion 719, 729 is adapted and configured to transition between a first condition in which the bulb portion 719, 729 has a first diameter and a first length and a second condition in which the bulb portion 719, 729 has a second diameter and a second length. The second diameter of the bulb portion 719, 729 is less than the first diameter, and the second length of the bulb portion 719, 729 is greater than the first length. In accordance with the invention, the access devices used can incorporate an internal guide tube 713, which tubes can be configured to extend longitudinally when the access device extends.

In accordance with one aspect of the invention, multiple identical access devices can be used, with certain ones of such access devices remaining in a fully or partially extended state during use, with others remaining in a contracted or predominantly contracted state.

Alternatively, a combination of access devices 700 having different relaxed lengths can be utilized—particularly a combination of "long" access devices 700a and "short" access devices 700b, the long access device being longer than the short access device by an amount sufficient to allow the long access device 700a to remain in a relaxed position while sitting beyond the short access device 700b by a distance sufficient to allow a proximal end portion of the short access 700b device to nest below the proximal end portion of the long access device 700a.

Figure 59:
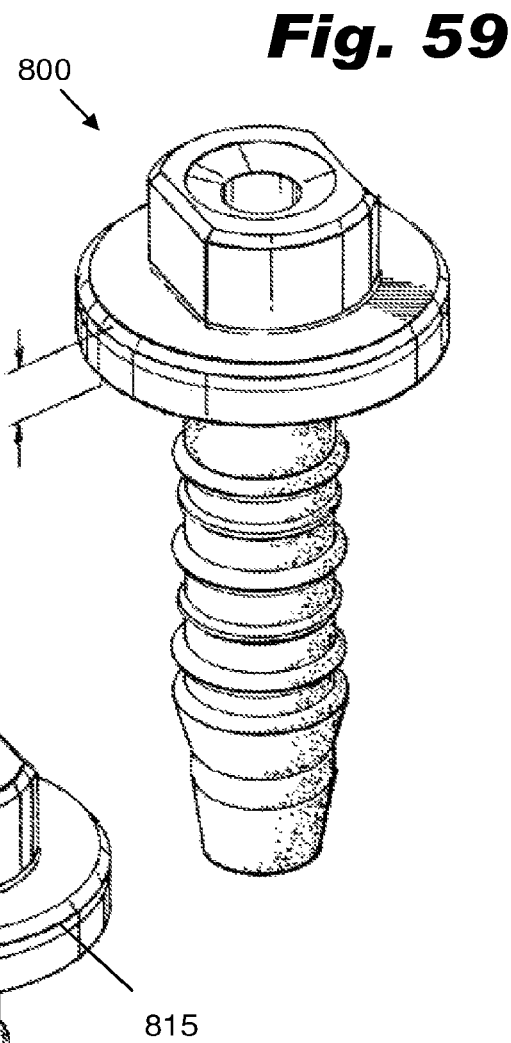
FIG. 59 is an isometric view of a surgical access port having a low-profile for use in conjunction with single-incision surgeries.
Figure 60:
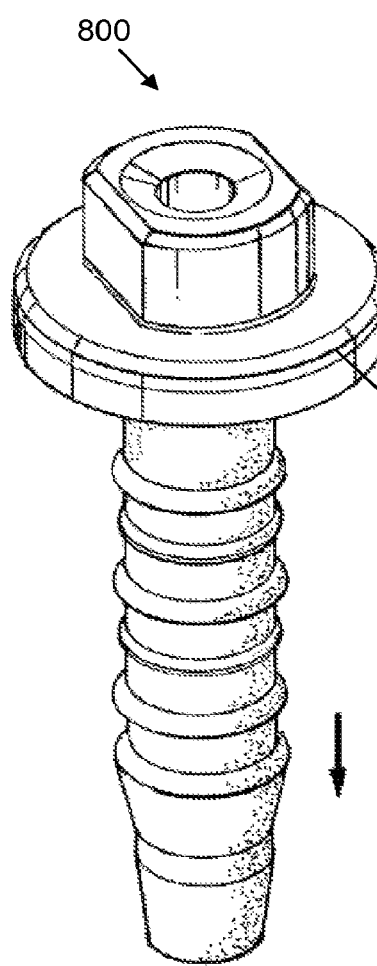
FIG. 60 is an isometric view of the surgical access port of FIG. 59, in a longitudinally extended configuration.

FIG. 59 is an isometric view of a surgical access port 800 having a low-profile proximal end housing for use in conjunction with single-incision surgeries, and FIG. 60 is an isometric view of the surgical access port 800 shown in a longitudinally extended configuration. One or more such access devices 800 can be utilized, that have a proximal end portion 815 that is particularly adapted for utilization in a nested configuration. Such proximal end portions 815 can include a low-profile housing, which can include one or more chambers for providing insufflation or irrigation fluids, or the like, or for evacuation of such fluids. A height dimension 892 of the widest portion of the access port 800 housing is minimized in accordance with the invention. Such dimension 892 can be on the order of about 1.0 cm, for example. Alternatively, such access devices 800 can include one or more valves, and/or a non-mechanical fluidic seals, such as those described in U.S. patent Ser. No. 11/517,929, for example, which application is incorporated herein by reference in its entirety.

The subject invention is particularly advantageous for performing laparoscopic abdominal procedures, allowing for sealed insertion of multiple instruments at the same time, while minimizing trauma and scarring. For example, in the case of a hysterectomy, an incision can be made in the lower portion of the abdomen to provide access to a patient's uterus. The relevant instruments can be inserted through the surgical access devices 700a,b, including but not limited to endoscopes, scalpels, graspers, morsellators, cautery devices, clamps, specimen retrieval pouches, and the like.

FIGS. 61-66 illustrate a further embodiment of a surgical access port 900 having a low-profile for use in conjunction with single-incision surgeries. FIG. 62 is a cross-sectional view of the surgical access port 900, taken along line 62-62.

The surgical access port 900 includes an overall low-profile housing 930, which as illustrated includes upper 930a and lower 930b halves. The elastomeric body 920 is supported at one end by the housing 930 and at the distal end by a nosepiece 940, in-turn supported by an inner telescoping guide tube 913 having upper 913a and lower 913b telescoping portions. The access port 900 includes an insufflation connection 917. In accordance with the invention, however, the port 900 can be provided without such feature. As discussed above, a kit can be provided with one or more ports having an insufflation connection, and one or more ports being provided without an insufflation connection, as shown for example in FIGS. 64, 65 and 66.

The access port 900 includes in the housing 930 thereof, a connection feature 970 to facilitate connection with an insertion device, and one or more flat portions 935 for aligning the housing 930 with an insertion device. Advantageously, this feature also reduces the size of the housing 930 somewhat to permit close positioning of adjacent ports 900. The configuration of the housing 930 and the connection feature 970 permit an overall low profile of the access port 900 during insertion.

The housing 930 is also provided with a guide portion 933, to protect the upper seal member 914 from sharp surgical instruments, and to maintain the position thereof, within the housing 930, inhibiting inversion of the seal member 914 The upper seal member 914 is preferably configured to seal against a shaft of an instrument inserted therethrough, while a lower seal member 909 is preferably adapted to seal a central lumen of the access port in the absence of a surgical instrument.

Figure 64:
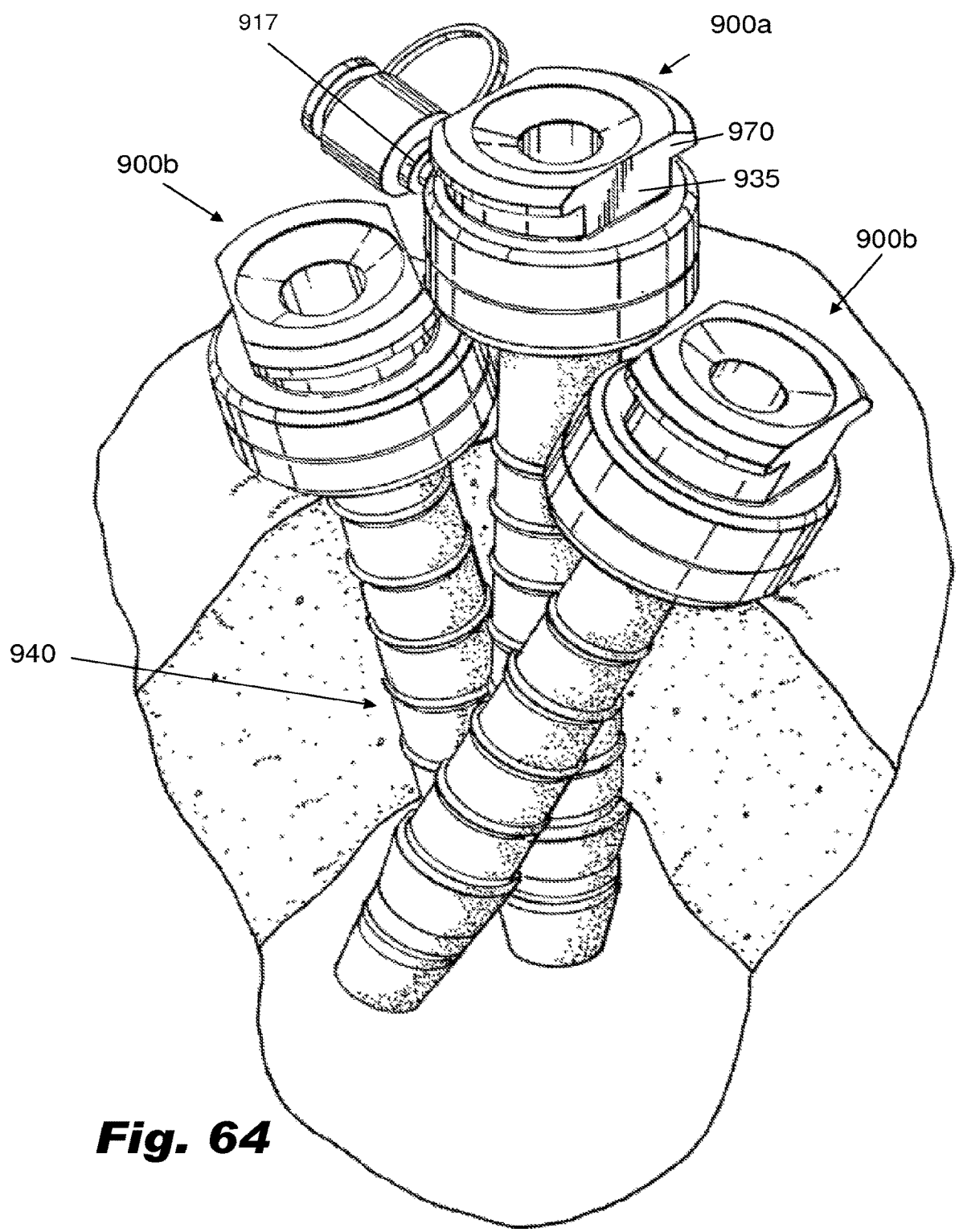
FIG. 64 is an isometric partial cutaway view of three surgical access devices in accordance with the embodiment of FIG. 61 inserted through a small single incision, such as through an incision made through the umbilicus of a patient, to minimize scarring.

FIG. 64 is an isometric partial cutaway view showing three surgical access devices in accordance with the embodiment of FIG. 61 inserted through a small single incision 940, such as through an incision made through the umbilicus of a patient, to minimize scarring;

FIG. 65 is an isometric partial cutaway view showing four surgical access devices in accordance with the embodiment of FIG. 61 inserted through a single linear incision 940, wherein mutual nesting permits close positioning of adjacent ports 900a,b.

Figure 66:
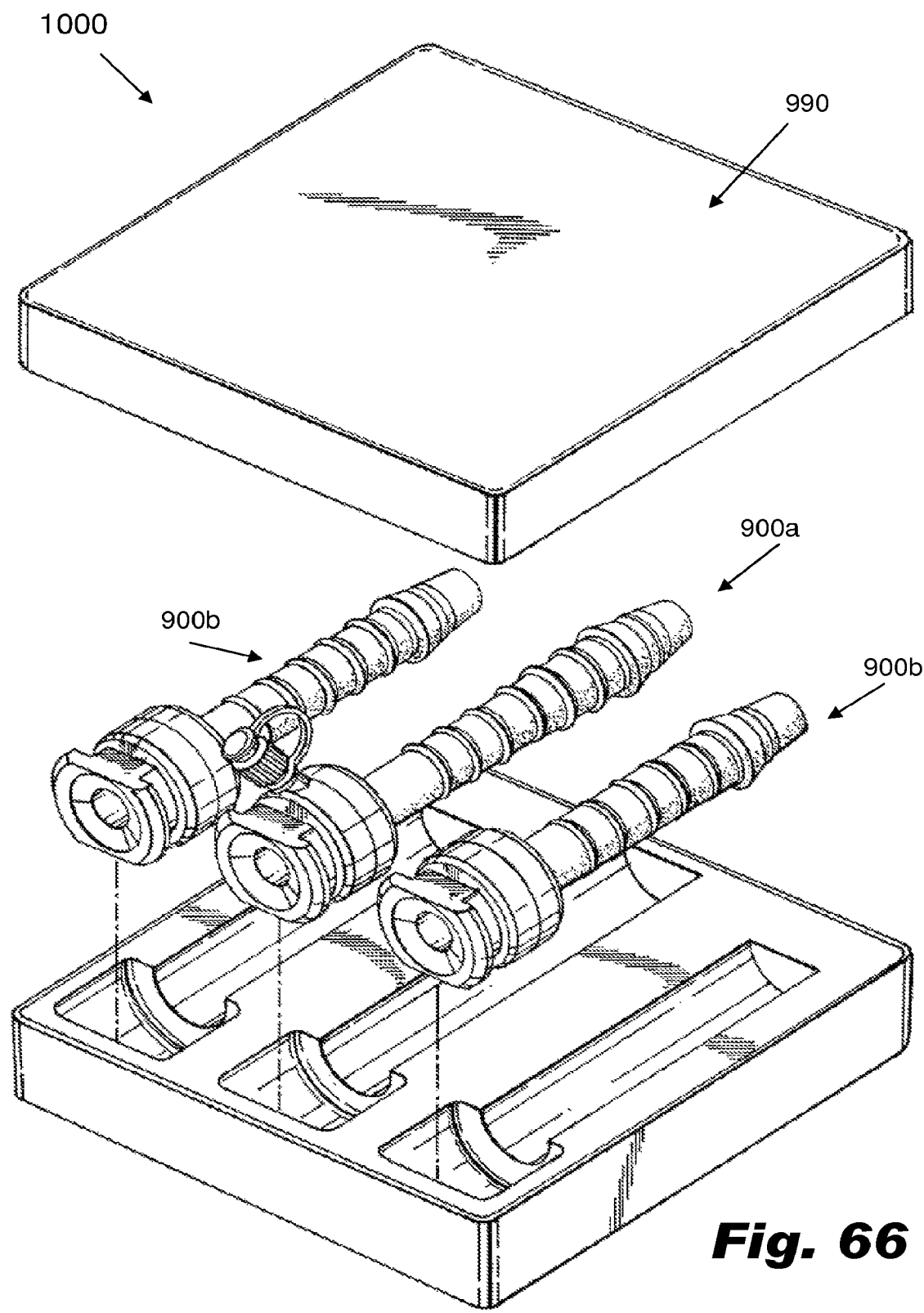
FIG. 66 is a kit in accordance with the invention having a plurality of surgical access ports, also in accordance with the invention.

FIG. 66 is a kit 1000 in accordance with the invention having a plurality of surgical access ports 900a,b, in a package 990, in accordance with the invention.

Any of the surgical access devices set forth above can be used in connection with the methods and kits hereof, without limitation, in keeping with the invention. It is to be understood that any feature disclosed in connection with one embodiment of the subject devices can be incorporated into another embodiment in accordance with the invention, without limitation, except where features are mutually exclusive. Such features include, for the purpose of providing non-limiting examples, optional features, materials, construction and assembly features and/or steps, sealing configurations, body configurations, guide tube configurations, inserter-coupling elements, and/or insufflation capability-related features.

It is to be understood that the subject invention can advantageously be applied to various surgical procedures. The devices, systems and methods of the present invention, as described above and shown in the drawings, provide for advantageous devices, kits and methods therefor. It will be apparent to those skilled in the art that various modifications and variations can be made in the devices, kits and methods of the present invention without departing from the spirit or scope of the invention. Thus, it is intended that the present invention include all such modifications and variations.

The invention claimed is:

1. An insertion device for a surgical access device used to perform a laparoscopic procedure, comprising:

a) a handle assembly including an ergonomic grip section and an elongated barrel section, wherein the barrel section includes a proximal reception port for receiving a laparoscope; and b) an elongated trocar shaft extending distally from the barrel section and having a tissue-piercing optical tip at a distal end thereof for visualization, the trocar shaft having a first engagement collar positioned at a fixed location on an exterior surface thereof and having a plurality of circumferentially spaced apart stationary engagement fingers for interfingered engagement with complementary circumferentially spaced apart stationary engagement fingers of a second engagement collar that is located within a guide tube of the surgical access device, wherein the engagement fingers of the first engagement collar engage with the engagement fingers of the second engagement collar when the trocar shaft is inserted into the guide tube of the surgical access device, so as to prevent relative radial movement of the trocar shaft and the surgical access device, and wherein the trocar shaft has a central bore communicating with the reception port of the barrel section and extending to the optical tip for accommodating the laparoscope.

2. The insertion device recited in claim 1, wherein the optical tip includes at least two optical cutting facets.

3. The insertion device recited in claim 1, wherein the first engagement collar is located at a medial section of the trocar shaft.

4. The insertion device recited in claim 1, wherein the first engagement collar is located at the distal end of the trocar shaft, adjacent the optical tip.

5. The insertion device recited in claim 1, further comprising a locking mechanism operatively associated with the barrel section of the handle assembly for securing the position of the laparoscope relative to the handle assembly.

6. The insertion device recited in claim 5, wherein the locking mechanism includes a rotatable barrel cam.

7. The insertion device recited in claim 1, further comprising a pair of pivoting latching arms operatively associated with the barrel section of the handle assembly for releasably engaging the access device.

8. The insertion device recited in claim 7, wherein the latching arms are biased into a latching position.

* * * * *